United States Patent
Bolea et al.

(10) Patent No.: US 9,765,091 B2
(45) Date of Patent: Sep. 19, 2017

(54) TETRAHYDROPYRAZOLO [3,4-B] AZEPINE DERIVATIVES AND THEIR USE AS ALLOSTERIC MODULATORS OF METABOTROPIC GLUTAMATE RECEPTORS

(75) Inventors: Christelle Bolea, Geneva (CH); Sylvain Celanire, Geneva (CG); Lam Tang, Geneva (CH); Nigel J. Liverton, Harleysville, PA (US); Philip Jones, Houston, TX (US)

(73) Assignees: Addex Pharma S.A., Geneva (CH); Merck Sharp & Dohme Corp., Rahway, NJ (US)

( * ) Notice: Subject to any disclaimer, the term of this patent is extended or adjusted under 35 U.S.C. 154(b) by 813 days.

(21) Appl. No.: 13/809,581

(22) PCT Filed: Jul. 11, 2011

(86) PCT No.: PCT/US2011/001207
§ 371 (c)(1),
(2), (4) Date: Jun. 12, 2013

(87) PCT Pub. No.: WO2012/009001
PCT Pub. Date: Jan. 19, 2012

(65) Prior Publication Data
US 2013/0267499 A1    Oct. 10, 2013

Related U.S. Application Data

(60) Provisional application No. 61/571,071, filed on Jun. 20, 2011.

(30) Foreign Application Priority Data

Jul. 14, 2010 (GB) .................................. 1011831.3

(51) Int. Cl.
| | |
|---|---|
| *C07D 513/12* | (2006.01) |
| *A61K 31/4162* | (2006.01) |
| *A61K 31/429* | (2006.01) |
| *A61K 31/55* | (2006.01) |
| *A61K 45/06* | (2006.01) |
| *C07D 513/04* | (2006.01) |
| *C07D 513/14* | (2006.01) |
| *A61K 31/433* | (2006.01) |
| *A61K 31/4439* | (2006.01) |
| *A61K 31/506* | (2006.01) |
| *A61B 5/00* | (2006.01) |

(Continued)

(52) U.S. Cl.
CPC ............. *C07D 513/12* (2013.01); *A23L 5/00* (2016.08); *A61B 5/00* (2013.01); *A61K 9/0019* (2013.01); *A61K 9/0095* (2013.01); *A61K 9/06* (2013.01); *A61K 9/10* (2013.01); *A61K 9/2059* (2013.01); *A61K 31/429* (2013.01); *A61K 31/433* (2013.01); *A61K 31/4439* (2013.01); *A61K 31/506* (2013.01); *A61K 31/55* (2013.01); *A61K 45/06* (2013.01); *C07D 513/04* (2013.01); *C07D 513/14* (2013.01)

(58) Field of Classification Search
CPC .. C07D 487/04; C07D 471/04; C07D 495/04; C07D 491/04; C07D 513/12; A61K 31/55; A61K 31/4162; A61K 31/429; A61K 45/06
USPC ................ 514/215, 217, 366; 540/578, 586; 548/151, 181, 359.5
See application file for complete search history.

(56) References Cited

U.S. PATENT DOCUMENTS

| | | | |
|---|---|---|---|
| 2010/0144756 A1 | 6/2010 | Bolea et al. | |
| 2010/0249109 A1 | 9/2010 | Lapierre et al. | |
| 2014/0349994 A1* | 11/2014 | Bolea ................... | C07D 513/04 514/210.21 |

FOREIGN PATENT DOCUMENTS

| | | |
|---|---|---|
| WO | WO-96/09304 A1 | 3/1996 |
| WO | WO-2005/007096 A2 | 1/2005 |

(Continued)

OTHER PUBLICATIONS

Battaglia, G., et al., Pharmacological Activation of mGlu4 Metabotropic Glutamate Receptors Reduces . . . , Journal of Neuroscience, 2006, vol. 26(27), pp. 7222-7229.
Besong, G., et al., Activation of Group III Metabotropic Glutamate Receptors Inhibits the Production of Rantes . . . , Journal of Neuroscience, 2002, vol. 22(13), pp. 5403-5411.
Bradley, S., et al., Immunohistochemical Localization of Subtype 4a Metabotropic Glutamate Receptors . . . , Journal of Comparative Neurology, 1999, vol. 407, pp. 33-46.

(Continued)

*Primary Examiner* — Matthew Coughlin
*Assistant Examiner* — Sagar Patel
(74) *Attorney, Agent, or Firm* — Law Offices of Gerard Bilotto, P.C.; Gerard Bilotto

(57) ABSTRACT

The present invention relates to novel compounds of Formula (I), wherein M, A and Y are defined as in Formula (I); invention compounds are modulators of metabotropic glutamate receptors—subtype 4 ("mGluR$_4$") which are useful for the treatment or prevention of central nervous system disorders as well as other disorders modulated by mGluR$_4$ receptors. The invention is also directed to pharmaceutical compositions and the use of such compounds in the manufacture of medicaments, as well as to the use of such compounds for the prevention and treatment of such diseases in which mGluR$_4$ is involved.

(I)

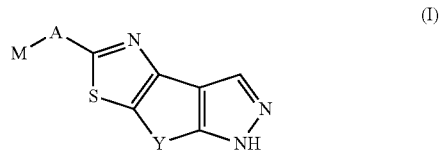

20 Claims, No Drawings

(51) Int. Cl.
 A61K 9/00 (2006.01)
 A61K 9/06 (2006.01)
 A61K 9/10 (2006.01)
 A61K 9/20 (2006.01)
 A23L 5/00 (2016.01)

(56) References Cited

FOREIGN PATENT DOCUMENTS

| WO | WO-2006/040279 A1 | 4/2006 |
| WO | WO-2009/010454 A2 | 1/2009 |
| WO | WO-2009/010455 A2 | 1/2009 |
| WO | WO-2010/079238 A1 | 7/2010 |

OTHER PUBLICATIONS

Bruno, V., et al., Selective Activation of mGlu4 Metabotropic Glutamate Receptors Is Protective . . . , Journal of Neuroscience, 2000, vol. 20(17), pp. 6413-6420.
Conn, P.J., et al., Metabotropic Glutamate Receptors in the Basal Ganglia Motor Circuit, Nature Review Neuroscience, 2005, vol. 6, pp. 787-798, Nature Publishing Group.
Corti, C., et al., Distribution and Synaptic Localisation of the Metabotropic Glutamate . . . , Neuroscience, 2002, vol. 110(3), pp. 403-420, Elsevier Science Ltd, Great Britain.
East, S., et al., mGluR4 Positive Allosteric Modulators with Potential for the Treatment of Parkinson's Disease, Expert Opinion Ther. Patents, 2010, vol. 20(3), pp. 441-445.
Engers, D., et al, Synthesis and Evaluation of a Series of Heterobiarylamides . . . , Journal of Medicinal Chemistry, 2009, vol. 52(14), pp. 4115-4118, American Chemical Society.
Johnson, M.P., et al., Modulation of Stress-Induced and Stimulated Hyperprolactinemia with the Group . . . , Neuropharmacology, 2002, vol. 43, pp. 799-808, Elsevier Science Ltd.
Johnson, M.P., et al., Discovery of Allosteric Potentiators . . . , Journal of Medicinal Chemistry, 2003, vol. 46(15), pp. 3189-3192, American Chemical Society.
Johnson, M.P., et al., Allosteric Modulators of Metabotropic Glutamate Receptors . . . , Biochemical Society Transactions, 2004, vol. 32(5), pp. 881-887, Biochemical Society.
Kew, J., Positive and Negative Allosteric Modulation of Metabotropic Glutamate Receptors . . . , Pharmacology & Therapeutics, 2004, vol. 104(3), pp. 233-244, Elsevier Inc.
Knoflach, F., et al., Positive Allosteric Modulators of Metabotropic Glutamate 1 Receptor . . . , Proc. Natl. Acad. Sci. USA, 2001, vol. 98(23), pp. 13402-13407.
Konieczny, J., et al., The Influence of Group III Metabotropic Glutamate Receptor Stimulation by . . . , Neuroscience, 2007, vol. 145, pp. 611-620, Elsevier Ltd.
Lopez, S., et al., Targeting Group III Metabotropic Glutamate Receptors Produces . . . , Journal of Neuroscience, 2007, vol. 27(25), pp. 6701-6711, Society for Neuroscience.
Maj, M., et al., (-)-PHCCC a Positive Allosteric Modulator of mGluR4: Characterization, Mechanism of Action . . . , Neuropharmacology, 2003, vol. 45, pp. 895-906, Elsevier Ltd.
Marino, M., et al., Localization and Physiological Roles of Metabotropic Glutamate Receptors in the Direct and Indirect . . . , Amino Acids, 2002, vol. 23, pp. 185-191, Austria.
Marino, M., et al., Allosteric Modulation of Group III Metabotropic Glutamate Receptor 4: a Potential . . . , Proc. Natl. Acad. Sci. USA, 2003, vol. 100(23), pp. 13668-13673.
Marino, M., et al., Targeting the Metabotropic Glutamate Receptor . . . , Current Topics in Medicinal Chemistry, 2005, vol. 5(9), pp. 885-895, Bentham Science Publishers, Ltd.
Mathiesen, J., et al., Positive Allosteric Modulation of the Human Metabotropic . . . , British Journal of Pharmacology, 2003, vol. 138(6), pp. 1026-1030, Nature Publishing Group.
Millan, C., et al., Subtype-specific Expression of Group . . . , Journal of Biological Chemistry, 2002, vol. 277(49), pp. 47796-47803, American Soc. Biochem. & Molec. Biology Inc.
Mitsukawa, K., et al., A Selective Metabotropic Glutamate Receptor 7 Agonist: Activation of Receptor . . . , Proc. Natl. Acad. Sci. USA, 2005, vol. 102(51), pp. 18712-18717.
Monastyrskaia, K., et al., Effect of the Umami Peptides on the Ligand Binding and Function . . . , British Journal of Pharmacology, 1999, vol. 128, pp. 1027-1034, Stockton Press.
Mutel, V., Therapeutic Potential of Non-Competitive, Subtype-Selective Metabotropic . . . , Expert Opinion Ther. Patents, 2002, vol. 12(12), pp. 1-8, Ashley Publications Ltd.
Nakanishi, S., et al., Glutamate Receptors: Brain Function and Signal Transduction, Brain Research Reviews, 1998, vol. 26, pp. 230-235, Elsevier Science B.V.
Niswender, C., et al., Positive Allosteric Modulators of the Metabotropic Glutamate . . . , Bioorganic & Medicinal Chemistry Letters, 2008, vol. 18, pp. 5626-5630, Elsevier Ltd.
Niswender, C., et al., Discovery, Characterization, and . . . , Molecular Pharmacology, 2008, vol. 74(5), pp. 1345-1358, Amer. Soc. for Pharmacology & Experim. Therapeutics, USA.
O'Brien, J., et al., A Family of Highly Selective Allosteric . . . , Molecular Pharmacology, 2003, vol. 64(3), pp. 731-740, Amer.Soc. for Pharmacology & Experim.Therapeutics, USA.
Page, A., et al., Metabotropic Glutamate Receptors Inhibit Mechanosensitivity in Vagal . . . , Gastroenterology, 2005, vol. 128, pp. 402-410, American Gastroenterological Assoc.
Ritzen, A., et al., Molecular Pharmacology and Therapeutic Prospects . . . , Basic & Clinical Pharmacol. & Toxicol., 2005, vol. 97, pp. 202-213, Pharmacology & Toxicology,Denmark.
Schoepp, D., et al., Pharmacological Agents Acting at Subtypes of Metabotropic Glutamate Receptors, Neuropharmacology, 1999, vol. 38, pp. 1431-1476, Elsevier Science Ltd.
Stachowicz, K., et al., Anxiolytic-like effects of PHCCC, an allosteric modulator of mGlu4 . . . , European Journal of Pharmacology, 2004, vol. 498, pp. 153-156, Elsevier B.V.
Tatarczynska, E., et al., Anxiolytic- and Antidepressant-Like Effects of Group III . . . , Polish Journal of Pharmacol., 2002, vol. 54(6), pp. 707-710, Institute of Pharmacology.
Toyono, T., et al., Expression of the Metabotropic Glutamate Receptor, mGluR4A, in the Taste Hairs of Taste Buds in Rat . . . , Arch. Histol. Cytol., 2002, vol. 65(1), pp. 91-96.
Uehara, S., et al., Metabotropic Glutamate Receptor Type 4 Is Involved in Autoinhibitory Cascade . . . , Diabetes, 2004, vol. 53, pp. 998-1006, American Diabetes Association.
Valenti, O., et al., Group III Metabotropic Glutamate Receptor-Mediated Modulation . . . , Journal of Neuroscience, 2003, vol. 23(18), pp. 7218-7226, Society for Neuroscience.
Valenti, O., et al., Group III Metabotropic . . . , Journal of Pharmacol. & Experim. Therapeutics, 2005, vol. 313(3), pp. 1296-1304, Amer. Soc. for Pharmacol.& Experim. Ther.,USA.
Vernon, A., et al., Neuroprotective Effects of Metabotropic . . . , European Journal of Neuroscience, 2005, vol. 22, pp. 1799-1806, Federation of European Neuroscience Societies.
Williams, R., et al., Positive Allosteric Modulators of the Metabotropic Glutamate . . . , Bioorganic & Medicinal Chemistry Letters, 2009, vol. 19, pp. 962-966, Elsevier Ltd.
Williams, R., et al., Re-exploration of the PHCCC Scaffold: Discovery of Improved . . . , ACS Chemical Neuroscience, 2010, vol. 1(6), pp. 411-419, American Chemical Society.
Wilson, J. et al., Identification of Novel Positive Allosteric Modulators of mGlu8 Receptor, Neuropharmacology, 2005, vol. 49, p. 278.
Young, R., et al., Anatomy and Function of Group III Metabotropic Glutamate Receptors in Gastric Vagal Pathways, Neuropharmacology, 2008, vol. 54, pp. 965-975, Elsevier Ltd.
Hong, S., et al., Tricyclic Thiazolopyrazole Derivatives as Metabotropic Glutamate Receptor . . . , Journal of Medicinal Chemistry, 2011, vol. 54, p. 5070-5081, American Chemical Soc.
Robichaud, A., et al., Recent Progress on the Identification of Metabotropic Glutamate 4 . . . , ACS Chemical Neuroscience, 2011, vol. 2, pp. 433-449, American Chemical Society.
Stachowicz, K., et al., The Group III mGlu Receptor Agonist ACPT-I Exerts Anxiolytic-like . . . , Neuropharmacology, 2009, vol. 57, pp. 227-234, Elsevier.

(56) References Cited

OTHER PUBLICATIONS

Yanamala, N., et al., Preferential Binding of Allosteric Modulators to Active and Inactive . . . , BMC Bioinformatics, 2008, vol. 9(Suppl I): S16, BioMed Central.

* cited by examiner

TETRAHYDROPYRAZOLO [3,4-B] AZEPINE DERIVATIVES AND THEIR USE AS ALLOSTERIC MODULATORS OF METABOTROPIC GLUTAMATE RECEPTORS

CROSS-REFERENCE TO RELATED APPLICATIONS

This application is a national stage application under 35 U.S.C. §371 of PCT/US11/01207, filed on Jul. 11, 2011, which claims benefit from U.S. Provisional application Ser. No. 61/571,071 filed on Jun. 20, 2011 and priority under 35 U.S.C. §119(a-d) and 365(b) to GB 1011831.3, filed on Jul. 14, 2010.

SUMMARY OF THE INVENTION

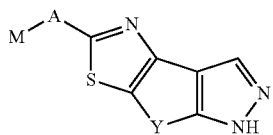

The present invention relates to novel compounds of Formula (I), wherein M, A and Y are defined as in Formula (I); invention compounds are modulators of metabotropic glutamate receptors—subtype 4 ("mGluR$_4$") which are useful for the treatment or prevention of central nervous system disorders as well as other disorders modulated by mGluR$_4$ receptors. The invention is also directed to pharmaceutical compositions and the use of such compounds in the manufacture of medicaments, as well as to the use of such compounds for the prevention and treatment of such diseases in which mGluR$_4$ is involved.

BACKGROUND OF THE INVENTION

Glutamate is the major amino-acid transmitter in the mammalian central nervous system (CNS). Glutamate plays a major role in numerous physiological functions, such as learning and memory but also sensory perception, development of synaptic plasticity, motor control, respiration and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptor channels (iGluRs), namely the NMDA, AMPA and kainate receptors which are responsible for fast excitatory transmission (Nakanishi et al., (1998) Brain Res. Rev., 26:230-235).

In addition, glutamate activates metabotropic glutamate receptors (mGluRs) which have a more modulatory role that contributes to the fine-tuning of synaptic efficacy.

The mGluRs are G protein-coupled receptors (GPCRs) with seven-transmembrane spanning domains and belong to GPCR family 3 along with the calcium-sensing, GABAb and pheromone receptors.

The mGluR family is composed of eight members. They are classified into three groups (group I comprising mGluR$_1$ and mGluR$_5$; group II comprising mGluR$_2$ and mGluR$_3$; group III comprising mGluR$_4$, mGluR$_6$, mGluR$_7$ and mGluR$_8$) according to sequence homology, pharmacological profile and nature of intracellular signalling cascades activated (Schoepp et al., (1999) Neuropharmacology, 38:1431-1476).

Glutamate activates the mGluRs through binding to the large extracellular amino-terminal domain of the receptor, herein called the orthosteric binding site. This activation induces a conformational change of the receptor which results in the activation of the G-protein and intracellular signalling pathways.

In the central nervous system, mGluR$_4$ receptors are expressed most intensely in the cerebellar cortex, basal ganglia, sensory relay nuclei of the thalamus and hippocampus (Bradley et al., (1999) Journal of Comparative Neurology, 407:33-46; Corti et al., (2002) Neuroscience, 110:403-420). The mGluR$_4$ subtype is negatively coupled to adenylate cyclase via activation of the Gαd/o protein, is expressed primarily on presynaptic terminals, functioning as an autoreceptor or heteroceptor and activation of mGluR$_4$ leads to decreases in transmitter release from presynaptic terminals (Corti et al., (2002) Neuroscience, 110:403-420; Millan et al., (2002) Journal of Biological Chemistry, 277: 47796-47803; Valenti et al., (2003) Journal of Neuroscience, 23:7218-7226).

Orthosteric agonists of mGluR$_4$ are not selective and activate the other Group III mGluRs (Schoepp et al., (1999) Neuropharmacology, 38:1431-1476). The Group III orthosteric agonist L-AP4 (L-2-amino-4-phosphonobutyrate) was able to reduce motor deficits in animal models of Parkinson's disease (Valenti et al., (2003) J. Neurosci., 23:7218-7226) and decrease excitotoxicity (Bruno et al., (2000) J. Neurosci., 20; 6413-6420) and these effects appear to be mediated through mGluR$_4$ (Marino et al., (2005) Curr. Topics Med. Chem., 5:885-895). In addition to L-AP4, ACPT-1, another selective group III mGluR agonist has been shown to caused a dose and structure-dependent decrease in haloperidol-induced catalepsy and attenuated haloperidol-increased Proenkephalin mRNA expression in the striatum (Konieczny et al., (2007) Neuroscience, 145: 611-620). Furthermore, Lopez et al. (2007, J. Neuroscience, 27:6701-6711) have shown that bilateral infusions of ACPT-I or L-AP4 into the globus pallidus fully reversed the severe akinetic deficits produced by 6-hydroxydopamine lesions of nigrostriatal dopamine neurons in a reaction-time task without affecting the performance of controls. In addition, the reversal of haloperidol-induced catalepsy by intrapallidal ACPT-1 was prevented by concomitant administration of a selective group III receptor antagonist (RS)-alpha-cyclopropyl-4-phosphonophenylglycine. The opposite effects produced by group III mGluR activation in the SNr strongly suggest a role of mGluR$_4$ rather than others mGluR receptor sub-types in normalizing basal ganglia activity (Lopez et al. 2007).

These results suggest that, among mGluR subtypes, mGluR$_4$ is believed to be the most interesting novel drug target for the treatment of Parkinson's disease (for a review see Conn et al., (2005) Nature Review Neuroscience, 6:787-798).

Symptoms of Parkinson's disease appear to be due to an imbalance in the direct and indirect output pathways of the basal ganglia, and reduction of transmission at the inhibitory GABAergic striato-pallidal synapse in the indirect pathway may result in alleviation of these symptoms (Marino et al., (2002) Amino Acids, 23:185-191).

mGluR$_4$ is more abundant in striato-pallidal synapses than in striato-nigral synapses, and its localization suggests function as a presynaptic heteroreceptor on GABAergic neurons (Bradley et al., (1999) Journal of Comparative Neurology, 407:33-46) suggesting that selective activation or positive modulation of mGluR$_4$ would decrease GABA release in this synapse thereby decreasing output of the indirect pathway and reducing or eliminating the Parkinson's disease symptoms. Classical treatment of Parkinsonism typically involves the use of levodopa combined with carbidopa (SINEMETT™) or benserazide (MADOPAR™). Dopamine agonists such as bromocriptine (PARLODEL™), lisuride and pergolide (CELANCE™) act directly on dopamine receptors and are also used for the treatment of Parkinsonism. These molecules have the same side-effect profile as levodopa.

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for mGluR$_1$, mGluR$_2$, mGluR$_4$, mGluR$_5$, mGluR$_7$ and mGluR$_8$ (Knoflach F. et al. (2001) Proc. Natl. Acad. Sci. USA, 98:13402-13407; Johnson M. P. et al., (2002) Neuropharmacology, 43:799-808; O'Brien J. A. et al., (2003) Mol. Pharmacol., 64:731-740; Johnson M. P. et al., (2003) J. Med. Chem., 46:3189-3192; Marino M. J. et al., (2003) Proc. Natl. Acad. Sci. USA, 100:13668-13673; Mitsukawa K. et al., (2005) Proc. Natl. Acad. Sci. USA, 102(51):18712-18717; Wilson J. et al., (2005) Neuropharmacology, 49:278; for a review see Mutel V., (2002) Expert Opin. Ther. Patents, 12:1-8; Kew J. N., (2004) Pharmacol. Ther., 104(3):233-244; Johnson M. P. et al., (2004) Biochem. Soc. Trans., 32:881-887; recently Ritzen A., Mathiesen, J. M. and Thomsen C., (2005) Basic Clin. Pharmacol. Toxicol., 97:202-213).

In particular molecules have been described as mGluR$_4$ positive allosteric modulators (Maj et al., (2003) Neuropharmacology, 45:895-906; Mathiesen et al., (2003) British Journal of Pharmacology, 138:1026-1030). It has been demonstrated that such molecules have been characterized in in vitro systems as well as in rat brain slices where they potentiated the effect of L-AP4 in inhibiting transmission at the striatopallidal synapse. These compounds do not activate the receptor by themselves (Marino et al., (2003) Proc. Nat. Acad. Sci. USA, 100:13668-13673). Rather, they enable the receptor to produce a maximal response to a concentration of glutamate or the Group III orthosteric agonist L-AP4 which by itself induces a minimal response.

PHCCC (N-phenyl-7-(hydroxyimino)cyclopropa[b] chromen-1a-carboxamide), a positive allosteric modulator of mGluR$_4$ not active on other mGluRs (Maj et al., (2003) Neuropharmacology, 45:895-906), has been shown to be efficacious in animal models of Parkinson's disease thus representing a potential novel therapeutic approach for Parkinson's disease as well as for other motor disorders and disturbances (Marino et al., (2003) Proc. Nat. Acad. Sci. USA, 100:13668-13673), neurodegeneration in Parkinson's disease (Marino et al., (2005) Curr. Topics Med. Chem., 5:885-895; Valenti et al., (2005) J. Pharmacol. Exp. Ther., 313:1296-1304; Vernon et al., (2005) Eur. J. Neurosci., 22:1799-1806, Battaglia et al., (2006) J. Neurosci., 26:7222-7229), and neurodegeneration in Alzheimer's disease or due to ischemic or traumatic insult (Maj et al., (2003) Neuropharmacology, 45:895-906).

PHCCC also has been shown to be active in an animal model of anxiety (Stachowicz et al., (2004) Eur. J. Pharmacol., 498:153-156). Previously, ACPT-1 has been shown to produce a dose-dependent anti-conflict effect after intrahippocampal administration and anti-depressant-like effects in rats after intracerebroventricular administration (Tatarczynska et al., (2002) Pol. J. Pharmacol., 54(6):707-710). More recently, ACPT-1 has also been shown to have anxiolytic-like effects in the stress-induced hyperthermia, in the elevated-plus maze in mice and in the Vogel conflict test in rats when injected intraperitoneally (Stachowicz et al., (2009) Neuropharmacology, 57(3): 227-234).

Activation of mGluR$_4$ receptors which are expressed in α- and F-cells in the islets of Langerhans inhibits glucagon secretion. Molecules which activate or potentiate the agonist activity of these receptors may be an effective treatment for hyperglycemia, one of the symptoms of type 2 diabetes (Uehara et al., (2004) Diabetes, 53:998-1006).

The β-chemokine RANTES is importantly involved in neuronal inflammation and has been implicated in the pathophysiology of multiple sclerosis. Activation of Group III mGluRs with L-AP4 reduced the synthesis and release of RANTES in wild-type cultured astrocytes, whereas the ability of L-AP4 to inhibit RANTES was greatly decreased in astrocyte cultures from mGluR$_4$ knockout mice (Besong et al., (2002) Journal of Neuroscience, 22:5403-5411). These data suggest that positive allosteric modulators of mGluR$_4$ may be an effective treatment for neuroinflammatory disorders of the central nervous system, including multiple sclerosis and related disorders.

Two different variants of the mGluR$_4$ receptor are expressed in taste tissues and may function as receptors for the umami taste sensation (Monastyrskaia et al., (1999) Br. J. Pharmacol., 128:1027-1034; Toyono et al., (2002) Arch. Histol. Cytol., 65:91-96). Thus positive allosteric modulators of mGluR$_4$ may be useful as taste agents, flavour agents, flavour enhancing agents or food additives.

There is anatomical evidence that the majority of vagal afferents innervating gastric muscle express group III mGluRs (mGluR$_4$, mGluR$_6$, mGluR$_7$ and mGluR$_8$) and actively transport receptors to their peripheral endings (Page et al., (2005) Gastroenterology, 128:402-10). Recently, it was shown that the activation of peripheral group III mGluRs inhibited vagal afferents mechanosensitivity in vitro which translates into reduced triggering of transient lower esophageal sphincter relaxations and gastroesophageal reflux in vivo (Young et al., (2008) Neuropharmacol, 54:965-975). Labelling for mGluR$_4$ and mGluR$_8$ was abundant in gastric vagal afferents in the nodose ganglion, at their termination sites in the nucleus tractus solitarius and in gastric vagal motoneurons. These data suggest that positive allosteric modulators of mGluR$_4$ may be an effective treatment for gastroesophageal reflux disease (GERD) and lower esophageal disorders and gastro-intestinal disorders.

International patent publication WO2005/007096 has described mGluR$_4$ receptor positive allosteric modulator useful, alone or in combination with a neuroleptic agent, for treating or preventing movement disorders. However, none of the specifically disclosed compounds are structurally related to the compounds of the invention.

Recently, new mGluR$_4$ receptor positive allosteric modulators have been described: pyrazolo[3,4-d]pyrimidine derivatives (Niswender et al., (2008) Bioorganic & Medicinal Chemistry Letters, 18(20):5626-5630), functionalized benzylidene hydrazinyl-3-methylquinazoline and bis-2,3-dihydroquinazolin-4(1H)-one (Williams et al., (2009) Bioorganic & Medicinal Chemistry Letters, 19:962-966) and heterobiarylamides (Engers et al, (2009) Journal of Medicinal Chemistry, 52 (14), 4115-4118). Niswender et al., described (±)-cis-2-(3,5-dichlorophenylcarbamoyl)cyclohexane carboxylic acid (2008) Molecular Pharmacology, 74(5):1345-1358), as a positive allosteric modulator of mGluR$_4$ also having agonist activity. This moderately active molecule has demonstrated evidence of efficacy following icv injection in rat models of Parkinson's disease. International patent publications WO2009/010454 and WO2009/010455 have mentioned amido derivatives and novel heteroaromatic derivatives, respectively, as positive allosteric modulators of metabotropic glutamate receptors. The subject of the latter case has been examined in the following article East Stephen P. et al., (2010) Expert Opin. Ther. Patents, 20 (3) 441-445. Finally, Williams R. et al., described in (2010) ACS Chemical Neuroscience, 1(6): 411-419, the "Re-exploration of the PHCCC scaffold".

International patent publication WO2010/079238 has described novel tricyclic heteroaromatic derivatives and their use as positive allosteric modulators of mGluRs. More recently, a review on recent progress on the identification of metabotropic glutamate 4 receptor ligands and their potential utility as CNS therapeutics (Robichaud A. et al., (14 Jun. 2011) ACS Chemical Neuroscience, DOI: 10.1021/cn200043e, http://pubs.acs.org) has cited some of the examples described in the WO2010/079238 patent application; Hong S.-P et al, (20 Jun. 2011) J. Med. Chem., DOI: 10.1021/jm200290z, http://pubs.acs.org) have described tricyclic thiazolopyrazole derivatives as metabotropic glutamate receptor 4 positive allosteric modulators.

The present inventors have discovered novel thiazole compounds of general Formula (I) which, surprisingly, show potent activity and selectivity on the mGluR$_4$ receptor. The compounds of the invention demonstrate advantageous properties over compounds of the prior art. Improvements have been observed in one or more of the following characteristics of the compounds of the invention: the potency on the target, the selectivity for the target, the bioavailability, the brain penetration, and the activity in behavioural models.

Such aminothiazole derivatives are useful for treating or preventing a condition in a mammal, including a human, the treatment or prevention of which is affected or facilitated by the neuromodulatory effect of mGluR$_4$ modulators. In the case of the treatment of movement disorders such as Parkinson's disease, the compounds of the invention can be used alone or in combination with an agent selected from the group consisting of: levodopa, levodopa with a selective extracerebral decarboxylase inhibitor, carbidopa, entacapone, a COMT inhibitor, a dopamine agonist, an anticholinergic, a cholinergic agonist, a butyrophenone neuroleptic agent, a diphenylbutylpiperidine neuroleptic agent, a heterocyclic dibenzazepine neuroleptic agent, an indolone neuroleptic agent, a phenothiazine neuroleptic agent, a thioxanthene neuroleptic agent, an NMDA receptor antagonist, an MAO-B inhibitor, an mGluR$_5$ antagonist or an A$_{2A}$ antagonist.

DETAILED DESCRIPTION OF THE INVENTION

The invention relates to compounds having metabotropic glutamate receptor 4 modulator activity. In its most general compound aspect, the present invention provides a compound according to Formula (I),

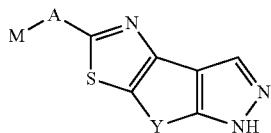

a pharmaceutically acceptable acid or base addition salt thereof, a stereochemically isomeric form thereof and an N-oxide form thereof, wherein:

M is an optionally substituted heteroaryl;
A is NH or O;
Y is selected from the group of —CO—CR$^1$R$^2$—NR$^5$— and —CR$^1$R$^2$—CR$^3$R$^4$—NR$^5$—;
R$^1$, R$^2$, R$^3$ and R$^4$ are each independently selected from the group of hydrogen, halogen, —CN, —CF$_3$ or an optionally substituted radical selected from the group of —(C$_1$-C$_6$)alkyl, —(C$_1$-C$_6$)haloalkyl, —(C$_3$-C$_7$)cycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —O—(C$_0$-C$_6$)alkyl, —N—((C$_0$-C$_6$)alkyl)$_2$, —(C$_1$-C$_6$)alkyl-O—(C$_0$-C$_6$)alkyl, and —(C$_1$-C$_6$)alkyl-N—((C$_0$-C$_6$)alkyl)$_2$;
Any two radicals of R (R$^1$, R$^2$, R$^3$ and R$^4$) may be taken together to form an optionally substituted 3 to 10 membered carbocyclic or heterocyclic ring; and
R$^5$ is selected from the group of hydrogen or an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_1$-C$_6$)haloalkyl, —(C$_1$-C$_6$)alkylene-(C$_3$-C$_7$)halocycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —(C$_2$-C$_6$)alkyl-O—(C$_0$-C$_6$)alkyl, and —(C$_2$-C$_6$)alkyl-N—((C$_0$-C$_6$)alkyl)$_2$.

In a more preferred aspect of Formula (I), the invention provides a compound according to Formula (II):

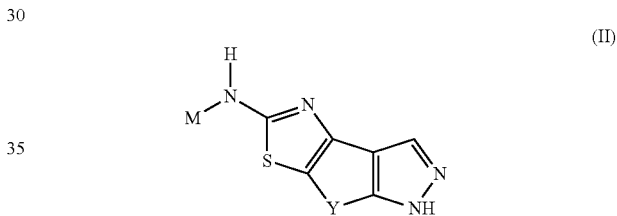

a pharmaceutically acceptable acid or base addition salt thereof, a stereochemically isomeric form thereof and an N-oxide form thereof.

In a more preferred aspect of Formula (II), the invention provides a compound according to Formula (III):

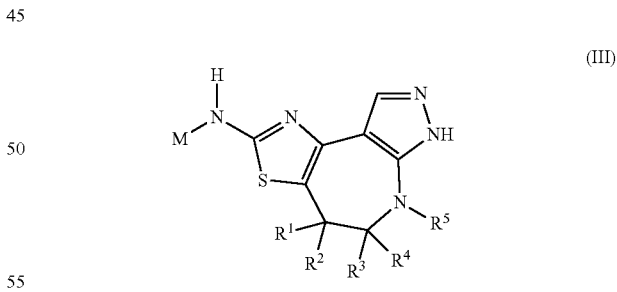

R$^1$, R$^2$, R$^3$ or R$^4$ are each independently selected from the group of hydrogen, halogen, —CN, —CF$_3$ or an optionally substituted radical selected from the group of —(C$_1$-C$_6$)alkyl, —(C$_1$-C$_6$)haloalkyl, —(C$_3$-C$_7$)cycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —O—(C$_0$-C$_6$)alkyl, —N—((C$_0$-C$_6$)alkyl)$_2$, —(C$_1$-C$_6$)alkyl-O—(C$_0$-C$_6$)alkyl, and —(C$_1$-C$_6$)alkyl-N—((C$_0$-C$_6$)alkyl)$_2$;
Any two radicals of R (R$^1$, R$^2$, R$^3$ or R$^4$) may be taken together to form an optionally substituted 3 to 10 membered carbocyclic or heterocyclic ring; and $R^5$ is selected from the group of hydrogen or an optionally substituted radical selected from the group of —($C_1$-$C_6$)alkyl, —($C_1$-$C_6$)haloalkyl, —($C_3$-$C_7$)cycloalkyl, —($C_1$-$C_6$)alkylene-($C_1$-$C_6$)haloalkyl, —($C_1$-$C_6$)alkylene-($C_3$-$C_7$)halocycloalkyl, aryl, heteroaryl, heterocycle, —($C_1$-$C_6$)alkylene-aryl, —($C_1$-$C_6$)alkylene-heteroaryl, —($C_1$-$C_6$)alkylene-heterocycle, —($C_1$-$C_6$)alkylene-($C_3$-$C_7$)cycloalkyl, —($C_2$-$C_6$)alkyl-O—($C_0$-$C_6$)alkyl, and —($C_2$-$C_6$)alkyl-N—(($C_0$-$C_6$)alkyl)$_2$.

In a more preferred aspect of Formula (III), the invention provides a compound wherein:
$R^1$, $R^2$, $R^3$ or $R^4$ are each independently selected from the group of hydrogen, halogen, —CN, —$CF_3$ or an optionally substituted radical selected from the group of —($C_1$-$C_6$)alkyl, —($C_1$-$C_6$)haloalkyl, —($C_3$-$C_7$)cycloalkyl, aryl, heteroaryl, heterocycle, —($C_1$-$C_6$)alkylene-aryl, —($C_1$-$C_6$)alkylene-heteroaryl, —($C_1$-$C_6$)alkylene-heterocycle, —O—($C_0$-$C_6$)alkyl, —N—(($C_0$-$C_6$)alkyl)$_2$, —($C_1$-$C_6$)alkyl-O—($C_0$-$C_6$)alkyl, and —($C_1$-$C_6$)alkyl-N—(($C_0$-$C_6$)alkyl)$_2$;
Any two radicals of R ($R^1$, $R^2$, $R^3$ or $R^4$) may be taken together to form an optionally substituted 3 to 10 membered carbocyclic or heterocyclic ring; and
$R^5$ is selected from the group of hydrogen or an optionally substituted radical selected from the group of —($C_1$-$C_6$)alkyl, —($C_1$-$C_6$)haloalkyl, —($C_3$-$C_7$)cycloalkyl, —($C_1$-$C_6$)alkylene-($C_1$-$C_6$)haloalkyl, —($C_1$-$C_6$)alkylene-($C_3$-$C_7$)halocycloalkyl, aryl, heteroaryl, heterocycle, —($C_1$-$C_6$)alkylene-aryl, —($C_1$-$C_6$)alkylene-heteroaryl, —($C_1$-$C_6$)alkylene-heterocycle, —($C_2$-$C_6$)alkyl-O—($C_0$-$C_6$)alkyl, and —($C_2$-$C_6$)alkyl-N—(($C_0$-$C_6$)alkyl)$_2$.

In a more preferred aspect of Formula (III), the invention provides a compound wherein:
M is an optionally substituted pyridinyl, pyrimidinyl, thiadiazolyl, triazinyl, thiazolyl and oxadiazolyl;
$R^1$, $R^2$, $R^3$ or $R^4$ are each independently selected from the group of hydrogen and an optionally substituted —($C_1$-$C_6$)alkyl; and
$R^5$ is selected from the group of hydrogen or an optionally substituted radical selected from the group of methyl, ethyl, isopropyl, cyclobutyl, methyl-ethylene-O-methyl, tetrahydrofuranyl, methylene-amide, methylene-trifluoromethyl, methylene-cyclopropyl, methylene-cyclobutyl, methylene-cyclopentyl, methylene-cyclohexyl, methylene-phenyl, methylene-tetrahydrofuranyl, methylene-pyrazolyl, methylene-isoxazolyl, methylene-oxazolyl, methylene-triazolyl, methylene-thiazolyl, methylene-pyrrolyl, methylene-imidazolyl, methylene-pyridinyl, methylene-pyrimidinyl, methylene-piperidinyl, ethylene-OH, ethylene-O-methyl, ethylene-O-isopropyl, ethylene-methylamine, ethylene-sulfonylmethyl, ethylene-trifluoromethyl, ethylene-phenyl, ethylene-pyridinyl, ethylene-cyclopropyl and propylene-O-methyl.

In a more preferred aspect of Formula (III), the invention provides a compound wherein:
M is selected from the group of pyridinyl, pyrimidinyl, thiadiazolyl and triazinyl which can each be substituted by hydrogen, methyl, fluoro, chloro, methoxy, amino, hydroxyl, methylenehydroxy or fluoromethylene;
$R^1$, $R^2$, $R^3$ or $R^4$ are each independently selected from the group of hydrogen and an optionally substituted —($C_1$-$C_6$)alkyl; and
$R^5$ is selected from the group of hydrogen or an optionally substituted radical selected from the group of methyl, ethyl, isopropyl, cyclobutyl, methyl-ethylene-O-methyl, tetrahydrofuranyl, methylene-amide, methylene-trifluoromethyl, methylene-cyclopropyl, methylene-cyclobutyl, methylene-cyclopentyl, methylene-cyclohexyl, methylene-phenyl, methylene-tetrahydrofuranyl, methylene-pyrazolyl, methylene-isoxazolyl, methylene-oxazolyl, methylene-triazolyl, methylene-thiazolyl, methylene-pyrrolyl, methylene-imidazolyl, methylene-pyridinyl, methylene-pyrimidinyl, methylene-piperidinyl, ethylene-OH, ethylene-O-methyl, ethylene-O-isopropyl, ethylene-methylamine, ethylene-sulfonylmethyl, ethylene-trifluoromethyl, ethylene-phenyl, ethylene-pyridinyl, ethylene-cyclopropyl and propylene-O-methyl.

Particular preferred compounds of the invention are compounds as mentioned in the following list (List of Particular Preferred Compounds), as well as a pharmaceutically acceptable acid or base addition salt thereof, a stereochemically isomeric form thereof and an N-oxide form thereof:

6-Methyl-N-(4-methylpyrimidin-2-yl)-4,5,6,8-tetrahydropyrazolo[3,4-b]thiazolo[4,5-d]azepin-2-amine
N-(5-Fluoropyrimidin-2-yl)-6-methyl-4,5,6,8-tetrahydropyrazolo[3,4-b]thiazolo[4,5-d]azepin-2-amine
6-Ethyl-N-(4-methylpyrimidin-2-yl)-4,5,6,8-tetrahydropyrazolo[3,4-b]thiazolo[4,5-d]azepin-2-amine
6-(Cyclopropylmethyl)-N-(5-fluoropyrimidin-2-yl)-4,5,6,8-tetrahydropyrazolo[3,4-b]thiazolo[4,5-d]azepin-2-amine
6-Isopropyl-N-(4-methylpyrimidin-2-yl)-4,5,6,8-tetrahydropyrazolo[3,4-b]thiazolo[4,5-d]azepin-2-amine
N-(5-Fluoropyrimidin-2-yl)-6-isopropyl-4,5,6,8-tetrahydropyrazolo[3,4-b]thiazolo[4,5-d]azepin-2-amine
6-(2-Methoxyethyl)-N-(4-methylpyrimidin-2-yl)-4,5,6,8-tetrahydropyrazolo[3,4-b]thiazolo[4,5-d]azepin-2-amine
6-Methyl-N-(5-methyl-1,2,4-thiadiazol-3-yl)-4,5,6,8-tetrahydropyrazolo[3,4-b]thiazolo[4,5-d]azepin-2-amine
N-(5-Fluoro-4-methylpyrimidin-2-yl)-6-methyl-4,5,6,8-tetrahydropyrazolo[3,4-b]thiazolo[4,5-d]azepin-2-amine
N-(4-Methylpyrimidin-2-yl)-6-((tetrahydrofuran-2-yl)methyl)-4,5,6,8-tetrahydropyrazolo[3,4-b]thiazolo[4,5-d]azepin-2-amine
6-(1-Methoxypropan-2-yl)-N-(4-methylpyrimidin-2-yl)-4,5,6,8-tetrahydropyrazolo[3,4-b]thiazolo[4,5-d]azepin-2-amine
N-(5-Fluoropyrimidin-2-yl)-6-(2-methoxyethyl)-4,5,6,8-tetrahydropyrazolo[3,4-b]thiazolo[4,5-d]azepin-2-amine
6-(2-Methoxyethyl)-N-(6-methylpyridin-2-yl)-4,5,6,8-tetrahydropyrazolo[3,4-b]thiazolo[4,5-d]azepin-2-amine
N-(6-Fluoropyridin-2-yl)-6-(2-methoxyethyl)-4,5,6,8-tetrahydropyrazolo[3,4-b]thiazolo[4,5-d]azepin-2-amine
N-(5-Fluoropyrimidin-2-yl)-6-(2-methoxyethyl)-4,5,6,8-tetrahydropyrazolo[3,4-b]thiazolo[4,5-d]azepin-2-amine
6-((1-Methyl-1H-pyrazol-3-yl)methyl)-N-(4-methylpyrimidin-2-yl)-4,5,6,8-tetrahydropyrazolo[3,4-b]thiazolo[4,5-d]azepin-2-amine
N,N-Dimethyl-2-(2-(4-methylpyrimidin-2-ylamino)-4,5-dihydropyrazolo[3,4-b]thiazolo[4,5-d]azepin-6(8H)-yl)acetamide
6-(2-Methoxyethyl)-N-(4-methoxypyrimidin-2-yl)-4,5,6,8-tetrahydropyrazolo[3,4-b]thiazolo[4,5-d]azepin-2-amine
6-(2-Methoxyethyl)-N-(5-methyl-1,2,4-thiadiazol-3-yl)-4,5,6,8-tetrahydropyrazolo[3,4-b]thiazolo[4,5-d]azepin-2-amine
2-(2-(5-Fluoropyrimidin-2-ylamino)-4,5-dihydropyrazolo[3,4-b]thiazolo[4,5-d]azepin-6(8H)-yl)ethanol
$N^2$-(6-(2-Methoxyethyl)-4,5,6,8-tetrahydropyrazolo[3,4-b]thiazolo[4,5-d]azepin-2-yl) pyridine-2,6-diamine
N-(5-Fluoropyrimidin-2-yl)-6-((5-methylisoxazol-3-yl)methyl)-4,5,6,8-tetrahydropyrazolo[3,4-b]thiazolo[4,5-d]azepin-2-amine
6-((3,5-Dimethylisoxazol-4-yl)methyl)-N-(5-fluoropyrimidin-2-yl)-4,5,6,8-tetrahydropyrazolo[3,4-b]thiazolo[4,5-d]azepin-2-amine N-(5-Fluoropyrimidin-2-yl)-6-((2-isopropyloxazol-4-yl)methyl)-4,5,6,8-tetrahydropyrazolo[3,4-b]thiazolo[4,5-d]azepin-2-amine N-(5-Fluoropyrimidin-2-yl)-4,5,6,8-tetrahydropyrazolo[3,4-b]thiazolo[4,5-d]azepin-2-amine N-(5-Fluoropyrimidin-2-yl)-6-(pyridin-2-ylmethyl)-4,5,6,8-tetrahydropyrazolo[3,4-b]thiazolo[4,5-d]azepin-2-amine N-(5-Fluoropyrimidin-2-yl)-6-(pyridin-4-ylmethyl)-4,5,6,8-tetrahydropyrazolo[3,4-b]thiazolo[4,5-d]azepin-2-amine N-(5-Fluoropyrimidin-2-yl)-6-(2-(methylsulfonyl)ethyl)-4,5,6,8-tetrahydropyrazolo[3,4-b]thiazolo[4,5-d]azepin-2-amine N-(5-Fluoropyrimidin-2-yl)-6-(3,3,3-trifluoropropyl)-4,5,6,8-tetrahydropyrazolo[3,4-b]thiazolo[4,5-d]azepin-2-amine N-(5-Fluoropyrimidin-2-yl)-6-(2,2,2-trifluoroethyl)-4,5,6,7-tetrahydropyrazolo[3,4-b]thiazolo[4,5-d]azepin-2-amine N-(5-Fluoropyrimidin-2-yl)-6-(tetrahydrofuran-3-yl)-4,5,6,8-tetrahydropyrazolo[3,4-b]thiazolo[4,5-d]azepin-2-amine N-(5-Fluoropyrimidin-2-yl)-6-(2-(methylamino)ethyl)-4,5,6,8-tetrahydropyrazolo[3,4-b]thiazolo[4,5-d]azepin-2-amine N-(5-Fluoropyrimidin-2-yl)-6-(3-methoxypropyl)-4,5,6,8-tetrahydropyrazolo[3,4-b]thiazolo[4,5-d]azepin-2-amine 6-Ethyl-N-(5-fluoropyrimidin-2-yl)-4,5,6,8-tetrahydropyrazolo[3,4-b]thiazolo[4,5-d]azepin-2-amine N-(5-Fluoropyrimidin-2-yl)-6-(((3-methylisoxazol-5-yl)methyl)-4,5,6,8-tetrahydropyrazolo[3,4-b]thiazolo[4,5-d]azepin-2-amine 6-(Cyclopentylmethyl)-N-(5-fluoropyrimidin-2-yl)-4,5,6,8-tetrahydropyrazolo[3,4-b]thiazolo[4,5-d]azepin-2-amine 6-(Cyclopropylmethyl)-N-(4-methylpyrimidin-2-yl)-4,5,6,8-tetrahydropyrazolo[3,4-b]thiazolo[4,5-d]azepin-2-amine 6-(Cyclohexylmethyl)-N-(5-fluoropyrimidin-2-yl)-4,5,6,8-tetrahydropyrazolo[3,4-b]thiazolo[4,5-d]azepin-2-amine 6-(Cyclopropylmethyl)-N-(6-methylpyridin-2-yl)-4,5,6,8-tetrahydropyrazolo[3,4-b]thiazolo[4,5-d]azepin-2-amine 6-(Cyclopropylmethyl)-N-(6-fluoropyridin-2-yl)-4,5,6,8-tetrahydropyrazolo[3,4-b]thiazolo[4,5-d]azepin-2-amine 6-((5-Chloropyridin-2-yl)methyl)-N-(5-fluoropyrimidin-2-yl)-4,5,6,8-tetrahydropyrazolo[3,4-b]thiazolo[4,5-d]azepin-2-amine N-(5-Fluoropyrimidin-2-yl)-6-(5-isopropylisoxazol-3-yl)methyl)-4,5,6,8-tetrahydropyrazolo[3,4-b]thiazolo[4,5-d]azepin-2-amine N-(5-Fluoropyrimidin-2-yl)-6-(2-isopropoxyethyl)-4,5,6,8-tetrahydropyrazolo[3,4-b]thiazolo[4,5-d]azepin-2-amine 6-(Cyclobutylmethyl)-N-(5-fluoropyrimidin-2-yl)-4,5,6,8-tetrahydropyrazolo[3,4-b]thiazolo[4,5-d]azepin-2-amine 6-Benzyl-N-(5-fluoropyrimidin-2-yl)-4,5,6,7-tetrahydropyrazolo[3,4-b]thiazolo[4,5-d]azepin-2-amine 6-((3-Methylisoxazol-5-yl)methyl)-N-(4-methylpyrimidin-2-yl)-4,5,6,8-tetrahydropyrazolo[3,4-b]thiazolo[4,5-d]azepin-2-amine N-(5-Fluoropyrimidin-2-yl)-6-((tetrahydrofuran-2-yl)methyl)-4,5,6,7-tetrahydropyrazolo[3,4-b]thiazolo[4,5-d]azepin-2-amine N-(5-Fluoropyrimidin-2-yl)-6-(pyrimidin-2-ylmethyl)-4,5,6,7-tetrahydropyrazolo[3,4-b]thiazolo[4,5-d]azepin-2-amine 2-(6-(2-Methoxyethyl)-4,5,6,7-tetrahydropyrazolo[3,4-b]thiazolo[4,5-d]azepin-2-ylamino)pyrimidin-5-ol N-(5-Fluoropyrimidin-2-yl)-6-(R)-tetrahydrofuran-2-yl)methyl)-4,5,6,7-tetrahydropyrazolo[3,4-b]thiazolo[4,5-d]azepin-2-amine N-(5-Fluoropyrimidin-2-yl)-6-((2-methyl-2H-1,2,3-triazol-4-yl)methyl)-4,5,6,7-tetrahydropyrazolo[3,4-b]thiazolo[4,5-d]azepin-2-amine (6-(6-(2-Methoxyethyl)-4,5,6,8-tetrahydropyrazolo[3,4-b]thiazolo[4,5-d]azepin-2-ylamino)pyridin-2-yl)methanol 6-(2-Methoxyethyl)-N-(2-methylpyrimidin-4-yl)-4,5,6,8-tetrahydropyrazolo[3,4-b]thiazolo[4,5-d]azepin-2-amine 6-(2-Methoxyethyl)-N-(pyrimidin-4-yl)-4,5,6,8-tetrahydropyrazolo[3,4-b]thiazolo[4,5-d]azepin-2-amine 6-((1H-Pyrazol-5-yl)methyl)-N-(5-fluoropyrimidin-2-yl)-4,5,6,8-tetrahydropyrazolo[3,4-b]thiazolo[4,5-d]azepin-2-amine 6-((4-Bromo-1H-pyrazol-5-yl)methyl)-N-(5-fluoropyrimidin-2-yl)-4,5,6,8-tetrahydropyrazolo[3,4-b]thiazolo[4,5-d]azepin-2-amine 6-(4-Chlorobenzyl)-N-(5-fluoropyrimidin-2-yl)-4,5,6,7-tetrahydropyrazolo[3,4-b]thiazolo[4,5-d]azepin-2-amine N-(5-Fluoropyrimidin-2-yl)-6-(2-methylbenzyl)-4,5,6,7-tetrahydropyrazolo[3,4-b]thiazolo[4,5-d]azepin-2-amine N-(5-Fluoropyrimidin-2-yl)-6-(3-methoxybenzyl)-4,5,6,7-tetrahydropyrazolo[3,4-b]thiazolo[4,5-d]azepin-2-amine 6-((5-Fluoropyridin-2-yl)methyl)-N-(5-fluoropyrimidin-2-yl)-4,5,6,7-tetrahydropyrazolo[3,4-b]thiazolo[4,5-d]azepin-2-amine N-(5-Fluoropyrimidin-2-yl)-6-((5-(trifluoromethyl)pyridin-2-yl)methyl)-4,5,6,7-tetrahydropyrazolo[3,4-b]thiazolo[4,5-d]azepin-2-amine N-(5-Fluoropyrimidin-2-yl)-6-((4-methylpyridin-2-yl)methyl)-4,5,6,7-tetrahydropyrazolo[3,4-b]thiazolo[4,5-d]azepin-2-amine 6-((3-Chloropyridin-2-yl)methyl)-N-(5-fluoropyrimidin-2-yl)-4,5,6,7-tetrahydropyrazolo[3,4-b]thiazolo[4,5-d]azepin-2-amine N-(5-Fluoropyrimidin-2-yl)-6-phenethyl-4,5,6,7-tetrahydropyrazolo[3,4-b]thiazolo[4,5-d]azepin-2-amine N-(3-Fluoro-6-methylpyridin-2-yl)-6-(2-methoxyethyl)-4,5,6,7-tetrahydropyrazolo[3,4-b]thiazolo[4,5-d]azepin-2-amine 6-(3-Chlorobenzyl)-N-(5-fluoropyrimidin-2-yl)-4,5,6,7-tetrahydropyrazolo[3,4-b]thiazolo[4,5-d]azepin-2-amine 4-((2-(5-Fluoropyrimidin-2-ylamino)-4,5-dihydropyrazolo[3,4-b]thiazolo[4,5-d]azepin-6(7H)-yl)methyl)benzonitrile N-(5-Fluoropyrimidin-2-yl)-6-(4-(trifluoromethyl)benzyl)-4,5,6,7-tetrahydropyrazolo[3,4-b]thiazolo[4,5-d]azepin-2-amine N-(5-Fluoropyrimidin-2-yl)-6-((6-methylpyridin-2-yl)methyl)-4,5,6,7-tetrahydropyrazolo[3,4-b]thiazolo[4,5-d]azepin-2-amine N-(5-Fluoropyrimidin-2-yl)-6-(2-(pyridin-2-yl)ethyl)-4,5,6,7-tetrahydropyrazolo[3,4-b]thiazolo[4,5-d]azepin-2-amine N-(5-Fluoropyrimidin-2-yl)-6-((1-methyl-1H-1,2,4-triazol-5-yl)methyl)-4,5,6,7-tetrahydropyrazolo[3,4-b]thiazolo[4,5-d]azepin-2-amine N-(5-Fluoropyrimidin-2-yl)-6-((1-methyl-1H-1,2,4-triazol-3-yl)methyl)-4,5,6,7-tetrahydropyrazolo[3,4-b]thiazolo[4,5-d]azepin-2-amine 6-(2-Chlorobenzyl)-N-(5-fluoropyrimidin-2-yl)-4,5,6,7-tetrahydropyrazolo[3,4-b]thiazolo[4,5-d]azepin-2-amine 6-(4-Fluorobenzyl)-N-(5-fluoropyrimidin-2-yl)-4,5,6,7-tetrahydropyrazolo[3,4-b]thiazolo[4,5-d]azepin-2-amine 6-((2-(5-Fluoropyrimidin-2-ylamino)-4,5-dihydropyrazolo [3,4-b]thiazolo[4,5-d]azepin-6(7H)-yl)methyl)nicotinonitrile N-(5-Fluoropyrimidin-2-yl)-6-((5-methoxypyridin-2-yl) methyl)-4,5,6,7-tetrahydropyrazolo[3,4-b]thiazolo[4,5-d] azepin-2-amine N-(5-Fluoropyrimidin-2-yl)-6-(piperidin-4-ylmethyl)-4,5,6, 7-tetrahydropyrazolo[3,4-b]thiazolo[4,5-d]azepin-2-amine 6-((5-Chlorothiazol-2-yl)methyl)-N-(5-fluoropyrimidin-2-yl)-4,5,6,7-tetrahydropyrazolo[3,4-b]thiazolo[4,5-d]azepin-2-amine N-(5-Fluoropyrimidin-2-yl)-6-((1-methyl-1H-imidazol-4-yl)methyl)-4,5,6,7-tetrahydropyrazolo[3,4-b]thiazolo[4, 5-d]azepin-2-amine 6-(1-(5-Chloropyridin-2-yl)ethyl)-N-(5-fluoropyrimidin-2-yl)-4,5,6,7-tetrahydropyrazolo[3,4-b]thiazolo[4,5-d]azepin-2-amine 6-Cyclobutyl-N-(5-fluoropyrimidin-2-yl)-4,5,6,7-tetrahydropyrazolo[3,4-b]thiazolo[4,5-d]azepin-2-amine N-(6-(Fluoromethyl)pyridin-2-yl)-6-(2-methoxyethyl)-4,5, 6,7-tetrahydropyrazolo[3,4-b]thiazolo[4,5-d]azepin-2-amine and N-(5-Fluoropyrimidin-2-yl)-6-(2-methoxyethyl)-4-methyl-4,5,6,7-tetrahydropyrazolo[3,4-b]thiazolo[4,5-d]azepin-2-amine.

Particularly relevant to the present invention is the tautomeric pair that exists for the pyrazole ring, illustrated below:

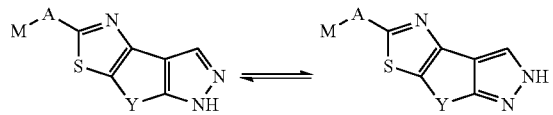

In this specification, reference to a generic formula or a compound as such indicating one tautomer is to be understood to refer to the tautomeric pair and the other tautomer thereof.

The disclosed compounds also include all pharmaceutically acceptable isotopic variations, in which at least one atom is replaced by an atom having the same atomic number, but an atomic mass different from the atomic mass usually found in nature. Examples of isotopes suitable for inclusion in the disclosed compounds include, without limitation, isotopes of hydrogen, such as $^2$H and $^3$H; isotopes of carbon, such as $^{13}$C and $^{14}$C; isotopes of nitrogen, such as $^{15}$N; isotopes of oxygen, such as $^{17}$O and $^{18}$O; isotopes of phosphorus, such as $^{32}$P and $^{33}$P; isotopes of sulfur, such as $^{35}$S; isotopes of fluorine, such as $^{18}$F; and isotopes of chlorine, such as $^{36}$Cl. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula (I) to (III) can generally be prepared by conventional techniques known to those skilled in the art or by processes analogous to those described in the accompanying Examples using appropriate isotopically-labeled reagents in place of the non-labeled reagent previously employed.

Definition of Terms

Listed below are definitions of various terms used in the specification and claims to describe the present invention.

For the avoidance of doubt it is to be understood that in this specification "$(C_1-C_6)$" means a carbon radical having 1, 2, 3, 4, 5 or 6 carbon atoms. "$(C_0-C_6)$" means a carbon radical having 0, 1, 2, 3, 4, 5 or 6 carbon atoms. In this specification "C" means a carbon atom, "N" means a nitrogen atom, "O" means an oxygen atom and "S" means a sulphur atom.

In the case where a subscript is the integer 0 (zero) the radical to which the subscript refers, indicates that the radical is absent, i.e. there is a direct bond between the radicals.

In the case where a subscript is the integer 0 (zero) and the radical to which the subscript refers is alkyl, this indicates the radical is a hydrogen atom.

In this specification, unless stated otherwise, the term "bond" refers to a saturated covalent bond. When two or more bonds are adjacent to one another, they are assumed to be equal to one bond. For example, a radical -A-B—, wherein both A and B may be a bond, the radical is depicting a single bond.

In this specification, unless stated otherwise, the term "alkyl" includes both straight and branched chain alkyl radicals and may be methyl, ethyl, n-propyl, i-propyl, n-butyl, butyl, s-butyl, t-butyl, n-pentyl, i-pentyl, t-pentyl, neopentyl, n-hexyl, i-hexyl or t-hexyl. The term "$(C_0-C_3)$alkyl" refers to an alkyl radical having 0, 1, 2 or 3 carbon atoms and may be methyl, ethyl, n-propyl and i-propyl.

In this specification, unless stated otherwise, the term "alkylene" includes both straight and branched difunctional saturated hydrocarbon radicals and may be methylene, ethylene, n-propylene, i-propylene, n-butylene, i-butylene, s-butylene, t-butylene, n-pentylene, i-pentylene, t-pentylene, neo-pentylene, n-hexylene, i-hexylene or t-hexylene.

In this specification, unless stated otherwise, the term "cycloalkyl" refers to an optionally substituted carbocycle containing no heteroatoms, including mono-, bi-, and tricyclic saturated carbocycles, as well as fused ring systems. Such fused ring systems can include one ring that is partially or fully unsaturated such as a benzene ring to form fused ring systems such as benzo-fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl and 1,2,3,4-tetrahydronaphthalene and the like. The term "$(C_3-C_7)$cycloalkyl" may be cyclopropyl, cyclobutyl, cyclopentyl, cyclohexyl, cycloheptyl and the like.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl, indenyl and the like.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thienyl, pyridinyl, thiazolyl, isothiazolyl, furyl, pyrrolyl, triazolyl, imidazolyl, triazinyl, oxadiazolyl, oxazolyl, isoxazolyl, pyrazolyl, imidazolonyl, oxazolonyl, thiazolonyl, tetrazolyl, thiadiazolyl, benzoimidazolyl, benzooxazolyl, benzothiazolyl, tetrahydrotriazolopyridinyl, tetrahydrotriazolopyrimidinyl, benzofuryl, benzothiophenyl, thionaphthyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridinyl, oxazolopyridinyl, thiazolopyridinyl, imidazopyridazinyl, oxazolopyridazinyl, thiazolopyridazinyl, cynnolyl, pteridinyl, furazanyl, benzotriazolyl, pyrazolopyridinyl and purinyl.

In this specification, unless stated otherwise, the term "alkylene-aryl", "alkylene-heteroaryl" and "alkylene-cycloalkyl" refers respectively to a substituent that is attached via the alkyl radical to an aryl, heteroaryl or cycloalkyl radical, respectively. The term "$(C_1-C_6)$alkylene-aryl" includes aryl-$C_1$-$C_6$-alkyl radicals such as benzyl, 1-phenylethyl, 2-phenylethyl, 1-phenylpropyl, 2-phenylpropyl, 3-phenylpropyl, 1-naphthylmethyl and 2-naphthylmethyl. The term "$(C_1-C_6)$alkylene-heteroaryl" includes heteroaryl-$C_1$-$C_6$-alkyl radicals, wherein examples of heteroaryl are the same as those illustrated in the above definition, such as 2-furylmethyl, 3-furylmethyl, 2-thienylmethyl, 3-thienylmethyl, 1-imidazolylmethyl, 2-imidazolylmethyl, 3-imidazolylmethyl, 2-oxazolylmethyl, 3-oxazolylmethyl, 2-thiazolylmethyl, 3-thiazolylmethyl, 2-pyridinylmethyl, 3-pyridinylmethyl, 4-pyridinylmethyl, 1-quinolylmethyl or the like.

In this specification, unless stated otherwise, the term "heterocycle" refers to an optionally substituted, monocyclic or bicyclic saturated, partially saturated or unsaturated ring system containing at least one heteroatom selected independently from N, O and S.

In this specification, unless stated otherwise, a 5- or 6-membered ring containing one or more atoms independently selected from C, N, O and S, includes aromatic and heteroaromatic rings as well as carbocyclic and heterocyclic rings which may be saturated or unsaturated. Examples of such rings may be, but are not limited to, furyl, isoxazolyl, isothiazolyl, oxazolyl, pyrazinyl, pyrazolyl, pyridazinyl, pyridinyl, pyrimidinyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, tetrahydrothiopyranyl, oxazolidinonyl, thiomorpholinyl, oxadiazolyl, thiadiazolyl, tetrazolyl, phenyl, cyclohexyl, cyclopentyl, cyclohexenyl and cyclopentenyl.

In this specification, unless stated otherwise, a 3- to 10-membered ring containing one or more atoms independently selected from C, N, O and S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, tetrahydrothiopyranyl, furyl, pyrrolyl, dihydropyrrolyl isoxazolyl, isothiazolyl, isoindolinonyl, dihydropyrrolo[1,2-b]pyrazolyl, oxazolyl, oxazolidinonyl, pyrazinyl, pyrazolyl, pyridazinyl, pyridinyl, tetrahydropyridinyl, pyrimidinyl, pyrrolyl, thiazolyl, thienyl, imidazolyl, triazolyl, phenyl, cyclopropyl, aziridinyl, cyclobutyl, azetidinyl, oxadiazolyl, thiadiazolyl, tetrazolyl, cyclopentyl, cyclopentenyl, cyclohexyl, cyclohexenyl, cycloheptyl, cycloheptenyl, cyclooctyl and cyclooctenyl.

In this specification, unless stated otherwise, the term "halo" or "halogen" may be fluoro, chloro, bromo or iodo.

In this specification, unless stated otherwise, the term "haloalkyl" means an alkyl radical as defined above, substituted with one or more halo radicals. The term "$(C_1-C_6)$haloalkyl" may include, but is not limited to, fluoromethyl, difluoromethyl, trifluoromethyl, fluoroethyl and difluoroethyl. The term "O—$C_1$-$C_6$-haloalkyl" may include, but is not limited to, fluoromethoxy, difluoromethoxy, trifluoromethoxy and fluoroethoxy.

In this specification, unless stated otherwise, the term "haloalkylene" means an alkylene radical as defined above, substituted with one or more halo radicals. The term "$(C_1-C_6)$haloalkylene" may include, but is not limited to, fluoromethylene, difluoromethylene, fluoroethylene and difluoroethylene. The term "O—$C_1$-$C_6$-haloalkylene" may include, but is not limited to, fluoromethylenoxy, difluoromethylenoxy and fluoroethylenoxy.

In this specification, unless stated otherwise, the term "cyanoalkyl" means an alkyl radical as defined above, substituted with one or more cyano.

In this specification, unless stated otherwise, the term "optionally substituted" refers to radicals further bearing one or more substituents which may be, $(C_1-C_6)$alkyl, hydroxy, $(C_1-C_6)$alkylene-oxy, mercapto, aryl, heterocycle, heteroaryl, $(C_1-C_6)$alkylene-aryl, $(C_1-C_6)$alkylene-heterocycle, $(C_1-C_6)$alkylene-heteroaryl, halogen, trifluoromethyl, pentafluoroethyl, cyano, cyanomethyl, nitro, amino, amido, amidinyl, carboxyl, carboxamide, $(C_1-C_6)$alkylene-oxycarbonyl, carbamate, sulfonamide, ester and sulfonyl.

In this specification, unless stated otherwise, the term "solvate" refers to a complex of variable stoichiometry formed by a solute (e.g. a compound of Formula (I)) and a solvent. The solvent is a pharmaceutically acceptable solvent as preferably water; such solvent may not interfere with the biological activity of the solute.

In this specification, unless stated otherwise, the term "positive allosteric modulator of mGluR$_4$" or "allosteric modulator of mGluR$_4$" refers also to a pharmaceutically acceptable acid or base addition salt thereof, a stereochemically isomeric form thereof and an N-oxide form thereof.

Pharmaceutical Compositions

Allosteric modulators of mGluR$_4$ described herein, and the pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The allosteric modulators of mGluR$_4$ will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

The amount of allosteric modulators of mGluR$_4$, administered to the subject will depend on the type and severity of the disease or condition and on the characteristics of the subject, such as general health, age, sex, body weight and tolerance to drugs. The skilled artisan will be able to determine appropriate dosages depending on these and other factors. Effective dosages for commonly used CNS drugs are well known to the skilled person. The total daily dose usually ranges from about 0.05-2000 mg.

The present invention relates to pharmaceutical compositions which provide from about 0.01 to 1000 mg of the active ingredient per unit dose. The compositions may be administered by any suitable route. For example, orally in the form of capsules and the like, parenterally in the form of solutions for injection, topically in the form of onguents or lotions, ocularly in the form of eye-drops, rectally in the form of suppositories, intranasally or transcutaneously in the form of delivery system like patches.

For oral administration, the allosteric modulators of mGluR$_4$ thereof can be combined with a suitable solid or liquid carrier or diluent to form capsules, tablets, pills, powders, syrups, solutions, suspensions and the like.

The tablets, pills, capsules, and the like contain from about 0.01 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parenteral administration the disclosed allosteric modulators of mGluR$_4$ can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered for example, by subcutaneously implantation or by intramuscular injection. Thus, for example, as an emulsion in an acceptable oil, or ion exchange resins, or as sparingly soluble derivatives, for example, as sparingly soluble salts.

Preferably disclosed allosteric modulators of mGluR$_4$ or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Classical treatment of Parkinsonism typically involves the use of levodopa combined with carbidopa (SINEMET™) or benserazide (MADOPAR™). Dopamine agonists such as bromocriptine (PARLODEL™), lisuride and pergolide (CELANCE™) act directly on dopamine receptors and are also used for the treatment of Parkinsonism.

Methods of Synthesis

The compounds according to the invention, in particular the compounds according to the Formula (I) to (III), may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (Green T. W. and Wuts P. G. M., (1991) *Protecting Groups in Organic Synthesis*, John Wiley & Sons). These groups are removed at a convenient stage of the compound synthesis using methods that are readily apparent to those skilled in the art. The selection of process as well as the reaction conditions and order of their execution shall be consistent with the preparation of compounds of Formula (I) to (III).

The compounds according to the invention may be represented as a mixture of enantiomers, which may be resolved into the individual pure R- or S-enantiomers. If for instance, a particular enantiomer is required, it may be prepared by asymmetric synthesis or by derivation with a chiral auxiliary, where the resulting diastereomeric mixture is separated and the auxiliary group cleaved to provide the pure desired enantiomers. Alternatively, where the molecule contains a basic functional group such as an amino or an acidic functional group such as carboxyl, this resolution may be conveniently performed by fractional crystallization from various solvents as the salts of an optical active acid or by other methods known in the literature (e.g. chiral column chromatography).

Resolution of the final product, an intermediate or a starting material may be performed by any suitable method known in the art (Eliel E. L., Wilen S. H. and Mander L. N., (1984) *Stereochemistry of Organic Compounds*, Wiley-Interscience).

Many of the heterocyclic compounds of the invention can be prepared using synthetic routes well known in the art (Katrizky A. R. and Rees C. W., (1984) *Comprehensive Heterocyclic Chemistry*, Pergamon Press).

The product from the reaction can be isolated and purified by employing standard techniques, such as extraction, chromatography, crystallization and distillation.

The compounds of the invention may be prepared by general route of synthesis as disclosed in the following methods.

In one embodiment of the present invention, compounds of Formula (III) may be prepared according to the synthetic sequences illustrated in Scheme 1. Pyrazole g1 can be protected by p-methoxybenzyl, for example, using standard conditions. Then compound g2 may be hydrolyzed and the resulting carboxylic acid g3 can be transformed into the corresponding Weinreb amide g4. Functionalized pyrazole g5 can be obtained from deprotonation of pyrazole g4 using LDA as a base in THF at −78° C. followed by the addition of hexachloroethane. The subsequent chloropyrazole g5 may be substituted by primary amine to yield aminopyrazole g6 which can then be reacted with allylbromide in the presence of NaH to give the tertiary amine g7. Vinyl Grignard reagent can be added on the Weinreb amide g7 to generate the compound g8 which can undergo metathesis using Grubbs catalysts. The resulting α,β-unsaturated ketone g9 can be reduced in the presence of ammonium formate and Pd(OH)$_2$. Subsequently, ketone g10 can be transformed into bromoketone g11, which in the presence of substituted thiourea can be cyclized into an aminothiazole g12. Finally, the expected compound g13 can be obtained via deprotection in the presence of TFA or a mixture of TFA/TfOH at room temperature.

Scheme 1

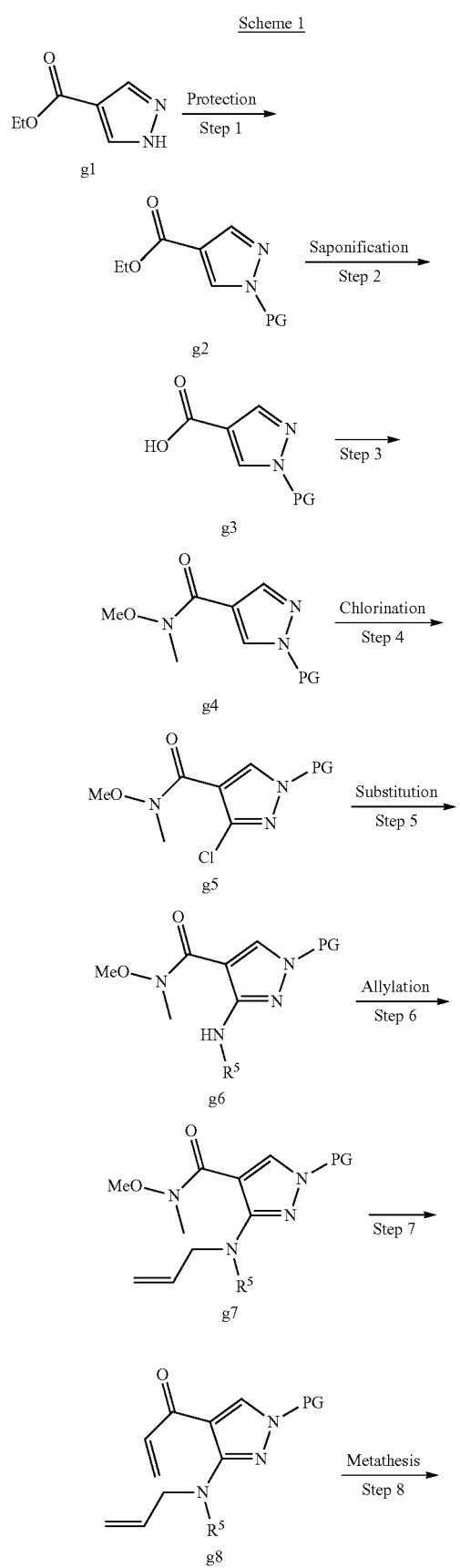

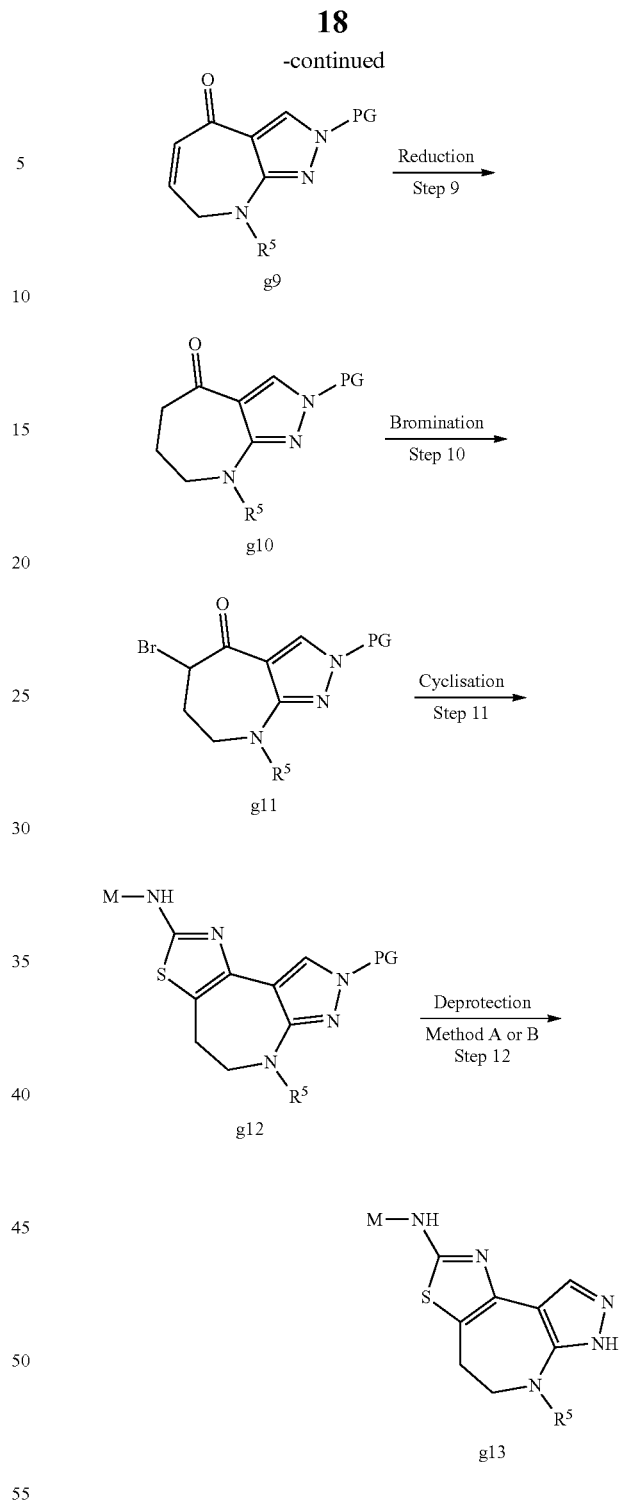

In one embodiment of the present invention, compounds of Formula (III) may be prepared according to the synthetic sequences illustrated in Scheme 2. Bromoketone g11, described above, can be submitted to cyclization in the presence of thiourea to yield aminothiazole g14. Primary amine g14 can be coupled to heteroaryl halide M-X, using Buchwald conditions with Pd(OAc)$_2$ and Josiphos ligand, under microwave conditions, to yield compound g12 which can be finally deprotected under acidic conditions as described above to give compound g13.

Scheme 2

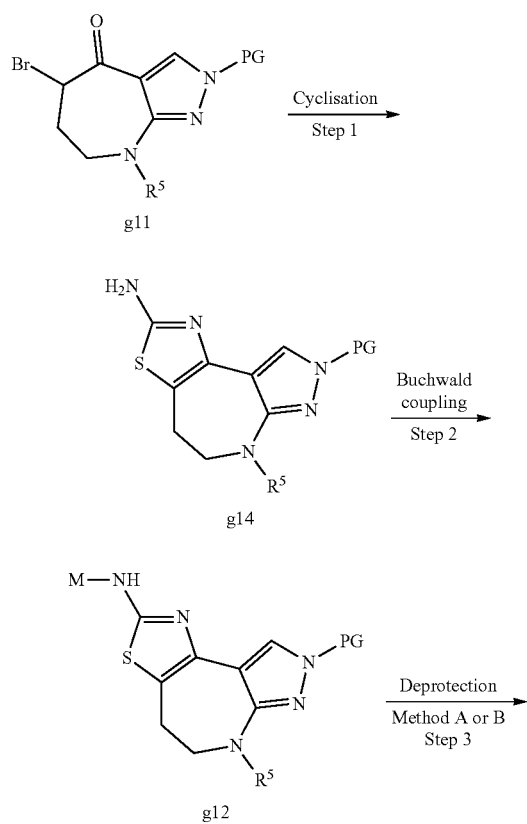

In one embodiment of the present invention, compounds of Formula (III) may be prepared according to the synthetic sequences illustrated in Scheme 3. Pyrazole g14 described above can be deprotected under acidic conditions and can be submitted to Buchwald coupling in the presence of heteroaryl halide M-X, Pd$_2$(dba)$_3$, Xantphos and in a solvent such as toluene to yield the final compound g13.

Scheme 3

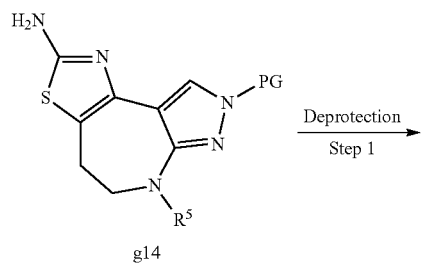

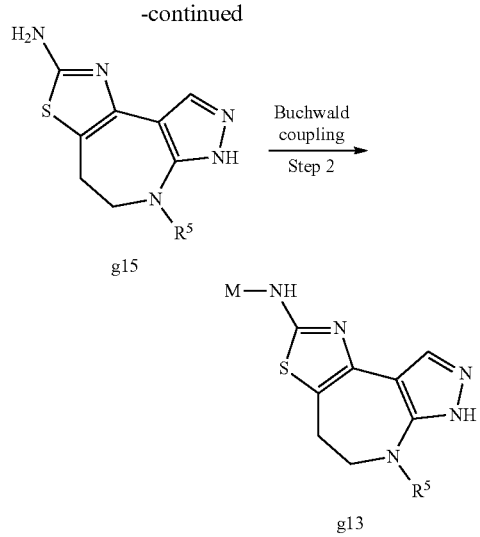

In one embodiment of the present invention, compounds of Formula (III) may be prepared according to the synthetic sequences illustrated in Scheme 4. Ketone g10 can be converted directly to the substituted aminothiazole g12 in the presence of a thiourea, diiodine and in a solvent such as pyridine. After deprotection under acidic conditions, the desired compound g13 can be obtained.

Scheme 4

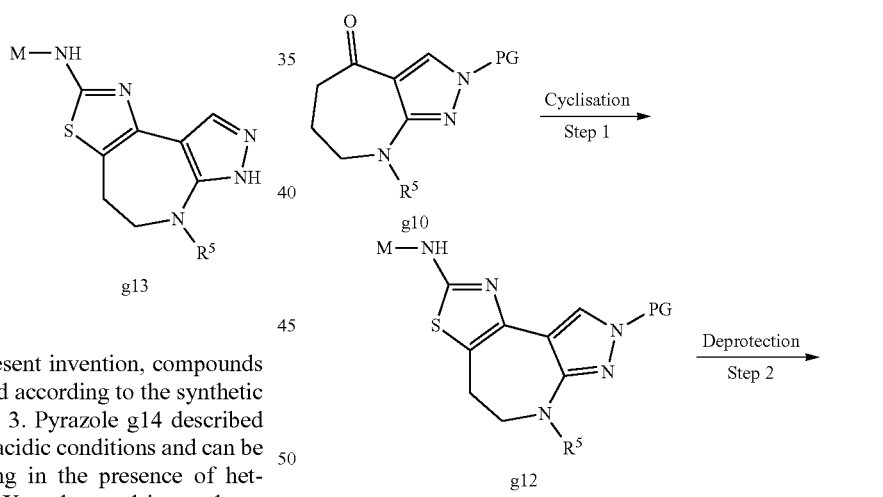

In one embodiment of the present invention, compounds of Formula (III) may be prepared according to the synthetic sequences illustrated in Scheme 5. Pyrazole g16 can be protected by p-methoxybenzyl, for example, using standard conditions. Then the primary amine g17 can be converted into tertiary amine by being submitted first to a reductive amination followed by an allylation under standard conditions known from persons skilled in the art. After saponification of g19, the carboxylic acid can be transformed into the Weinreb amide g21 which after six steps yielded the desired compound g22 as described above in Scheme 1.

In one embodiment of the present invention, compounds of Formula (III) may be prepared according to the synthetic sequences illustrated in Scheme 6. The ester g17 can be directly transformed into the Weinreb amide g23 in the presence of trimethylaluminum and N,O-dimethylhydroxylamine in a solvent such as DCM. After reductive amination followed by allylation, the tertiary amine g21 can be used as in Scheme 1 to yield the final compound g13.

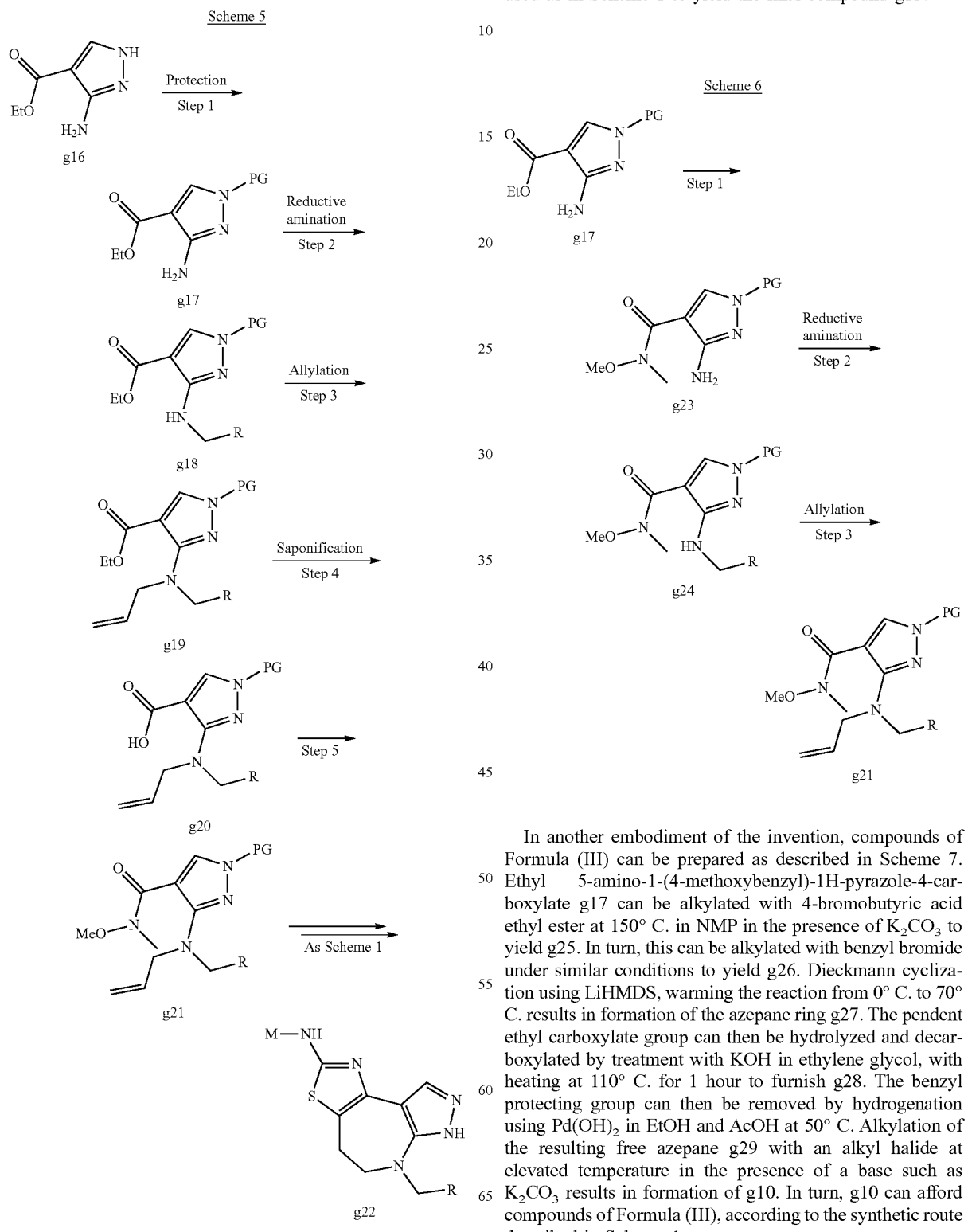

In another embodiment of the invention, compounds of Formula (III) can be prepared as described in Scheme 7. Ethyl 5-amino-1-(4-methoxybenzyl)-1H-pyrazole-4-carboxylate g17 can be alkylated with 4-bromobutyric acid ethyl ester at 150° C. in NMP in the presence of $K_2CO_3$ to yield g25. In turn, this can be alkylated with benzyl bromide under similar conditions to yield g26. Dieckmann cyclization using LiHMDS, warming the reaction from 0° C. to 70° C. results in formation of the azepane ring g27. The pendent ethyl carboxylate group can then be hydrolyzed and decarboxylated by treatment with KOH in ethylene glycol, with heating at 110° C. for 1 hour to furnish g28. The benzyl protecting group can then be removed by hydrogenation using $Pd(OH)_2$ in EtOH and AcOH at 50° C. Alkylation of the resulting free azepane g29 with an alkyl halide at elevated temperature in the presence of a base such as $K_2CO_3$ results in formation of g10. In turn, g10 can afford compounds of Formula (III), according to the synthetic route described in Scheme 1.

Scheme 7

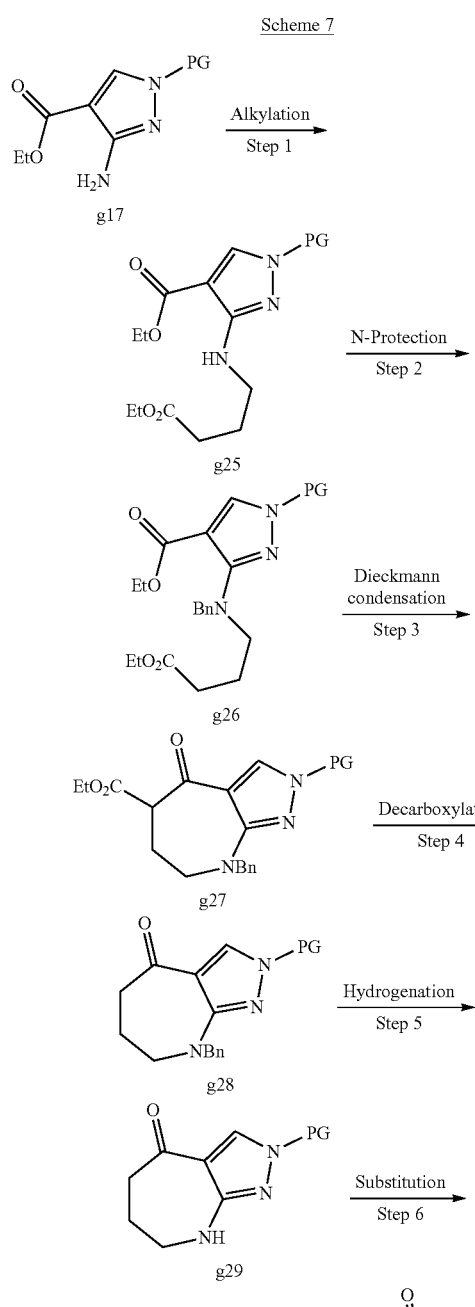

using Grubbs catalysts. The resulting α,β-unsaturated ketone g33 can be reduced and also deprotected in the presence of ammonium formate and Pd(OH)$_2$. Subsequently, the amine g29 can be functionalized by R$^5$X in the presence of different bases such as NaH, LiHMDS, KOtBu, and in a solvent such as THF to yield the compound g10. Compound g10 can then undergo Steps 10 to 12 in Scheme 1 to give the expected aminothiazole g13.

Scheme 8

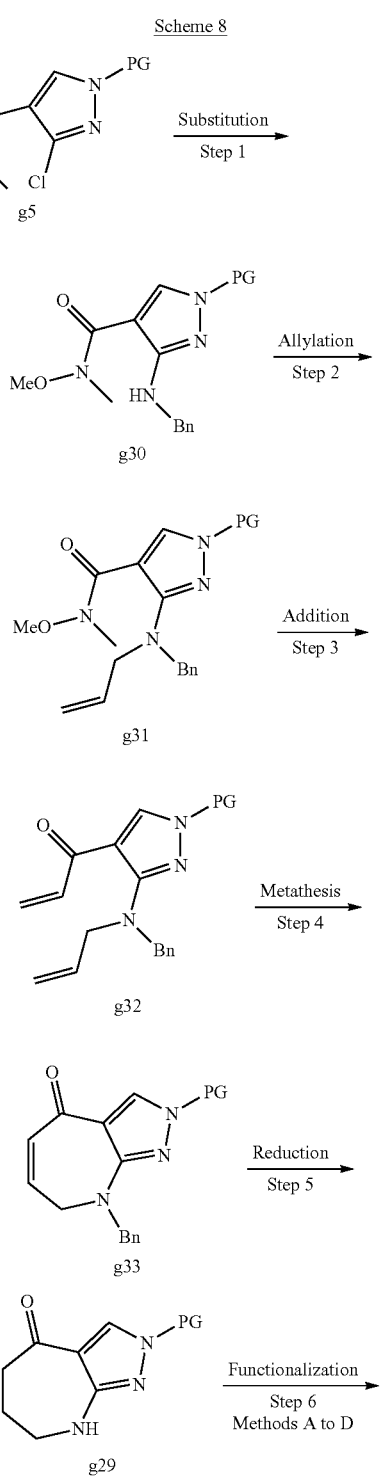

In one embodiment of the present invention, compounds of Formula (III) may be prepared according to the synthetic sequences illustrated in Scheme 8. Chloropyrazole g5 may be substituted by phenylmethanamine to yield aminopyrazole g30 which can then be reacted with allylbromide in the presence of NaH to give the tertiary amine g31. Vinyl Grignard reagent can be added on the Weinreb amide g31 to generate the compound g32 which can undergo metathesis

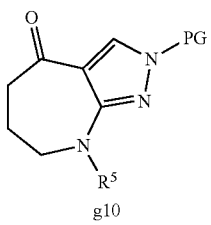

g10

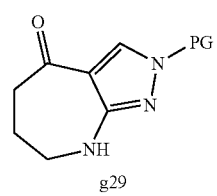

g29

In one embodiment of the present invention, compounds of Formula (III) may be prepared according to the synthetic sequences illustrated in Scheme 9. Weinreb amide g5 may be converted into ketone g34 in the presence of methylmagnesium bromide. Then the chloropyrazole g34 can be substituted by allylamine under microwave conditions followed by direct α-methylenation of the ketone moiety in the presence of formaldehyde, diisopropylammonium-2,2,2-trifluoroacetate and a catalytic amount of acid such as TFA to give the α,β-unsaturated ketone g36. As described above g36 can undergo metathesis using Grubbs catalysts, the resulting α,β-unsaturated ketone can be reduced to yield to compound g29 which can lead to aminothiazole g13 as in Scheme 1.

In one embodiment of the present invention, compounds of Formula (III) may be prepared according to the synthetic sequences illustrated in Scheme 10. The secondary amine g29 can be functionalized by ethoxy(tert-butyl)dimethylsilane in the presence of a base such as KOtBu. The ketone g38 in the presence of a thiourea and diiodine can lead to the aminothiazole g39. The TBDMS group can be gently removed in the presence of an acid such as HCl in a protic solvent such as methanol to yield the free hydroxyl function in the compound g40. Subsequently the hydroxyl function can be transformed into a good leaving group such as tosylate using standard conditions which can be displaced for example, by a sulfinate such as sodium methane sulfinate, an amine such as methanamine and the like to yield g42 or g43 respectively. After deprotection under acidic conditions, the expected compound g44 is obtained.

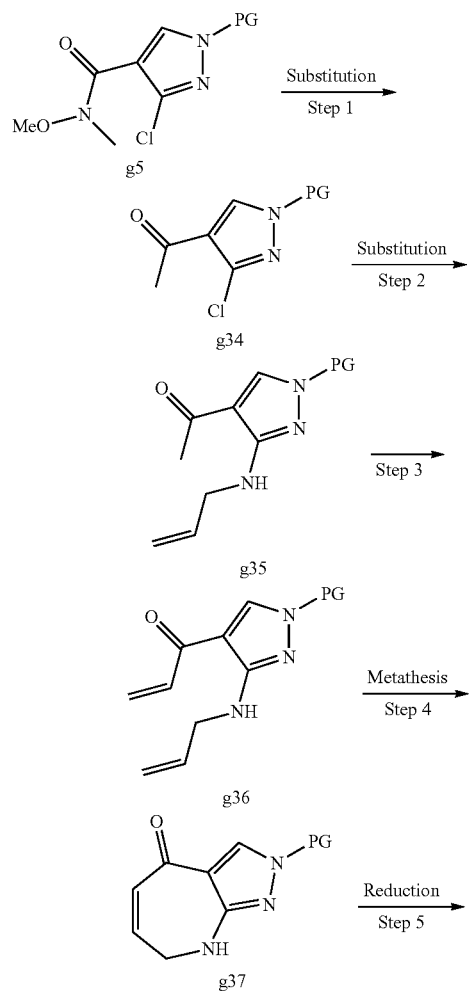

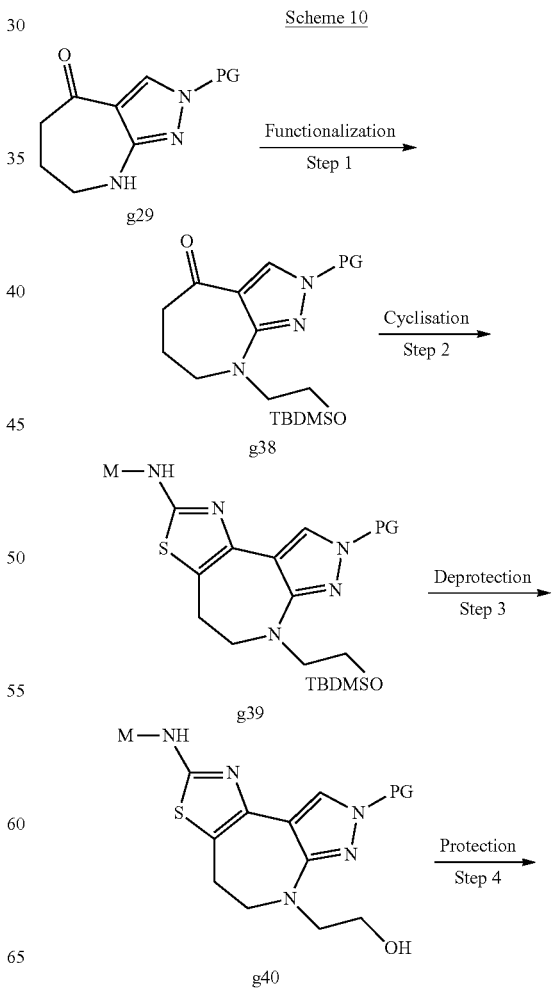

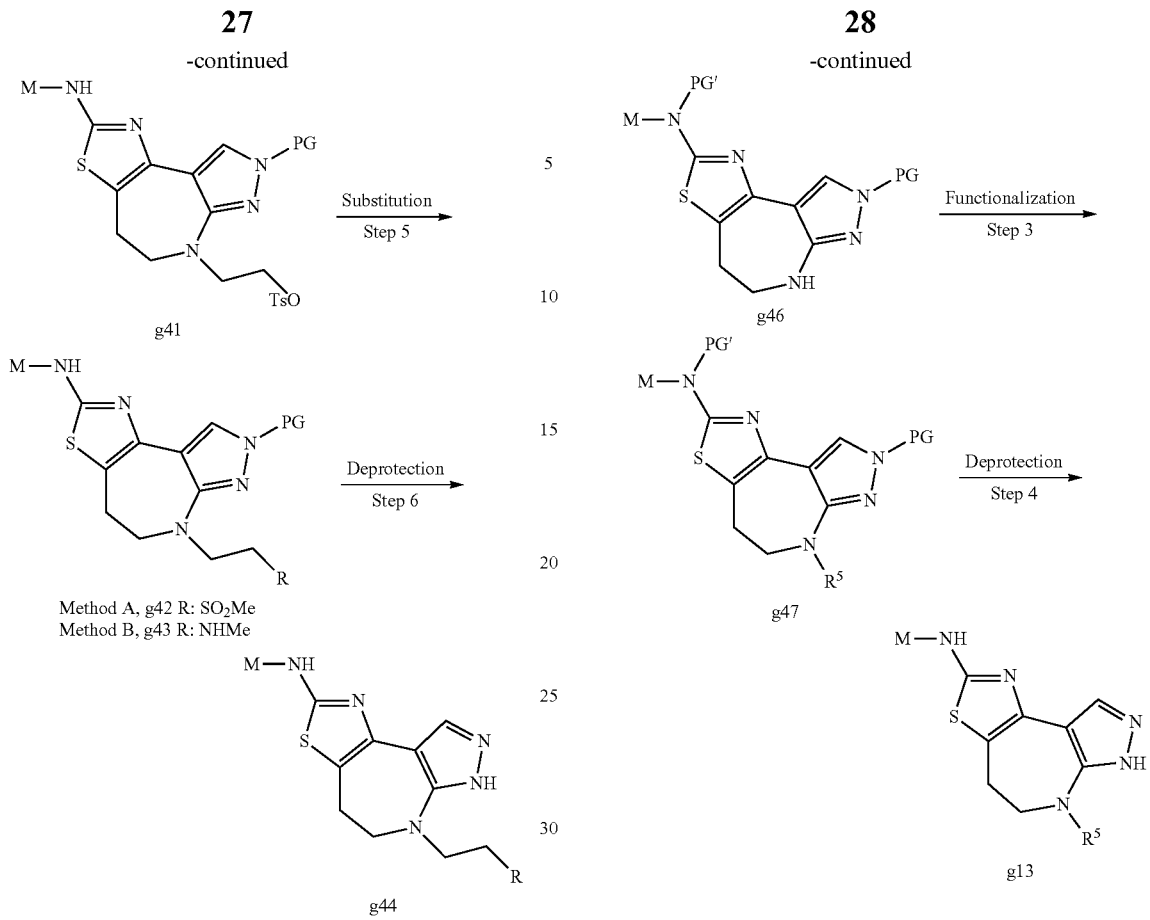

In one embodiment of the present invention, compounds of Formula (III) may be prepared according to the synthetic sequences illustrated in Scheme 11. The ketone g29 in the presence of a thiourea and diiodine can lead to the aminothiazole g45. The aminothiazole g45 can be protected selectively by p-methoxybenzyl in the presence of a base such as NaH and in a solvent such as DMF. Then the secondary amine g46 can be functionalized by methods described above and finally deprotected under acidic conditions to afford the desired compound g13.

In one embodiment of the present invention, compounds of Formula (III) may be prepared according to the synthetic sequences illustrated in Scheme 12. The ether g48 can be demethylated in the presence of BBr$_3$ using standard methods well known from persons skilled in the art to yield the hydroxy compound g49.

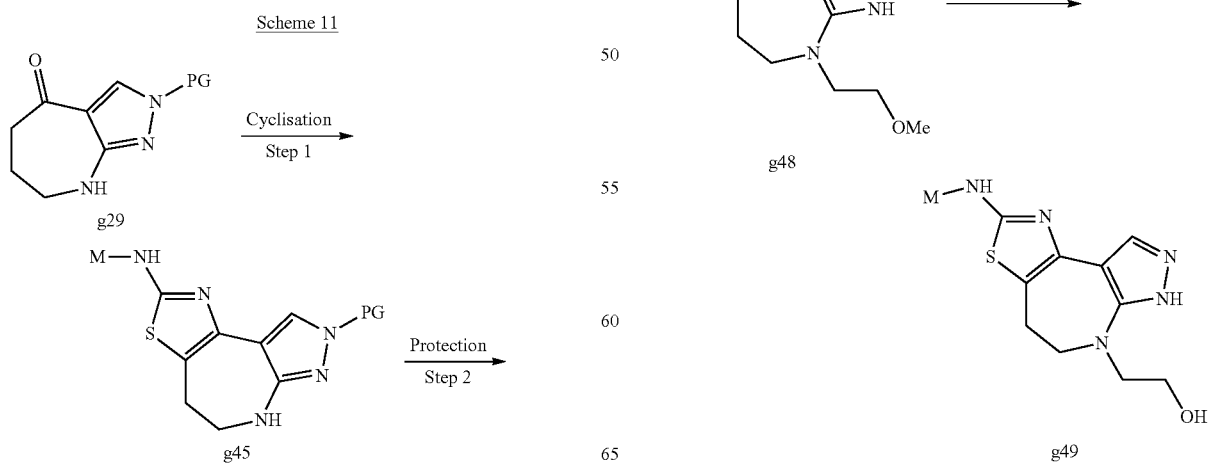

In one embodiment of the present invention, compounds of Formula (III) may be prepared according to the synthetic sequences illustrated in Scheme 13. g50 as an intermediate in the general Scheme 1 can be synthesized from the selective reduction of the double bond in the presence of hydrogen and Pd(OH)$_2$ in a solvent such as a mixture of ethanol and acetic acid.

Scheme 13

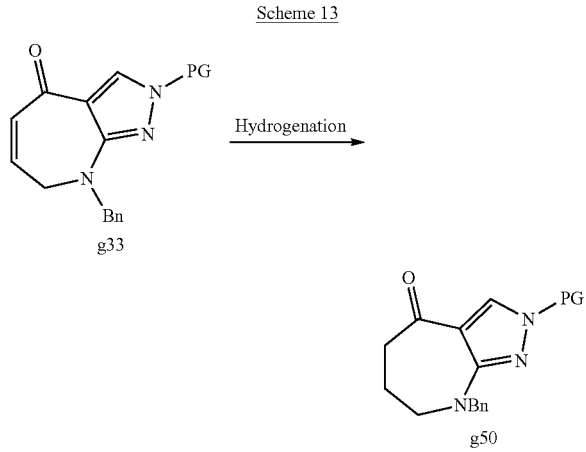

In one embodiment of the present invention, compounds of Formula (III) may be prepared according to the synthetic sequences illustrated in Scheme 14. g51 having a SEM group as protecting group can be submitted to functionalization as described above. The resulting ketone g52 in the presence of trimethylphenylammonium tribromide in a solvent such as chloroform can be α-brominated with concomitant cleavage of the SEM. Finally the α-bromoketone g53 can be transformed into aminothiazole g13 using method described above.

Scheme 14

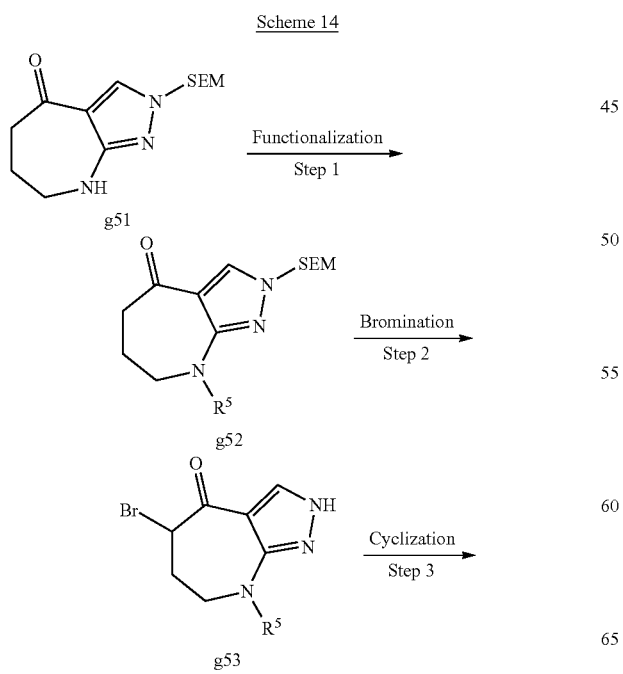

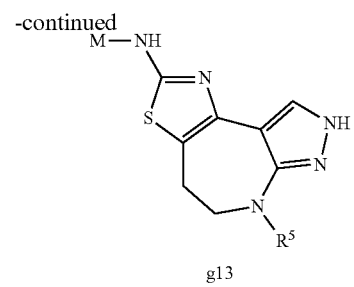

g13

In one embodiment of the present invention, compounds of Formula (III) may be prepared according to the synthetic sequences illustrated in Scheme 15. Compound g29 can be alkylated by methylene-pyridinyl in the presence of a base such as K$_2$CO$_3$ and in a solvent such as NMP, to afford compound g54. The pyridine substituent of g54 can be reduced by hydrogenation with Pd(OH)$_2$ and the resulting piperidine can be protected in situ due to the presence of Boc$_2$O. Finally, compound g55 can afford compounds of Formula (III) using method described above.

Scheme 15

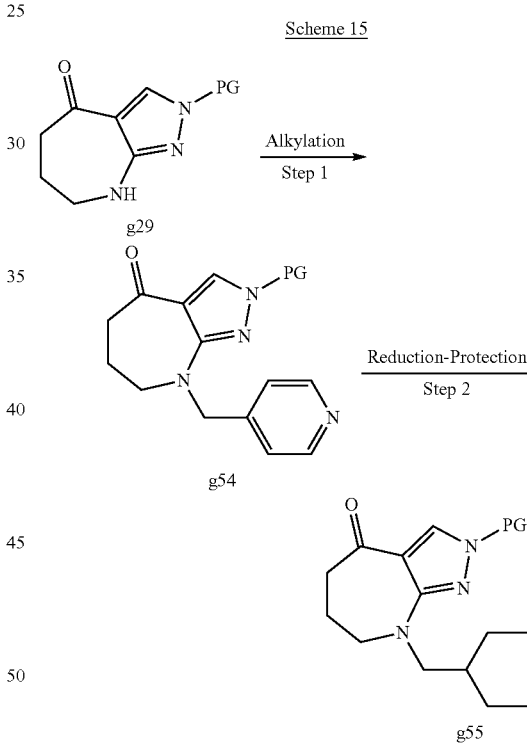

In one embodiment of the present invention, compounds of Formula (III) may be prepared according to the synthetic sequences illustrated in Scheme 16. Potassium thiocyanate can displace the halogen moiety in the α-bromoketone g11 to afford compound g56. Then under acidic condition, compound g56 can be cyclized into the 2-bromothiazole g57 in the presence of a mixture of acetic acid and hydrobromic acid. The 2-bromothiazole g57 can be coupled to heteroaryl amine M-NH$_2$, using Buchwald conditions with as a catalyst Pd$_2$(dba)$_3$ and the like, as a ligand Xantphos and the like and as a base Cs$_2$CO$_3$ to yield compound g12 which can be finally deprotected under acidic conditions as described above to give compound g13.

Scheme 16

[Structure g11: bromo-ketone pyrazolo-azepine with PG and R⁵]

→ Substitution, Step 1 →

[Structure g56: thiocyanato-ketone pyrazolo-azepine with PG and R⁵]

→ Cyclisation-Bromination, Step 2 →

[Structure g57: bromo-thiazolo-pyrazolo-azepine with PG and R⁵]

→ Buchwald coupling, Step 3 →

[Structure g12: M-NH-thiazolo-pyrazolo-azepine with PG and R⁵]

→ Deprotection, Step 4 →

[Structure g13: M-NH-thiazolo-pyrazolo-azepine with NH and R⁵]

In general, substituted thiourea M-NH—(C=S)—NH$_2$ used in Schemes 1, 4, 10, 11 and 14, are prepared according to methods known by persons skilled in the art. For example, 5-fluoropyrimidin-2-amine can be reacted with ethyl carbonisothiocyanatidate in acetonitrile, then the resulting product can be treated with ammonium formate in ammonia affording the thiourea 5-fluoropyrimidin-2-yl-NH(C=S)—NH$_2$.

EXPERIMENTAL

Unless otherwise noted, all starting materials were obtained from commercial suppliers and used without further purification.

Specifically, the following abbreviations may be used in the examples and throughout the specification.

| | |
|---|---|
| ACN (Acetonitrile) | mg (Milligrams) |
| AcOH (Acetic acid) | MgSO$_4$ (Magnesium sulfate) |
| AlMe$_3$ (Trimethylaluminium) | min (Minutes) |
| atm (Atmosphere) | mL (Milliliters) |
| BBr$_3$ (Boron tribromide) | mmol (Millimoles) |
| BnBr (Benzyl bromide) | M.p. (Melting point) |
| BuLi (Butyl lithium) | NH$_4$Cl (Ammonium chloride) |
| t-BuOH (tert-Butanol) | NaBH(OAc)$_3$ (Sodium triacetoxyborohydride) |
| CHCl$_3$ (Chloroform) | NaH (Sodium hydride) |
| CuBr$_2$ (Copper (II) bromide) | NaHCO$_3$ (Sodium bicarbonate) |
| DCE (Dichloroethane) | NaI (Sodium iodide) |
| DCM (Dichloromethane) | Na$_2$CO$_3$ (Sodium carbonate) |
| DME (Dimethoxyethane) | Na$_2$SO$_4$ (Sodium sulfate) |
| DMF (Dimethylformamide) | NMP (N-Methylpyrrolidone) |
| EtOAc (Ethyl acetate) | Pd(OAc)$_2$ (Palladium(II)acetate) |
| EtOH (Ethanol) | Pd(OH)$_2$ (Palladium(II) hydroxide) |
| Et$_2$O (Diethyl ether) | Pd$_2$(dba)$_3$ (Tris(dibenzylideneacetone)dipalladium(0)) |
| Et$_3$N (Triethylamine) | PE (Petroleum ether) |
| h (Hour) | Prep. HPLC (Preparative high pressure liquid chromatography) |
| HCl (Hydrochloric acid) | Prep. TLC (Preparative thin layer chromatography) |
| I$_2$ (Diiodine) | rt (Room temperature) |
| KOtBu (Potassium tert-butoxide) | RT (Retention Time) |
| KOH (Potassium hydroxide) | TFA (Trifluoroacetic acid) |
| K$_2$CO$_3$ (Potassium carbonate) | TfOH (Trifluoromethane sulfonic acid) |
| LDA (Lithium diisopropylamide) | THF (Tetrahydrofuran) |
| LiHMDS (Lithium bis(trimethylsilyl)amide) | TLC (Thin layer chromatography) |
| LiOH (Lithium hydroxide) | UPLC-MS (Ultra Performance Liquid Chromatography Mass Spectrum) |
| M (Molar) | Xantphos (4,5-Bis(diphenylphosphino)-9,9-dimethylxanthene) |
| MeOH (Methanol) | |

All references to brine refer to a saturated aqueous solution of NaCl. Unless otherwise indicated, all temperatures are expressed in ° C. (degrees Centigrade). All reactions are conducted under an inert atmosphere at room temperature unless otherwise noted.

Most of the reactions were monitored by thin-layer chromatography on 0.25 mm Merck silica gel plates (60F-254), visualized with UV light. Flash column chromatography was performed on prepacked silica gel cartridges (15-40 μM, Merck).

Melting point determination was performed on a Buchi B-540 apparatus.

$^1$H-NMR spectra were recorded on a Bruker 300 MHz or 400 MHz. Chemical shifts are expressed in parts per million (ppm, δ units). Coupling constants are in units of hertz (Hz) Splitting patterns describe apparent multiplicities and are designated as s (singlet), d (doublet), t (triplet), q (quadruplet), m (multiplet), br (broad).

EXAMPLES

Example 1: 6-Methyl-N-(4-methylpyrimidin-2-yl)-4,5,6,8-tetrahydropyrazolo[3,4-b]thiazolo[4,5-d]azepin-2-amine (Final Compound 1-1)

Ethyl 1-(4-methoxybenzyl)-1H-pyrazole-4-carboxylate

According to Scheme 1, Step 1: A suspension of ethyl 1H-pyrazole-4-carboxylate (535 mmol, 75.0 g), 1-(chloromethyl)-4-methoxybenzene (562 mmol, 76 mL) and K$_2$CO$_3$ (803 mmol, 111 g) in ACN (750 mL) was heated under reflux for 4 h. At rt, the reaction mixture was filtered and concentrated under reduced pressure. The resulting yellow oil was triturated in petroleum ether and the precipitate isolated by filtration and dried under reduced pressure to yield the title compound (530 mmol, 138 g, 99%) as a white solid.

UPLC-MS: RT=1.01 min; MS m/z ES$^+$=261.

1-(4-Methoxybenzyl)-1H-pyrazole-4-carboxylic acid

According to Scheme 1, Step 2: A solution of LiOH (358 mmol, 15.3 g) in water (2 M) was added at rt to a solution of ethyl 1-(4-methoxybenzyl)-1H-pyrazole-4-carboxylate (143 mmol, 37.2 g) in THF/MeOH (1:1, 400 mL) and the reaction mixture was heated at 60° C. overnight. After evaporation of the solvents, a solid was filtered, water (150 mL) was added and the aqueous phase was extracted with Et$_2$O. The aqueous phase was then acidified with a solution of HCl 1 M until pH=1-2 and extracted with DCM. The organic phase was washed with brine, dried over MgSO$_4$, filtered and concentrated under reduced pressure to yield the title compound (138 mmol, 32.1 g, 97%) as a pale yellow solid. The crude product was used without further purification.

UPLC-MS: RT=0.77 min; MS m/z ES$^-$=231.

N-Methoxy-1-(4-methoxybenzyl)-N-methyl-1H-pyrazole-4-carboxamide

According to Scheme 1, Step 3: A solution of 1-(4-methoxybenzyl)-1H-pyrazole-4-carboxylic acid (34.4 mmol, 8.00 g), oxalyl chloride (68.9 mmol, 5.92 mL) and a drop of DMF in DCM (80 mL) was stirred for 1 h at rt. After evaporation, the crude product was dissolved in DCM (30 mL) and was added at 0° C. to a solution of N,O-dimethylhydroxylamine hydrochloride (103 mmol, 6.31 g) in DCM (100 mL), followed by Et$_3$N (138 mmol, 19.2 mL). The reaction mixture was stirred for 1 h at rt. The reaction was quenched with a saturated aqueous solution of Na$_2$CO$_3$ (300 mL) and the aqueous phase was extracted with DCM. The organic layer was dried over MgSO$_4$, filtered and concentrated to dryness to yield the title compound (33.8 mmol, 9.30 g, 98%) as a beige solid.

UPLC-MS: RT=0.72 min; MS m/z ES$^+$=276.

3-Chloro-N-methoxy-1-(4-methoxybenzyl)-N-methyl-1H-pyrazole-4-carboxamide

According to Scheme 1, Step 4: BuLi 2.5 M (84 mmol, 34 mL) was added to a solution of diisopropylamine (84 mmol, 12 mL) in THF (100 mL) at −78° C. and the reaction mixture was stirred at −78° C. for 5 min and then at rt. The resulting LDA solution was added at −78° C. to a solution of N-methoxy-1-(4-methoxybenzyl)-N-methyl-1H-pyrazole-4-carboxamide (36.3 mmol, 10.0 g) in THF (30 mL) and the reaction mixture was stirred for 5 min at −78° C. Then a solution of hexachloroethane (84.0 mmol, 19.9 g) in THF (30 mL) was added to the black reaction mixture at −78° C. The solution was stirred for 5 min at −78° C. and for 1 h at rt. The reaction mixture was quenched with water (50 mL) and the aqueous phase was extracted with EtOAc. The organic phase was dried over MgSO$_4$, was filtered and was concentrated to give a brown oil. The resulting crude product was purified by flash chromatography over silica gel using cyclohexane/EtOAc (100:0 to 50:50) as eluent to yield after evaporation the title compound (16 mmol, 5.0 g, 42%) as a beige solid.

UPLC-MS: RT=0.85 min; MS m/z ES$^+$=310.

N-Methoxy-1-(4-methoxybenzyl)-N-methyl-3-(methylamino)-1H-pyrazole-4-carboxamide According to Scheme 1, Step 5: A solution of 3-chloro-N-methoxy-1-(4-methoxybenzyl)-N-methyl-1H-pyrazole-4-carboxamide (3.23 mmol, 1.00 g) and methanamine hydrate (32.3 mmol, 4.00 mL) in NMP (10 mL) was heated in the microwave at 140° C. for 1.5 h. The reaction was diluted with EtOAc and the organic layer was washed with water, dried over MgSO$_4$, filtered and concentrated to dryness. The crude compound was purified by flash chromatography with silica gel using cyclohexane/EtOAc (10:0 to 5:5) as eluent to yield the title compound (1.81 mmol, 550 mg, 56%).

UPLC-MS: RT=0.79 min; MS m/z ES$^+$=305.

3-(Allyl(methyl)amino)-N-methoxy-1-(4-methoxybenzyl)-N-methyl-1H-pyrazole-4-carboxamide According to Scheme 1, Step 6: To a solution of N-methoxy-1-(4-methoxybenzyl)-N-methyl-3-(methylamino)-1H-pyrazole-4-carboxamide (1.64 mmol, 500 mg) in THF/DMF (5 mL; 1:1) was added portionwise NaH (3.28 mmol, 131 mg, 60%) and the reaction mixture was stirred for 45 min at rt. 3-Bromoprop-1-ene (4.11 mmol, 350 μL) was then added and the solution was stirred for 2 h at 65° C. The solution was concentrated, was dissolved with DCM and was washed with a saturated solution of Na$_2$CO$_3$. The organic layer was dried over MgSO$_4$, filtered and concentrated to dryness. The crude compound was purified by flash chromatography with silica gel using DCM/MeOH (98:2) as eluent to yield the title compound (0.90 mmol, 310 mg, 55%).

UPLC-MS: RT=0.98 min; MS m/z ES⁺=345.

1-(3-(Allyl(methyl)amino)-1-(4-methoxybenzyl)-1H-pyrazol-4-yl)prop-2-en-1-one According to Scheme 1, Step 7: Under a nitrogen atmosphere, vinylmagnesium bromide (2.70 mmol, 354 mg) was added to a solution of 3-(allyl(methyl)amino)-N-methoxy-1-(4-methoxybenzyl)-N-methyl-1H-pyrazole-4-carboxamide (0.90 mmol, 310 mg) in THF (10 mL), and the resulting solution was stirred for 15 min at rt. Some more vinylmagnesium bromide (2.70 mmol, 236 mg) was added to complete the reaction. Then the reaction mixture was quenched with water and the aqueous phase was extracted with EtOAc. The organic layer was dried over $MgSO_4$, filtered and concentrated to dryness. The crude compound was purified by flash chromatography with silica gel using cyclohexane/EtOAc (100:0 to 70:30) as eluent to yield the title compound (0.87 mmol, 250 mg, 89%).

UPLC-MS: RT=1.09 min; MS m/z ES⁺=312.

(Z)-2-(4-Methoxybenzyl)-8-methyl-7,8-dihydropyrazolo[3,4-b]azepin-4(2H)-one

According to Scheme 1, Step 8: Under a nitrogen atmosphere, Grubbs catalyst $2^{nd}$ generation (benzylidene[1,3-bis(2,4,6-trimethylphenyl)-2-imidazolidinylidene]dichloro(tricyclohexylphosphine)ruthenium; 0.08 mmol, 68.3 mg) was added to a solution of 1-(3-(allyl(methyl)amino)-1-(4-methoxybenzyl)-1H-pyrazol-4-yl)prop-2-en-1-one (0.80 mmol, 250 mg) in DCM (110 mL) and the solution was stirred for 1 h under reflux. The reaction mixture was evaporated to dryness. The crude compound was purified by flash chromatography with silica gel using DCM/MeOH (100:0 to 97:3) as eluent to yield the title compound (0.76 mmol, 215 mg, 95%).

UPLC-MS: RT=0.8 min; MS m/z ES⁺=284.

2-(4-Methoxybenzyl)-8-methyl-5,6,7,8-tetrahydropyrazolo[3,4-b]azepin-4(2H)-one According to Scheme 1, Step 9: A mixture of (Z)-2-(4-methoxybenzyl)-8-methyl-7,8-dihydropyrazolo[3,4-b]azepin-4(2H)-one (0.76 mmol, 215 mg), ammonium formate (7.59 mmol, 478 mg) and $Pd(OH)_2$ (0.15 mmol, 21.3 mg) in MeOH (8 mL) was stirred under reflux for 2 h. The reaction mixture was filtered through celite pad and was washed with MeOH. The filtrate was concentrated to dryness then dissolved with EtOAc and was washed with a saturated aqueous solution of $Na_2CO_3$. The organic layer was dried over $MgSO_4$, filtered and concentrated to dryness to yield the title compound (0.70 mmol, 200 mg, 92%).

UPLC-MS: RT=0.79 min; MS m/z ES⁺=286.

5-Bromo-2-(4-methoxybenzyl)-8-methyl-5,6,7,8-tetrahydropyrazolo[3,4-b]azepin-4(2H)-one According to Scheme 1, Step 10: To a solution of 2-(4-methoxybenzyl)-8-methyl-5,6,7,8-tetrahydropyrazolo[3,4-b]azepin-4(2H)-one (0.70 mmol, 200 mg) in MeOH (7 mL) was added $CuBr_2$ (2.10 mmol, 470 mg) and the solution was heated under reflux for 2 h. After evaporation, the crude residue was dissolved in DCM and the organic phase was washed with a saturated aqueous solution of $Na_2CO_3$. The organic layer was dried over $MgSO_4$, filtered and concentrated to dryness. The crude compound was purified by flash chromatography with silica gel using DCM/MeOH (100:0 to 97:3) as eluent to yield the title compound (0.56 mmol, 205 mg, 80%).

UPLC-MS: RT=0.91 min; MS m/z ES⁺=364.

8-(4-Methoxybenzyl)-6-methyl-N-(4-methylpyrimidin-2-yl)-4,5,6,8-tetrahydropyrazolo[3,4-b]thiazolo[4,5-d]azepin-2-amine According to Scheme 1, Step 11: A mixture of 5-bromo-2-(4-methoxybenzyl)-8-methyl-5,6,7,8-tetrahydropyrazolo[3,4-b]azepin-4(2H)-one (0.27 mmol, 100 mg) and 1-(4-methylpyrimidin-2-yl)thiourea (0.27 mmol, 46.2 mg) in EtOH (5 mL) was heated under reflux overnight. Then the solution was concentrated to dryness, the residue was solubilised in EtOAc and the organic phase was washed with a saturated aqueous solution of $Na_2CO_3$. The organic layer was dried over $MgSO_4$, filtered and concentrated to dryness. The crude compound was purified by flash chromatography with silica gel using cyclohexane/EtOAc (100:0 to 0:100) as eluent to yield the title compound (0.10 mmol, 45 mg, 38%).

UPLC-MS: RT=1.06 min; MS m/z ES⁺=434.

6-Methyl-N-(4-methylpyrimidin-2-yl)-4,5,6,8-tetrahydropyrazolo[3,4-b]thiazolo[4,5-d]azepin-2-amine According to Scheme 1, Step 12, Method A: Trifluoromethanesulfonic acid (0.52 mmol, 78 mg) was added to a solution of 8-(4-methoxybenzyl)-6-methyl-N-(4-methylpyrimidin-2-yl)-4,5,6,8-tetrahydropyrazolo[3,4-b]thiazolo[4,5-d]azepin-2-amine (0.10 mmol, 45 mg) in TFA (100 µL). The reaction mixture was stirred at rt for 15 min. The solution was quenched with water and extracted with EtOAc. The organic layer was dried over $MgSO_4$, was filtered and was concentrated. The crude compound was purified by flash chromatography with silica gel using DCM/MeOH (100:0 to 94:6) as eluent to yield the title compound (48 mol, 15 mg, 46%) as a white powder.

UPLC-MS: RT=0.72 min; MS m/z ES⁺=314.

¹H-NMR (300 MHz, DMSO-d₆): 12.0 (s, 1H), 11.3 (s, 1H), 8.4 (d, 1H), 7.6 (s, 1H), 6.95 (d, 1H), 3.3 (m, 2H), 3.05 (m, 2H), 2.95 (s, 3H), 2.45 (s, 3H).

Example 2: 6-Isopropyl-N-(4-methylpyrimidin-2-yl)-4,5,6,8-tetrahydropyrazolo[3,4-b]thiazolo[4,5-d]azepin-2-amine (Final Compound 1-5)

According to Scheme 1, Step 12, Method B: A solution of 6-isopropyl-8-(4-methoxybenzyl)-N-(4-methylpyrimidin-2-yl)-4,5,6,8-tetrahydropyrazolo[3,4-b]thiazolo[4,5-d]azepin-2-amine (118 mg, 0.26 mmol, synthesized as in Scheme 1) in TFA (3 mL) was stirred at 60° C. for 1 h. TFA was evaporated under reduced pressure to afford a yellow solid. The crude solid was dissolved in EtOAc. The organic layer was washed twice with a saturated $Na_2CO_3$ solution, once with brine, dried over $Na_2SO_4$, filtered and concentrated under reduced pressure. The crude residue was purified by flash chromatography over silica gel using DCM/MeOH (96:4) as eluent to yield the title compound (82 mot, 28 mg, 32%) as a yellow solid.

UPLC-MS: RT=0.85 min; MS m/z ES⁺=342;

¹H-NMR (300 MHz, DMSO-d₆): 8.43 (1H, d, 5 Hz), 7.67 (1H, s), 6.88 (1H, d, 5 Hz), 3.34 (1H, m), 3.20-3.17 (2H, m), 2.99-2.95 (2H, m), 2.42 (3H, s), 1.14 (6H, d, 6.7 Hz).

Example 3: N-(5-Fluoropyrimidin-2-yl)-6-methyl-4,5,6,8-tetrahydropyrazolo[3,4-b]thiazolo[4,5-d]azepin-2-amine (Final Compound 1-2)

8-(4-Methoxybenzyl)-6-methyl-4,5,6,8-tetrahydropyrazolo[3,4-b]thiazolo[4,5-d]azepin-2-amine According to Scheme 2, Step 1: A mixture of 5-bromo-2-(4-methoxybenzyl)-8-methyl-5,6,7,8-tetrahydropyrazolo[3,4-b]azepin-4(2H)-one (0.27 mmol, 100 mg, synthesized as in Scheme 1) and thiourea (0.27 mmol, 21 mg) in EtOH (3 mL) was heated under reflux overnight. After evaporation, the crude compound was dissolved EtOAc and the organic phase was washed with a saturated aqueous solution of $Na_2CO_3$. The organic layer was dried over $MgSO_4$, filtered and concentrated to dryness. The crude compound was purified by flash chromatography with silica gel using cyclohexane/EtOAc (100:0 to 0:100) as eluent to yield the title compound (0.13 mmol, 45 mg, 48%).
UPLC-MS: RT=0.68 min; MS m/z ES$^+$=342.

N-(5-Fluoropyrimidin-2-yl)-8-(4-methoxybenzyl)-6-methyl-4,5,6,8-tetrahydropyrazolo[3,4-b]thiazolo[4,5-d]azepin-2-amine According to Scheme 2, Step 2: A mixture of 8-(4-methoxybenzyl)-6-methyl-4,5,6,8-tetrahydropyrazolo[3,4-b]thiazolo[4,5-c]azepin-2-amine (0.13 mmol, 45 mg), 2-chloro-5-fluoropyrimidine (0.20 mmol, 26.2 mg), sodium 2-methylpropan-2-olate (0.13 mmol, 12.7 mg), (R)-(−)-1-[(S)-2-(dicyclohexylphosphino)ferrocenyl]ethyldi-t-butylphosphine (13 µmol, 7.3 mg) and Pd(OAc)$_2$ (13 µmol, 3.0 mg) in DME (1.3 mL) was heated in the microwave at 120° C. for 2 h. After evaporation, the crude residue was purified by flash chromatography with silica gel using DCM/MeOH (100:0 to 97:3) to yield the title compound (0.10 mmol, 45 mg, 78%).
UPLC-MS: RT=1.06 min; MS m/z ES$^+$=438.
N-(5-Fluoropyrimidin-2-yl)-6-methyl-4,5,6,8-tetrahydropyrazolo[3,4-b]thiazolo[4,5-d]azepin-2-amine (47 µmol, 15 mg, 46%) was obtained as a beige solid following the same experimental part as described for Example 1, Step 12, Method A.
UPLC-MS: RT=1.06 min; MS m/z ES$^+$=318;
$^1$H-NMR (300 MHz, DMSO-d$_6$): 11.8 (s, 1H), 8.7 (s, 2H), 7.7 (s, 1H), 3.3 (m, 2H), 3.0 (m, 2H), 2.9 (s, 3H).

Example 4: 6-(Cyclopropylmethyl)-N-(5-fluoropyrimidin-2-yl)-4,5,6,8-tetrahydropyrazolo[3,4-b]thiazolo[4,5-d]azepin-2-amine (Final Compound 1-4)

According to Scheme 2, Step 3, Method B: 6-(Cyclopropylmethyl)-N-(5-fluoropyrimidin-2-yl)-8-(4-methoxybenzyl)-4,5,6,8-tetrahydropyrazolo[3,4-b]thiazolo[4,5-d]azepin-2-amine (45 mg, 94 µmol, synthesized as in Scheme 2) was dissolved into TFA. The solution was stirred at rt for 15 min and then at 60° C. for 1 h. The mixture was diluted with water and extracted with EtOAc. The organic layer was dried over MgSO$_4$, filtered and concentrated under reduced pressure. The crude residue was purified by flash chromatography over silica gel using DCM/MeOH (100:0 to 94:6) as eluent to yield the title compound (17 µmol, 6 mg, 18%) as a beige solid.
UPLC-MS: RT=0.92 min; MS m/z ES$^+$=358;
$^1$H-NMR (300 MHz, DMSO-d$_6$): 12.0 (s, 1H), 11.3 (s, 1H) 8.7 (s, 2H), 7.6 (s, 1H), 3.4 (m, 2H), 3.1 (m, 2H), 2.95 (m, 2H), 2.45 (s, 3H).

Example 5: 6-(2-Methoxyethyl)-N-(6-methylpyridin-2-yl)-4,5,6,8-tetrahydropyrazolo[3,4-b]thiazolo[4,5-d]azepin-2-amine (Final Compound 1-13)

6-(2-Methoxyethyl)-4,5,6,8-tetrahydropyrazolo[3,4-b]thiazolo[4,5-d]azepin-2-amine According to Scheme 3, Step 1: The title compound was obtained using the same procedure as described in Scheme 2, Step 3, Method B with 8-(4-methoxybenzyl)-6-(2-methoxyethyl)-4,5,6,8-tetrahydropyrazolo[3,4-b]thiazolo[4,5-d]azepin-2-amine (184 mg, 0.48 mmol, synthesized as in Scheme 2) in TFA (2.5 mL) to yield 6-(2-methoxyethyl)-4,5,6,8-tetrahydropyrazolo[3,4-b]thiazolo[4,5-d]azepin-2-amine (294 µmol, 78 mg, 62%).
UPLC-MS: RT=0.40-0.44 min; MS m/z ES$^+$=266.

6-(2-Methoxyethyl)-N-(6-methylpyridin-2-yl)-4,5,6,8-tetrahydropyrazolo[3,4-b]thiazolo[4,5-d]azepin-2-amine According to Scheme 3, Step 2: A mixture of 6-(2-methoxyethyl)-4,5,6,8-tetrahydropyrazolo[3,4-b]thiazolo[4,5-d]azepin-2-amine (40 mg, 0.15 mmol), 2-bromo-6-methylpyridine (34 µL, 302 µmol), sodium 2-methylpropan-2-olate (21.7 mg, 226 µmol), Pd$_2$(dba)$_3$ (13.8 mg, 15 µmol) and Xantphos (17.4 mg, 30 µmol) in toluene (1.5 mL) was stirred at 90° C. for 30 min. The mixture was diluted with EtOAc. The organic layer was washed first with a saturated K$_2$CO$_3$ solution and then with brine, dried over Na$_2$SO$_4$, filtered and concentrated under reduced pressure to afford a brown residue. The crude residue was purified by preparative HPLC to yield the title compound (8 µmol, 3 mg, 6%) as a brown solid.
UPLC-MS: RT=0.68 min; MS m/z ES$^+$=357;
$^1$H-NMR (300 MHz, CDCl$_3$): 8.59 (1H, s), 8.04 (1H, s), 7.51 (1H, m), 6.81-6.74 (2H, m), 3.98 (3H, s), 3.68-3.61 (4H, m), 3.53-3.49 (2H, m), 3.07-3.04 (2H, m), 2.54 (3H, s).

Example 6: N-(5-Fluoropyrimidin-2-yl)-6-(pyridin-2-ylmethyl)-4,5,6,8-tetrahydropyrazolo[3,4-b]thiazolo[4,5-d]azepin-2-amine (Final Compound 1-26)

2-(4-Methoxybenzyl)-8-(pyridin-2-ylmethyl)-5,6,7,8-tetrahydropyrazolo[3,4-b]azepin-4(2H)-one According to Scheme 8, Step 6, Method B: To a solution of 2-(4-methoxybenzyl)-5,6,7,8-tetrahydropyrazolo[3,4-b]azepin-4(2H)-one (300 mg, 1.11 mmol, synthesized as in Scheme 7) in THF (6 mL) was added LiHMDS (1.25 mL, 1.33 mmol) and the reaction mixture was stirred at rt for 30 min. In another flask, K$_2$CO$_3$ (458 mg, 3.32 mmol) was added to a solution of 2-(bromomethyl)pyridine hydrobromide (559 mg, 2.21 mmol) in DMF (6 mL) and the reaction mixture was stirred for 30 min. The latter solution was added to the initial reaction mixture. The resulting mixture was stirred at rt for 45 min. After evaporation of the solvents, water was added to the residue and the aqueous layer was extracted with EtOAc. The organic layer was dried over MgSO$_4$, filtered and concentrated under reduced pressure. The crude residue was purified by preparative HPLC to yield the title compound (157 µmol, 57 mg, 14%).
UPLC-MS: RT=0.70 min; MS m/z ES$^+$=363.

N-(5-Fluoropyrimidin-2-yl)-8-(4-methoxybenzyl)-6-(pyridin-2-ylmethyl)-4,5,6,8-tetrahydropyrazolo[3,4-b]thiazolo[4,5-d]azepin-2-amine According to Scheme 4, Step 1: A solution of 2-(4-methoxybenzyl)-8-(pyridin-2-ylmethyl)-5,6,7,8-tetrahydropyrazolo[3,4-b]azepin-4(2H)-one (57 mg, 157 µmol), (5-fluoropyrimidin-2-yl)thiourea (32.5 mg, 189 µmol) and I$_2$ (39.9 mg, 157 µmol) in pyridine (315 µl) was stirred at 90° C. for 4 h. After dilution with water of the reaction mixture, the aqueous layer was extracted twice with DCM. The organic layers were combined, dried over MgSO$_4$, filtered and concentrated under reduced pressure to yield the title compound (39 µmol, 20 mg, 25%).

UPLC-MS: RT=0.94 min; MS m/z ES$^+$=515.

N-(5-Fluoropyrimidin-2-yl)-6-(pyridin-2-ylmethyl)-4,5,6,8-tetrahydropyrazolo[3,4-b]thiazolo[4,5-d]azepin-2-amine According to Scheme 4, Step 2: The title compound was obtained using the same procedure as described in Scheme 1, Step 12, Method B with N-(5-fluoropyrimidin-2-yl)-8-(4-methoxybenzyl)-6-(pyridin-2-ylmethyl)-4,5,6,8-tetrahydropyrazolo[3,4-b]thiazolo[4,5-d]azepin-2-amine (20 mg, 39 µmol) in TFA (2 mL) to yield N-(5-fluoropyrimidin-2-yl)-6-(pyridin-2-ylmethyl)-4,5,6,8-tetrahydropyrazolo[3,4-b]thiazolo[4,5-d]azepin-2-amine (8 µmol, 3.2 mg, 21%) as a brown solid.

UPLC-MS: RT=0.62 min; MS m/z ES$^+$=395.

$^1$H-NMR (300 MHz, CD$_3$OD): 8.5 (2H, s), 8.5 (1H, m), 7.9 (1H, m), 7.8 (1H, m), 7.5 (1H, m), 7.4 (1H, m), 4.7 (2H, s), 3.4 (2H, m), 3.0 (2H, m).

Example 7: 6-((1-Methyl-1H-pyrazol-3-yl)methyl)-N-(4-methylpyrimidin-2-yl)-4,5,6,8-tetrahydropyrazolo[3,4-b]thiazolo[4,5-d]azepin-2-amine (Final Compound 1-16)

Ethyl 3-amino-1-(4-methoxybenzyl)-1H-pyrazole-4-carboxylate

According to Scheme 5 Step 1: 1-(Chloromethyl)-4-methoxybenzene (12.9 mmol, 2.02 g) followed by K$_2$CO$_3$ (25.8 mmol, 3.56 g) were added to a solution of ethyl 3-amino-1H-pyrazole-4-carboxylate (12.9 mmol, 2.00 g) in ACN (10 mL) and then the reaction mixture was heated at 60° C. for 3 h. After evaporation of the solvent, a saturated solution of Na$_2$CO$_3$ was added and the aqueous phase was extracted with AcOEt. The organic phase was dried over Na$_2$SO$_4$, was filtered and was concentrated under reduced pressure. The crude product was purified by flash chromatography over silica gel using cyclohexane/AcOEt (100:0 to 20:80) as eluent to afford ethyl 3-amino-1-(4-methoxybenzyl)-1H-pyrazole-4-carboxylate (6.90 mmol, 1.90 g, 53%) as a white powder.

UPLC-MS: RT=0.82 min; MS m/z ES$^+$=276.

Ethyl 1-(4-methoxybenzyl)-3-((1-methyl-1H-pyrazol-3-yl)methylamino)-1H-pyrazole-4-carboxylate According to Scheme 5, Step 2: To a solution of ethyl 3-amino-1-(4-methoxybenzyl)-1H-pyrazole-4-carboxylate (573 mg, 2.08 mmol) in DCM (20 mL) was added 1-methyl-1H-pyrazole-3-carbaldehyde (229 mg, 2.08 mmol) and AcOH (5.96 mL, 104 mmol). After cooling the reaction mixture to 0° C., NaBH(OAc)$_3$ (882 mg, 4.16 mmol) was added portionwise and the reaction mixture was stirred at rt for 1 day. The mixture was quenched with an aqueous NaHCO$_3$ solution. The aqueous layer was extracted 3 times with DCM. The organic layers were combined, dried over MgSO$_4$, filtered and concentrated under reduced pressure. The crude residue was purified by flash chromatography over silica gel using cyclohexane/EtOAc (100:0 to 0:100) as eluent to yield the title compound (0.73 mmol, 270 mg, 35%).

UPLC-MS: RT=0.92 min; MS m/z ES$^+$=370.

Ethyl 3-(allyl((1-methyl-1H-pyrazol-3-yl)methyl)amino)-1-(4-methoxybenzyl)-1H-pyrazole-4-carboxylate According to Scheme 5, Step 3: The title compound was obtained using the same procedure as described in Scheme 1, Step 6 with ethyl 1-(4-methoxybenzyl)-3-((1-methyl-1H-pyrazol-3-yl)methylamino)-1H-pyrazole-4-carboxylate (220 mg, 0.60 mmol), NaH (71.5 mg, 1.79 mmol, 60%) and 3-bromoprop-1-ene (0.10 mL, 1.19 mmol) in THF/DMF (1:1, 2 mL) to yield ethyl 3-(allyl((1-methyl-1H-pyrazol-3-yl)methyl)amino)-1-(4-methoxybenzyl)-1H-pyrazole-4-carboxylate (0.49 mmol, 200 mg, 82%).

UPLC-MS: RT=1.07 min; MS m/z ES$^+$=411.

3-(Allyl(1-methyl-1H-pyrazol-3-yl)methyl)amino)-1-(4-methoxybenzyl)-1H-pyrazole-4-carboxylic acid According to Scheme 5, Step 4: To a solution of ethyl 3-(allyl((1-methyl-1H-pyrazol-3-yl)methyl)amino)-1-(4-methoxybenzyl)-1H-pyrazole-4-carboxylate (200 mg, 0.49 mmol) in MeOH/water (3:1, 12 mL) was added LiOH (58.5 mg, 2.44 mmol) and the reaction mixture was stirred at 80° C. for 2 h. Then MeOH was evaporated and water was added to the residue. The aqueous layer was acidified to pH=5 with 1N HCl and extracted 3 times with DCM. The organic layers were combined, dried over MgSO$_4$, filtered and concentrated under reduced pressure to yield the title compound (0.37 mmol, 140 mg, 75%).

UPLC-MS: RT=0.84 min; MS m/z ES$^+$=382.

3-(Allyl(1-methyl-1H-pyrazol-3-yl)methyl)amino)-N-methoxy-1-(4-methoxybenzyl)-N-methyl-1H-pyrazole-4-carboxamide According to Scheme 5, Step 5: The title compound was obtained using the same procedure as described in Scheme 1, Step 3 with 3-(allyl((1-methyl-1H-pyrazol-3-yl)methyl)amino)-1-(4-methoxybenzyl)-1H-pyrazole-4-carboxylic acid (140 mg, 0.37 mmol), oxalyl dichloride (63.0 µl, 734 µmol), a drop of DMF, Et$_3$N (133 µl, 954 µmol) and N,O-dimethylhydroxylammonium chloride (53.7 mg, 551 µmol) to yield 3-(allyl((1-methyl-1H-pyrazol-3-yl)methyl)amino)-N-methoxy-1-(4-methoxybenzyl)-N-methyl-1H-pyrazole-4-carboxamide (236 µmol, 100 mg, 64%).

UPLC-MS: RT=0.87 min; MS m/z ES$^+$=426.

6-((1-Methyl-1H-pyrazol-3-yl)methyl)-N-(4-methylpyrimidin-2-yl)-4,5,6,8-tetrahydropyrazolo[3,4-b]thiazolo[4,5-d]azepin-2-amine (3 µmol, 1.2 mg, 26%) was obtained as a yellow solid following the same experimental part as described for Example 1 from Step 7 until Step 12, Method A.

UPLC-MS: RT=0.74 min; MS m/z ES$^+$=394;

$^1$H-NMR (300 MHz, CD$_3$OD): 8.4 (1H, d, 4.8 Hz), 7.85 (1H, s), 7.5 (1H, d, 2.3 Hz), 6.8 (1H, d, 4.8 Hz), 6.2 (1H, d, 2.3 Hz), 4.5 (2H, s), 3.85 (3H, s), 3.35 (2H, m), 2.95 (2H, m), 2.45 (3H, s).

Example 8: N-(5-Fluoropyrimidin-2-yl)-6-(3,3,3-trifluoropropyl)-4,5,6,8-tetrahydropyrazolo[3,4-b]thiazolo[4,5-d]azepin-2-amine (Final Compound 1-29)

3-Amino-N-methoxy-1-(4-methoxybenzyl)-N-methyl-1H-pyrazole-4-carboxamide

According to Scheme 6, Step 1: Under nitrogen, a solution of ethyl 3-amino-1-(4-methoxybenzyl)-1H-pyrazole-4-carboxylate (3.00 g, 10.9 mmol, synthesized as in Scheme 5) in DCM (50 mL) was stirred at 0° C. AlMe$_3$ (6.28 g, 87.0 mmol) was added dropwise at 0° C. and the solution was stirred at 0° C. for 20 min and at rt for 20 min. After cooling the reaction mixture to 0° C., N,O-dimethylhydroxylamine hydrochloride (4.25 g, 43.6 mmol) was added dropwise at 0° C. and the mixture was stirred at rt for 10 min and at reflux for 5 h. The mixture was slowly quenched with water and extracted 2 times with DCM. The organic layers were combined, dried over MgSO$_4$, filtered and concentrated under reduced pressure. The crude residue was purified by flash chromatography over silica gel using cyclohexane/EtOAc (50:50 to 0:100) as eluent to yield the title compound (6.20 mmol, 1.80 g, 57%).

UPLC-MS: RT=0.71 min; MS m/z ES$^+$=291.

N-Methoxy-1-(4-methoxybenzyl)-N-methyl-3-(3,3,3-trifluoropropylamino)-1H-pyrazole-4-carboxamide According to Scheme 6, Step 2: The title compound was obtained using the same procedure as described in Scheme 4, Step 1 with 3-amino-N-methoxy-1-(4-methoxybenzyl)-N-methyl-1H-pyrazole-4-carboxamide (720 mg, 2.48 mmol), AcOH (8 mL), 3,3,3-trifluoropropanal (834 mg, 7.44 mmol) and NaBH(OAc)$_3$ (2.10 g, 9.92 mmol) in DCM (20 mL) to yield N-methoxy-1-(4-methoxybenzyl)-N-methyl-3-(3,3,3-trifluoropropylamino)-1H-pyrazole-4-carboxamide (1.82 mmol, 705 mg, 74%).

UPLC-MS: RT=1.02 min; MS m/z ES$^+$=387.

3-(Allyl(3,3,3-trifluoropropyl)amino)-N-methoxy-1-(4-methoxybenzyl)-N-methyl-1H-pyrazole-4-carboxamide According to Scheme 6, Step 3: To a solution of N-methoxy-1-(4-methoxybenzyl)-N-methyl-3-(3,3,3-trifluoropropylamino)-1H-pyrazole-4-carboxamide (580 mg, 1.50 mmol) in THF (25 mL) was added LiHMDS (502 mg, 3.00 mmol) and the reaction mixture was stirred at rt for 15 min. Then 3-bromoprop-1-ene (363 mg, 3.00 mmol) was added and the reaction mixture was stirred at reflux for 1 h. The reaction mixture was quenched with water and extracted with EtOAc. The organic layer was dried over MgSO$_4$, filtered and concentrated under reduced pressure. The crude residue was purified by flash chromatography over silica gel using cyclohexane/EtOAc (100:0 to 40:60) as eluent to yield the title compound (1.01 mmol, 430 mg, 67%).

UPLC-MS: RT=1.12 min; MS m/z ES$^+$=427.

N-(5-fluoropyrimidin-2-yl)-6-(3,3,3-trifluoropropyl)-4,5,6,8-tetrahydropyrazolo[3,4-b]thiazolo[4,5-d]azepin-2-amine (24 µmol, 9.6 mg, 25%) was obtained as a beige solid following the same experimental part as described in the Scheme 1 from Steps 7 to 9, then Scheme 4 Step 1 and finally Scheme 1 Step 12, Method B.

UPLC-MS: RT=0.98 min; MS m/z ES$^+$=400;

$^1$H-NMR (300 MHz, DMSO-d$_6$): 11.7 (s, 1H), 8.7 (s, 2H), 7.7 (s, 1H), 3.5 (m, 4H), 3.4 (m, 2H), 3.0 (m, 2H).

Example 9: N-(4-Methylpyrimidin-2-yl)-6-((tetrahydrofuran-2-yl)methyl)-4,5,6,8-tetrahydropyrazolo[3,4-b]thiazolo[4,5-d]azepin-2-amine (Final Compound 1-10)

Ethyl 5-[(4-ethoxy-4-oxobutyl)amino]-1-(4-methoxybenzyl)-1H-pyrazole-4-carboxylate According to Scheme 7, Step 1: To a suspension of ethyl 5-amino-1-(4-methoxybenzyl)-1H-pyrazole-4-carboxylate (50.0 g, 180 mmol) and K$_2$CO$_3$ (49.0 g, 360 mmol) in NMP (700 mL) was added 4-bromo-butyric acid ethyl ester (140 g, 720 mmol), and the mixture was heated at 120° C. for 36 h. After cooling to rt, water (500 mL) was added to the mixture and it was extracted with EtOAc (200 mL×3). The combined organic layers were dried over Na$_2$SO$_4$, filtered and concentrated in vacuum. The residue was purified by silica gel chromatography (PE:EtOAc=20:1 to 7:1) to give the title product (58 g, 83%).

MS (ESI) m/z 390 (M+H)$^+$

Ethyl 5-[benzyl(4-ethoxy-4-oxobutyl)amino]-1-(4-methoxybenzyl)-1H-pyrazole-4-carboxylate According to Scheme 7, Step 2: To a suspension of ethyl 5-[(4-ethoxy-4-oxobutyl)amino]-1-(4-methoxybenzyl)-1H-pyrazole-4-carboxylate (10 g, 26 mmol) and K$_2$CO$_3$ (8.9 g, 64 mmol) in NMP (100 mL) was added BnBr (5.7 g, 33 mmol). The mixture was heated at 140° C. for 6 h. Water (100 mL) was added and the mixture was extracted with EtOAc (80 mL×3). The combined organic layers were dried over Na$_2$SO$_4$, filtered and concentrated. The residue was purified by chromatography (PE:EtOAc=20:1 to 6:1) to give the title product (10.0 g, 81%).

MS (ESI) m/z 480 (M+H)$^+$

Ethyl 8-benzyl-1-(4-methoxybenzyl)-4-oxo-1,4,5,6,7,8-hexahydropyrazolo[3,4-b]azepine-5-carboxylate According to Scheme 7, Step 3: To a solution of ethyl 5-[benzyl(4-ethoxy-4-oxobutyl)amino]-1-(4-methoxybenzyl)-1H-pyrazole-4-carboxylate (10.0 g, 21.0 mmol) in THF (100 mL) was added LiHMDS (1.0 M in THF, 52 mL, 52 mmol) at 0° C., then the solution was stirred at 70° C. for 1.5 h. Water (100 mL) was added and the mixture was extracted with EtOAc (80 mL×3). The combined organic layers were dried over Na$_2$SO$_4$, filtered and concentrated to get the title product (8.2 g, 91%).

MS (ESI): m/z 434 (M+H)$^+$;

$^1$H-NMR (400 MHz, CDCl$_3$): δ 7.63 (s, 1H), 7.21-7.29 (m, 4H), 7.13-7.18 (m, 3H), 6.80 (d, J=8.0 Hz, 2H), 4.92-4.96 (m, 2H), 4.48-4.62 (m, 2H), 4.07-4.14 (m, 2H), 3.73 (s, 3H), 3.51-3.55 (m, 1H), 3.16-3.24 (m, 2H), 2.57-2.59 (m, 1H), 2.11-2.24 (m, 1H), 1.15-1.21 (m, 3H).

8-Benzyl-1-(4-methoxybenzyl)-5,6,7,8-tetrahydropyrazolo[3,4-b]azepin-4(1H)-one According to Scheme 7, Step 4: A suspension of ethyl 8-benzyl-1-(4-methoxybenzyl)-4-oxo-1,4,5,6,7,8-hexahydropyrazolo[3,4-b]azepine-5-carboxylate (8.2 g, 19 mmol) and KOH (2.6 g, 47 mmol) in ethylene glycol (90 mL) was heated at 110° C. for 1 h. Water (100 mL) was added and the mixture was extracted with EtOAc (80 mL×3). The combined organic layers were dried over Na₂SO₄, filtered and concentrated to give the title product (6.2 g, 93%).

MS (ESI) m/z 362 (M+H)⁺;

¹H-NMR (400 MHz, CDCl₃): δ 7.61 (s, 1H), 7.20-7.24 (m, 4H), 7.14-7.18 (m, 3H), 6.80 (d, J=8.8 Hz, 2H), 4.92 (s, 2H), 4.58 (s, 2H), 3.74 (s, 3H), 3.19-3.22 (m, 2H), 2.54-2.57 (m, 2H), 1.88-1.93 (m, 2H).

1-(4-Methoxybenzyl)-5,6,7,8-tetrahydropyrazolo[3, 4-b]azepin-4(1H)-one

According to Scheme 7, Step 5: To a solution of 8-benzyl-1-(4-methoxybenzyl)-5,6,7,8-tetrahydropyrazolo[3,4-b]azepin-4(1H)-one (5.8 g, 16 mmol) in EtOH (60 mL) and AcOH (60 mL) was added to Pd(OH)₂ (600 mg), then the mixture was stirred at 50° C. under H₂ (50 Psi) for 2 h. The mixture was filtered through Celite, and the filtrate was concentrated. The residue was purified by silica gel chromatography (PE:EtOAc, 10:1 to 1:1) to give the title product (2.5 g, 57%).

MS (ESI) m/z 272 (M+H)⁺;

¹H-NMR (400 MHz, CDCl₃): δ 7.63 (s, 1H), 7.18 (d, J=8.4 Hz, 2H), 6.86 (d, J=8.4 Hz, 2H), 4.94 (s, 2H), 3.78 (s, 3H), 3.37-3.39 (m, 2H), 2.66-2.69 (m, 2H), 1.97-2.02 (m, 2H).

1-(4-Methoxybenzyl)-8-(tetrahydrofuran-2-ylmethyl)-5,6,7,8-tetrahydropyrazolo[3,4-b]azepin-4(1H)-one According to Scheme 7, Step 6: A solution of 1-(4-methoxybenzyl)-5,6,7,8-tetrahydropyrazolo[3,4-b]azepin-4(1H)-one (2.0 g, 7.4 mmol), and K₂CO₃ (2.4 g, 15 mmol) in 2-bromomethyltetrahydrofuran (20 mL) was stirred at 120° C. for 48 h. After cooling to rt, the mixture was filtered and concentrated to give the crude desired product, which was purified by chromatography on silica (PE:EtOAc=10:1 to 1:1) to give the title product (800 mg, 30%).

MS (ESI): m/z 356 (M+H)⁺

5-Bromo-1-(4-methoxybenzyl)-8-(tetrahydrofuran-2-ylmethyl)-5,6,7,8-tetrahydropyrazolo[3,4-b]azepin-4(1H)-one According to Scheme 1, Step 10: A mixture of 1-(4-methoxybenzyl)-8-(tetrahydrofuran-2-ylmethyl)-5,6,7,8-tetrahydropyrazolo[3,4-b]azepin-4(1H)-one (800 mg, 2.20 mmol) and trimethylphenylammonium tribromide (847 mg, 2.20 mmol) in CHCl₃ (15 mL) was refluxed for 1 h. After the reaction was finished, the mixture was washed with water (10 mL), dried over Na₂SO₄, filtered and concentrated under reduced pressure to give the title product (850 mg, 89%), which was used for the next step without further purification.

MS (ESI) m/z 434,436 (M+H)⁺

7-(4-Methoxybenzyl)-N-(4-methylpyrimidin-2-yl)-6-(tetrahydrofuran-2-ylmethyl)-4,5,6,7-tetrahydropyrazolo[3,4-b][1,3]thiazolo[4,5-d]azepin-2-amine According to Scheme 1, Step 11: A mixture of 5-bromo-1-(4-methoxybenzyl)-8-(tetrahydrofuran-2-ylmethyl)-5,6,7,8-tetrahydropyrazolo[3,4-b]azepin-4(1H)-one (850 mg, 2.00 mmol) and (4-methyl-pyrimidin-2-yl)thiourea (396 mg, 2.40 mmol) in t-BuOH (10 mL) and acetone (1 mL) was refluxed for 17 h. After the reaction was completed, the mixture was filtered and concentrated under reduced pressure. The residue was purified by recrystallization to give the title product (700 mg, 71%).

MS (ESI) m/z 503 (M+H)⁺

N-(4-Methylpyrimidin-2-yl)-6-((tetrahydrofuran-2-yl)methyl)-4,5,6,8-tetrahydropyrazolo[3,4-b]thiazolo[4,5-d]azepin-2-amine According to Scheme 1, Step 12, Method A: A solution of 7-(4-methoxybenzyl)-N-(4-methylpyrimidin-2-yl)-6-(tetrahydrofuran-2-ylmethyl)-4,5,6,7-tetrahydropyrazolo[3,4-b][1,3]thiazolo[4,5-d]azepin-2-amine (700 mg, 1.4 mmol) in TFA (10 mL) and TfOH (1 mL) was stirred at 100° C. for 1.5 h. The mixture was concentrated in vacuo, and then DCM:MeOH (10:1) was added. The solution was basified with K₂CO₃, then filtered and concentrated. The residue was purified by Prep.TLC (DCM:MeOH=10:1), and Prep-HPLC to yield the title product (103 mg, 19%).

MS (ESI): m/z 384 (M+H)⁺;

¹H-NMR (400 MHz, DMSO-d₆): δ 11.76 (s, 1H), 11.31 (s, 1H), 8.38 (d, J=4.8 Hz, 1H), 7.26 (s, 1H), 6.83 (d, J=4.8 Hz, 1H), 4.09 (s, 1H), 3.73 (t, J=6.8 Hz, 1H), 3.58 (t, J=6.8 Hz, 1H), 3.47-3.50 (m, 4H), 2.93-2.95 (m, 2H), 2.35 (s, 3H), 1.80-1.86 (m, 1H), 1.73-1.78 (m, 2H), 1.48-1.50 (m, 1H).

Example 10: N,N-Dimethyl-2-(2-(4-methylpyrimidin-2-ylamino)-4,5-dihydro pyrazolo[3,4-b]thiazolo[4,5-d]azepin-6(8H)-yl)acetamide (Final Compound 1-17)

3-(Benzylamino)-N-methoxy-1-(4-methoxybenzyl)-N-methyl-1H-pyrazole-4-carboxamide According to Scheme 8, Step 1: The title compound was obtained using the same procedure as described in Scheme 1, Step 5 with 3-chloro-N-methoxy-1-(4-methoxybenzyl)-N-methyl-1H-pyrazole-4-carboxamide (2.00 g, 6.46 mmol, synthesized as Scheme 1, Step 4) and pentylmethanamine (7.05 mL, 64.6 mmol) in NMP (15 mL) to yield 3-(benzylamino)-N-methoxy-1-(4-methoxybenzyl)-N-methyl-1H-pyrazole-4-carboxamide (1.31 mmol, 500 mg, 12%).

UPLC-MS: RT=1.04 min; MS m/z ES⁺=381.

3-(Allyl(benzyl)amino)-N-methoxy-1-(4-methoxybenzyl)-N-methyl-1H-pyrazole-4-carboxamide According to Scheme 8, Step 2: The title compound was obtained using the same procedure as described in Scheme 1, Step 6 with 3-(benzylamino)-N-methoxy-1-(4-methoxybenzyl)-N-methyl-1H-pyrazole-4-carboxamide (3.00 g, 3.15 mmol), NaH (378 mg, 9.46 mmol, 60%) and 3-bromoprop-1-ene (0.53 mL 6.31 mmol) in THF/DMF (1/1, 40 mL) to yield 3-(allyl(benzyl)amino)-N-methoxy-1-(4-methoxybenzyl)-N-methyl-1H-pyrazole-4-carboxamide (1.28 mmol, 540 mg, 41%).

UPLC-MS: RT=1.13 min; MS m/z ES⁺=421.

1-(3-(Allyl(benzyl)amino)-1-(4-methoxybenzyl)-1H-pyrazol-4-yl)prop-2-en-1-one

According to Scheme 8, Step 3: The title compound was obtained using the same procedure as described in Scheme 1, Step 7 with 3-(allyl(benzyl)amino)-N-methoxy-1-(4-methoxybenzyl)-N-methyl-1H-pyrazole-4-carboxamide (540 mg, 1.28 mmol) and vinylmagnesium bromide (3.85 mL, 3.85 mmol) in THF (10 mL) to yield 1-(3-(allyl(benzyl)

amino)-1-(4-methoxybenzyl)-1H-pyrazol-4-yl)prop-2-en-1-one (1.19 mmol, 460 mg, 92%).

UPLC-MS: RT=1.26 min; MS m/z ES$^+$=388.

(Z)-8-Benzyl-2-(4-methoxybenzyl)-7,8-dihydropyrazolo[3,4-b]azepin-4(2H)-one

According to Scheme 8, Step 4: The title compound was obtained using the same procedure as described in Scheme 1, Step 8 with 1-(3-(allyl(benzyl)amino)-1-(4-methoxybenzyl)-1H-pyrazol-4-yl)prop-2-en-1-one (460 mg, 1.19 mmol) and Grubbs catalyst 2$^{nd}$ generation (benzylidene[1,3-bis(2,4,6-trimethylphenyl)-2-imidazolidinylidene]dichloro(tricyclohexylphosphine)ruthenium, 101 mg, 0.12 mmol) to yield (Z)-8-benzyl-2-(4-methoxybenzyl)-7,8-dihydropyrazolo[3,4-b]azepin-4(2H)-one (0.61 mmol, 220 mg, 52%).

UPLC-MS: RT=1.08 min; MS m/z ES$^+$=360.

2-(4-Methoxybenzyl)-5,6,7,8-tetrahydropyrazolo[3,4-b]azepin-4(2H)-one

According to Scheme 8, Step 5: The title compound was obtained using the same procedure as described in Scheme 1, Step 9 with (Z)-8-benzyl-2-(4-methoxybenzyl)-7,8-dihydropyrazolo[3,4-b]azepin-4(2H)-one (170 mg, 0.47 mmol), ammonium formate (298 mg, 4.73 mmol) and Pd(OH)$_2$ (13.3 mg, 95.0 μmol) to yield 2-(4-methoxybenzyl)-5,6,7,8-tetrahydropyrazolo[3,4-b]azepin-4(2H)-one (221 μmol, 60 mg, 47%).

UPLC-MS: RT=0.68; MS m/z ES$^+$=272.

2-(2-(4-Methoxybenzyl)-4-oxo-4,5,6,7-tetrahydropyrazolo[3,4-b]azepin-8(2H)-yl)-N,N-dimethylacetamide According to Scheme 8, Step 6, Method A: To a solution of 2-(4-methoxybenzyl)-5,6,7,8-tetrahydropyrazolo[3,4-b]azepin-4(2H)-one (200 mg, 0.74 mmol) in THF (1 mL) was added 60% NaH (59.0 mg, 1.47 mmol) at 0° C. and the reaction mixture was stirred at rt for 30 min. 2-Chloro-N,N-dimethylacetamide (91 μL, 885 μmol) was then added and the reaction mixture was stirred at reflux for 30 min. Water was added to the mixture. The aqueous layer was extracted 3 times with EtOAc. The organic layers were combined, dried over MgSO$_4$, filtered and concentrated under reduced pressure. The crude residue was purified by flash chromatography over silica gel using (DCM/EtOH/NH$_3$, 90:9:1) (100:0 to 50:50) as eluent to yield 2-(2-(4-methoxybenzyl)-4-oxo-4,5,6,7-tetrahydropyrazolo[3,4-b]azepin-8(2H)-yl)-N,N-dimethylacetamide (0.34 mmol, 122 mg, 46%).

UPLC-MS: RT=0.73; MS m/z ES$^+$=357.

N,N-Dimethyl-2-(2-(4-methylpyrimidin-2-ylamino)-4,5-dihydropyrazolo[3,4-b]thiazolo[4,5-d]azepin-6(8H)-yl)acetamide (18 μmol, 6.8 mg, 62%) was obtained as a yellow solid following the same experimental part as described in the Scheme 1 from Steps 10 to 12, Method A.

UPLC-MS: RT=0.67 min; MS m/z ES$^+$=385;

$^1$H-NMR (300 MHz, CD$_3$OD): 8.4 (1H, d, 5.1 Hz), 7.8 (1H, s), 6.8 (1H, d, 5.1 Hz), 4.3 (2H, s), 3.5 (2H, m), 3.1 (2H, m), 3.1 (3H, s), 2.9 (3H, s), 2.5 (3H, s).

Example 11: N-(5-Fluoropyrimidin-2-yl)-6-(3-methoxypropyl)-4,5,6,8-tetrahydropyrazolo[3,4-b]thiazolo[4,5-d]azepin-2-amine (Final Compound 1-33)

2-(4-Methoxybenzyl)-8-(3-methoxypropyl)-5,6,7,8-tetrahydropyrazolo[3,4-b]azepin-4(2H)-one According to Scheme 8, Step 6, Method C: A mixture of KOtBu (310 mg, 2.76 mmol), 18-Crown-6 (731 mg, 2.76 mmol) and 2-(4-methoxybenzyl)-5,6,7,8-tetrahydropyrazolo[3,4-b]azepin-4(2H)-one (500 mg, 1.84 mmol) in THF (9.2 mL) was stirred at rt for 15 min. Then 1-bromo-3-methoxypropane (423 mg, 2.76 mmol) was added and the reaction mixture was stirred at 50° C. for 45 min. As the conversion was not complete, all the reagents were added. The solvent was evaporated under reduced pressure and the crude residue was diluted with EtOAc. The organic layer was washed with a saturated aqueous solution of NaHCO$_3$, dried over MgSO$_4$, filtered and concentrated under reduced pressure. The crude residue was purified by flash chromatography over silica gel using cyclohexane/EtOAc (100:0 to 40:60) as eluent to yield the title compound (0.81 mmol, 280 mg, 44%).

UPLC-MS: RT=0.86 min; MS m/z ES$^+$=344.

N-(5-fluoropyrimidin-2-yl)-6-(3-methoxypropyl)-4,5,6,8-tetrahydropyrazolo[3,4-b]thiazolo[4,5-d]azepin-2-amine (16 mmol, 6 mg, 5%) was obtained as a yellow solid following the same experimental part as described in the Scheme 4.

UPLC-MS: RT=0.82 min; MS m/z ES$^+$=376;

$^1$H-NMR (300 MHz, CDCl$_3$): 8.68 (2H, s), 7.88 (1H, s), 3.68-3.66 (2H, m), 3.53-3.40 (4H, m), 3.36 (3H, s), 3.11-3.08 (2H, m), 2.00-1.95 (2H, m).

Example 12: 6-(Cyclohexylmethyl)-N-(5-fluoropyrimidin-2-yl)-4,5,6,8-tetrahydropyrazolo[3,4-b]thiazolo[4,5-d]azepin-2-amine (Final Compound 1-38)

8-(Cyclohexylmethyl)-2-(4-methoxybenzyl)-5,6,7,8-tetrahydropyrazolo[3,4-b]azepin-4(2H)-one According to Scheme 8, Step 6, Method D: A mixture of (bromomethyl)cyclohexane (0.31 mL, 2.21 mmol), NaH (88 mg, 2.21 mmol) and NaI (331 mg, 2.21 mmol) in DMF (1 mL) was stirred for 30 min. Then 2-(4-methoxybenzyl)-5,6,7,8-tetrahydropyrazolo[3,4-b]azepin-4(2H)-one (300 mg, 1.11 mmol) was added and the reaction mixture was stirred at 60° C. for 1 h. As the conversion was not complete, 2 more equivalents of (bromomethyl)cyclohexane were added. The mixture was quenched with NH$_4$Cl solution, washed with brine and extracted with EtOAc. The organic layer was dried over MgSO$_4$, filtered and concentrated under reduced pressure. The crude residue was purified by flash chromatography over silica gel using cyclohexane/EtOAc (100:0 to 50:50) as eluent to yield the title compound (272 μmol, 100 mg, 25%).

UPLC-MS: RT=1.17 min; MS m/z ES$^+$=367.

6-(Cyclohexylmethyl)-N-(5-fluoropyrimidin-2-yl)-4,5,6,8-tetrahydropyrazolo[3,4-b]thiazolo[4,5-d]azepin-2-amine (13 μmol, 5 mg, 32%) was obtained as a yellow solid following the same experimental part as described in the Scheme 4.

UPLC-MS: RT=1.12 min; MS m/z ES$^+$=400;

$^1$H-NMR (300 MHz, DMSO-d$_6$): 11.81-11.66 (2H, m), 8.69 (2H, s), 7.65 (1H, s), 3.18 (2H, d), 2.99 (2H, d), 1.73-1.60 (6H, m), 1.22-1.14 (2H, m), 0.92-0.89 (2H, m).

Example 13: N-(5-Fluoropyrimidin-2-yl)-6-((5-methylisoxazol-3-yl)methyl)-4,5,6,8-tetrahydropyrazolo[3,4-b]thiazolo[4,5-d]azepin-2-amine (Final Compound 1-22)

1-(3-Chloro-1-(4-methoxybenzyl)-1H-pyrazol-4-yl)ethanone

According to Scheme 9, Step 1: To a solution of 3-chloro-N-methoxy-1-(4-methoxybenzyl)-N-methyl-1H-pyrazole- 4-carboxamide (25 g, 81 mmol, synthesized as in Scheme 1) in THF (200 mL) was added methylmagnesium bromide (19.2 g, 161 mmol) and the reaction mixture was stirred at rt for 1 h. HCl 1N was added and the solution was extracted 2 times with EtOAc. The organic layers were combined, dried over MgSO$_4$, filtered and concentrated under reduced pressure to yield the title compound (75.5 mmol, 20.0 g, 94%).

UPLC-MS: RT=0.88 min; MS m/z ES$^+$=265.

1-(3-(Allylamino)-1-(4-methoxybenzyl)-1H-pyrazol-4-yl)ethanone

According to Scheme 9, Step 2: To a solution of 1-(3-chloro-1-(4-methoxybenzyl)-1H-pyrazol-4-yl)ethanone (3.00 g, 11.3 mmol) in water (40 mL) was added prop-2-en-1-amine (1.94 g, 34.0 mmol) and the reaction mixture was heated in the microwave at 130° C. for 45 min (70% of conversion by UPLC/MS). To make the reaction complete, 2 equivalents of allylamine were added to the mixture then the solution was heated in the microwave for 45 min. The mixture was diluted with EtOAc and water. The aqueous and organic layers were separated. The organic layer was dried over MgSO$_4$, filtered and concentrated under reduced pressure. The crude residue was purified by flash chromatography over silica gel using cyclohexane/EtOAc (100:0 to 70:30) as eluent to yield the title compound (9.81 mmol, 2.80 g, 87%).

UPLC-MS: RT=0.91 min; MS m/z ES$^+$=286.

1-(3-(Allylamino)-1-(4-methoxybenzyl)-1H-pyrazol-4-yl)prop-2-en-1-one

According to Scheme 9, Step 3: To a mixture of 1-(3-(allylamino)-1-(4-methoxybenzyl)-1H-pyrazol-4-yl)ethanone (1.00 g, 3.50 mmol), formaldehyde (526 mg, 17.5 mmol) and diisopropylammonium 2,2,2-trifluoroacetate (905 mg, 4.21 mmol) in THF (40 mL) was added TFA (45 µL) and the reaction mixture was stirred at 85° C. for 2 h. Then 1 equivalent of formaldehyde and 0.2 equivalent of diisopropylammonium 2,2,2-trifluoroacetate were added. The mixture was stirred at reflux for 30 min more. 1 N HCl (10 mL) was added to the mixture and then water (50 mL) and DCE (300 mL). The aqueous and organic layers were separated. The organic layer was dried over MgSO$_4$, filtered and directly used in the next step without being concentrated.

UPLC-MS: RT=0.98 min; MS m/z ES$^+$=298.

(Z)-2-(4-Methoxybenzyl)-7,8-dihydropyrazolo[3,4-b]azepin-4(2H)-one

According to Scheme 9, Step 4: The title compound was obtained using the same procedure as described in Scheme 1, Step 8 with 1-(3-(allylamino)-1-(4-methoxybenzyl)-1H-pyrazol-4-yl)prop-2-en-1-one (1.00 g, 3.36 mmol) and Grubbs catalyst 1$^{st}$ generation (277 mg, 0.34 mmol) in DCE (300 mL) to yield (Z)-2-(4-methoxybenzyl)-7,8-dihydropyrazolo[3,4-b]azepin-4(2H)-one (1.50 mmol, 405 mg, 45%).

UPLC-MS: RT=0.66 min; MS m/z ES$^+$=270.

2-(4-Methoxybenzyl)-5,6,7,8-tetrahydropyrazolo[3,4-b]azepin-4(2H)-one

According to Scheme 9, Step 5: The title compound was obtained using the same procedure as described in Scheme 1, Step 9 with (Z)-2-(4-methoxybenzyl)-7,8-dihydropyrazolo[3,4-b]azepin-4(2H)-one (1.20 g, 4.46 µmol), Pd(OH)$_2$ (63 mg, 446 mmol) and ammonium formate (2.25 g, 35.6 mmol) in MeOH (60 mL) to yield 2-(4-methoxybenzyl)-5,6,7,8-tetrahydropyrazolo[3,4-b]azepin-4(2H)-one (3.06 mmol, 830 mg, 69%).

UPLC-MS: RT=0.65 min; MS m/z ES$^+$=272.

N-(5-fluoropyrimidin-2-yl)-6-((5-methylisoxazol-3-yl)methyl)-4,5,6,8-tetrahydropyrazolo[3,4-b]thiazolo[4,5-d]azepin-2-amine (14 µmol, 5.6 mg, 18%) was obtained as a yellow solid following the same experimental part as described in the Scheme 8 Step 6 Method A and Scheme 1 Step 10 until Scheme 1 Step 12 Method B.

UPLC-MS: RT=0.86 min; MS m/z ES$^+$=399;
$^1$H-NMR (300 MHz, DMSO-d$_6$): 12.0 (1H, s), 11.8 (1H, s), 8.7 (2H, s), 7.7 (1H, s), 6.1 (1H, s), 4.7 (2H, s), 3.2 (2H, m), 3.0 (2H, m), 2.3 (3H, s).

Example 14: N-(5-Fluoropyrimidin-2-yl)-6-(2-(methylsulfonyl)ethyl)-4,5,6,8-tetrahydropyrazolo[3,4-b]thiazolo[4,5-d]azepin-2-amine (Final Compound 1-28)

8-(2-(tert-Butyldimethylsilyloxy)ethyl)-2-(4-methoxybenzyl)-5,6,7,8-tetrahydropyrazolo[3,4-b]azepin-4(2H)-one According to Scheme 10, Step 1: To a solution of 2-(4-methoxybenzyl)-5,6,7,8-tetrahydropyrazolo[3,4-b]azepin-4(2H)-one (1.00 g, 3.69 mmol, synthesized as in Scheme 8, Step 5) in THF (20 mL) was added potassium 2-methylpropan-2-olate (827 mg, 7.37 mmol) and (2-bromoethoxy)(tert-butyl)dimethylsilane (4.41 g, 18.4 mmol) and the reaction mixture was stirred at 80° C. for 45 min. After addition of water to the reaction mixture, the aqueous layer was extracted twice with DCM. The organic layers were combined, washed with brine, dried over Na$_2$SO$_4$, filtered and concentrated under reduced pressure. A simple filtration over silica gel yielded the title compound (2.03 mmol, 872 mg, 55%).

UPLC-MS: RT=1.30 min; MS m/z ES$^+$=431.

6-(2-(tert-Butyldimethylsilyloxy)ethyl)-N-(5-fluoropyrimidin-2-yl)-8-(4-methoxybenzyl)-4,5,6,8-tetrahydropyrazolo[3,4-b]thiazolo[4,5-d]azepin-2-amine According to Scheme 10, Step 2: The title compound was obtained using the same procedure as described in Scheme 4, Step 1 with 1-(5-fluoropyrimidin-2-yl)thiourea (301 mg, 1.75 mmol), 8-(2-(tert-butyldimethylsilyloxy)ethyl)-2-(4-methoxybenzyl)-5,6,7,8-tetrahydropyrazolo[3,4-b]azepin-4(2H)-one (750 mg, 1.75 mmol) and I$_2$ (443 mg, 1.75 mmol) in pyridine (10 mL) to yield 6-(2-(tert-butyldimethylsilyloxy)ethyl)-N-(5-fluoropyrimidin-2-yl)-8-(4-methoxybenzyl)-4,5,6,8-tetrahydropyrazolo[3,4-b]thiazolo[4,5-d]azepin-2-amine (0.57 mmol, 330 mg, 32%) as a yellow solid.

UPLC-MS: RT=1.46 min; MS m/z ES$^+$=582.

2-(2-(5-Fluoropyrimidin-2-ylamino)-8-(4-methoxybenzyl)-4,5-dihydropyrazolo[3,4-b]thiazolo[4,5-d]azepin-6(8H)-yl)ethanol According to Scheme 10, Step 3: To a solution of 6-(2-(tert-butyldimethylsilyloxy)ethyl)-N-(5-fluoropyrimidin-2-yl)-8-(4-methoxybenzyl)-4,5,6,8-tetrahydropyrazolo[3,4-b]thiazolo[4,5-d]azepin-2-amine (300 mg, 0.52 mmol) in MeOH (1 mL) was added 6M HCl (0.5 mL) and the reaction mixture was stirred at rt for 1 h. The mixture was quenched with a saturated NaHCO$_3$ solution. The aqueous layer was extracted with EtOAc and DCM. The organic layers were combined, dried over MgSO$_4$, filtered and concentrated under reduced pressure to yield the title compound (0.48 mmol, 225 mg, 93%) as a yellow solid.

2-(2-(5-Fluoropyrimidin-2-ylamino)-8-(4-methoxybenzyl)-4,5-dihydropyrazolo[3,4-b]thiazolo[4,5-d]azepin-6(8H)-yl)ethyl 4-methylbenzenesulfonate According to Scheme 10, Step 4: To a solution of 2-(2-(5-fluoropyrimidin-2-ylamino)-8-(4-methoxybenzyl)-4,5-dihydropyrazolo[3,4-b]thiazolo[4,5-d]azepin-6(8H)-yl)ethanol (200 mg, 0.43 mmol), 4-methylbenzene-1-sulfonyl chloride (163 mg, 0.86 mmol) and N,N-dimethylpyridin-4-amine (10.4 mg, 86 µmol) in DCM (10 mL) was added Et$_3$N (119 µL, 0.86 mmol) and the reaction mixture was stirred at 90° C. for 1 h. The mixture was diluted with a saturated solution of NH$_4$Cl. The aqueous and organic layers were separated. The aqueous layer was extracted twice with DCM. The organic layers were combined, dried over Na$_2$SO$_4$, filtered and concentrated under reduced pressure. The crude residue was purified by flash chromatography over silica gel using cyclohexane/EtOAc (40:60) as eluent to yield the title compound (0.27 mmol, 170 mg, 64%) as a beige solid.

UPLC-MS: RT=1.15 min; MS m/z ES$^+$=622.

N-(5-Fluoropyrimidin-2-yl)-8-(4-methoxybenzyl)-6-(2-(methylsulfonyl)ethyl)-4,5,6,8-tetrahydropyrazolo[3,4-b]thiazolo[4,5-d]azepin-2-amine According to Scheme 10, Step 5, Method A: A mixture of 2-(2-(5-fluoropyrimidin-2-ylamino)-8-(4-methoxybenzyl)-4,5-dihydropyrazolo[3,4-b]thiazolo[4,5-d]azepin-6(8H)-yl)ethyl 4-methylbenzenesulfonate (10 mg, 16 µmol) and sodium methane sulfinate (7 mg, 69 µmol) in THF (1 mL) and DMF (0.5 mL) was stirred at 120° C. for 30 min. The reaction mixture was concentrated under reduced pressure and the crude was used in the next step without any further purification.

UPLC-MS: RT=0.92 min; MS m/z ES$^+$=530.

N-(5-Fluoropyrimidin-2-yl)-6-(2-(methylsulfonyl)ethyl)-4,5,6,8-tetrahydropyrazolo[3,4-b]thiazolo[4,5-d]azepin-2-amine According to Scheme 10, Step 6: The title compound was obtained using the same procedure as described in Scheme 1, Step 12, Method B with N-(5-fluoropyrimidin-2-yl)-8-(4-methoxybenzyl)-6-(2-(methylsulfonyl)ethyl)-4,5,6,8-tetrahydropyrazolo[3,4-b]thiazolo[4,5-d]azepin-2-amine (8.5 mg, 16 µmol) in TFA (1 mL) to yield N-(5-fluoropyrimidin-2-yl)-6-(2-(methylsulfonyl)ethyl)-4,5,6,8-tetrahydropyrazolo[3,4-b]thiazolo[4,5-d]azepin-2-amine (5 µmol, 2 mg, 30%) as a yellow solid.

UPLC-MS: RT=0.72 min; MS m/z ES$^+$=410;
$^1$H-NMR (300 MHz, DMSO-d$_6$): 11.60-11.87 (2H, m), 8.68 (2H, s), 7.69 (1H, m), 3.65 (2H, m), 3.43 (4H, m), 3.02 (2H, m).

Example 15: N-(5-Fluoropyrimidin-2-yl)-6-(2-(methylamino)ethyl)-4,5,6,8-tetrahydrohyrazolo[3,4-b]thiazolo[4,5-d]azepin-2-amine (Final Compound 1-32)

N-(5-Fluoropyrimidin-2-yl)-8-(4-methoxybenzyl)-6-(2-(methylamino)ethyl)-4,5,6,8-tetrahydropyrazolo[3,4-b]thiazolo[4,5-d]azepin-2-amine According to Scheme 10, Step 5, Method B: A mixture of 2-(2-(5-fluoropyrimidin-2-ylamino)-8-(4-methoxybenzyl)-4,5-dihydropyrazolo[3,4-b]thiazolo[4,5-a]azepin-6(8H)-yl)ethyl 4-methylbenzenesulfonate (50 mg, 80 µmol, synthesized as the Example 12 in Scheme 10) and methanamine (0.50 mL, 4.02 mmol) in EtOH (4 mL) was stirred at 80° C. for 1 h. The reaction mixture was concentrated under reduced pressure to yield the title compound as a yellow residue which was used in the next step without any further purification.

UPLC-MS: RT=0.70 min; MS m/z ES$^+$=481.

N-(5-Fluoropyrimidin-2-yl)-6-(2-(methylamino)ethyl)-4,5,6,8-tetrahydropyrazolo[3,4-b]thiazolo[4,5-d]azepin-2-amine According to Scheme 10, Step 6: The title compound was obtained using the same procedure as described in Scheme 1, Step 12, Method B with N-(5-fluoropyrimidin-2-yl)-8-(4-methoxybenzyl)-6-(2-(methylamino)ethyl)-4,5,6,8-tetrahydropyrazolo[3,4-b]thiazolo[4,5-d]azepin-2-amine in TFA (1 mL) to yield N-(5-fluoropyrimidin-2-yl)-6-(2-(methylamino)ethyl)-4,5,6,8-tetrahydropyrazolo[3,4-b]thiazolo[4,5-d]azepin-2-amine (6 µmol, 2.1 mg, 7%) as a yellow solid.

UPLC-MS: RT=0.57 min; MS m/z ES$^+$=361;
$^1$H-NMR (300 MHz, DMSO-d$_6$): 8.69 (2H, s), 7.66 (1H, s), 3.32-3.37 (4H, m), 2.98-3.02 (2H, m), 2.68-2.73 (2H, m), 2.30 (3H, s).

Example 16: 6-(Cyclopentylmethyl)-N-(5-fluoropyrimidin-2-yl)-4,5,6,8-tetrahydropyrazolo[3,4-b]thiazolo[4,5-d]azepin-2-amine (Final Compound 1-36)

N-(5-Fluoropyrimidin-2-yl)-8-(4-methoxybenzyl)-4,5,6,8-tetrahydropyrazolo[3,4-b]thiazolo[4,5-d]azepin-2-amine According to Scheme 11, Step 1: The title compound was obtained using the same procedure as described in Scheme 4, Step 1 with 2-(4-methoxybenzyl)-5,6,7,8-tetrahydropyrazolo[3,4-b]azepin-4(2H)-one (1.50 g, 5.53 mmol), I$_2$ (1.40 g, 5.53 mmol) and 1-(5-fluoropyrimidin-2-yl)thiourea (1.14 g, 6.63 mmol) in pyridine (11.1 mL) to yield N-(5-fluoropyrimidin-2-yl)-8-(4-methoxybenzyl)-4,5,6,8-tetrahydropyrazolo[3,4-b]thiazolo[4,5-d]azepin-2-amine (0.94 mmol, 400 mg, 17%).

UPLC-MS: RT=0.91 min; MS m/z ES$^+$=424.

N-(5-Fluoropyrimidin-2-yl)-N,8-bis(4-methoxybenzyl)-4,5,6,8-tetrahydropyrazolo[3,4-b]thiazolo[4,5-d]azepin-2-amine According to Scheme 11, Step 2: To a solution of N-(5-fluoropyrimidin-2-yl)-8-(4-methoxybenzyl)-4,5,6,8-tetrahydropyrazolo[3,4-b]thiazolo[4,5-d]azepin-2-amine (300 mg, 0.71 mmol) in DMF (4 mL) at 0° C. was added NaH (45.3 mg, 1.13 mmol, 60%) and the solution was stirred at 0° C. for 10 min. 1-(Chloromethyl)-4-methoxybenzene (96 µL, 0.71 mmol) was added to the mixture and the solution was stirred at 0° C. for 10 min and at rt for 30 min. The mixture was diluted with EtOAc and was washed with water. The organic layer was dried over MgSO$_4$, filtered and concentrated under reduced pressure. The crude residue was purified by flash chromatography over silica gel using DCM/(DCM/EtOH/NH$_3$, 90:9:1) (100:0 to 85:15) as eluent to yield the title compound (0.37 mmol, 200 mg, 34%).

UPLC-MS: RT=1.24 min; MS m/z ES$^+$=544.

6-(Cyclopentylmethyl)-N-(5-fluoropyrimidin-2-yl)-N,8-bis(4-methoxybenzyl)-4,5,6,8-tetrahydropyrazolo[3,4-b]thiazolo[4,5-d]azepin-2-amine According to Scheme 11, Step 3: The title compound was obtained using the same procedure as described in Scheme 8, Step 6, Method B, with N-(5-fluoropyrimidin-2-yl)-N,8-bis(4-methoxybenzyl)-4,5,6,8-tetrahydropyrazolo[3,4-b]thiazolo[4,5-d]azepin-2-amine (100 mg, 0.18 mmol), LiHMDS (346 µL, 0.37 mmol) and (iodomethyl)cyclopentane (35 µL, 276 µmol) to yield 6-(cyclopentylmethyl)-N-(5-fluoropyrimidin-2-yl)-N,8-bis(4-methoxybenzyl)-4,5,6,8-tetrahydropyrazolo[3,4-b]thiazolo[4,5-d]azepin-2-amine (128 µmol, 80 mg, 69%).

UPLC-MS: RT=1.56 min; MS m/z ES$^+$=626.

6-(Cyclopentylmethyl)-N-(5-fluoropyrimidin-2-yl)-4,5,6,8-tetrahydropyrazolo[3,4-b]thiazolo[4,5-d]azepin-2-amine According to Scheme 11, Step 4: The title compound was obtained using the same procedure as described in Scheme 1, Step 12, Method B, with 6-(cyclopentylmethyl)-N-(5-fluoropyrimidin-2-yl)-N,8-bis(4-methoxybenzyl)-4,5,6,8-tetrahydropyrazolo[3,4-b]thiazolo[4,5-d]azepin-2-amine (80 mg, 128 µmol) in TFA (2 mL) to yield 6-(cyclopentylmethyl)-N-(5-fluoropyrimidin-2-yl)-4,5,6,8-tetrahydropyrazolo[3,4-b]thiazolo[4,5-d]azepin-2-amine (21 µmol, 8 mg, 16%).

UPLC-MS: RT=1.08 min; MS m/z ES$^+$=386;
$^1$H-NMR (300 MHz, DMSO-d$_6$): 11.8 (1H, s), 11.6 (1H, s), 8.7 (2H, s), 7.6 (1H, s), 3.3 (2H, m), 3.3 (2H, m), 3.0 (2H, m), 1.4-1.8 (7H, m), 1.2 (2H, m).

Example 17: 2-(2-(5-Fluoropyrimidin-2-ylamino)-4,5-dihydropyrazolo[3,4-b]thiazolo[4,5-d]azepin-6(8H)-yl)ethanol (Final Compound 1-20)

According to Scheme 12: To a solution of N-(5-fluoropyrimidin-2-yl)-6-(2-methoxyethyl)-4,5,6,8-tetrahydropyrazolo[3,4-b]thiazolo[4,5-d]azepin-2-amine (Final compound 1-12, 10 mg, 28 µmol) in DCM (0.7 mL) was added BBr$_3$ (138 µL, 138 µmol) at 0° C. and the reaction mixture was stirred at rt for 1 h. After dilution of the reaction mixture with DCM, the organic layer was washed with water, dried over MgSO$_4$, filtered and concentrated under reduced pressure. The crude residue was purified by preparative HPLC to yield the title compound (27 µmol, 9.4 mg, 98%) as a yellow solid.

UPLC-MS: RT=0.64 min; MS m/z ES$^+$=348;
$^1$H-NMR (300 MHz, DMSO-d$_6$): 11.9 (1H, s), 11.6 (1H, s), 8.7 (2H, s), 7.7 (1H, s), 4.6 (1H, s), 3.6 (2H, m), 3.4 (4H, m), 3.0 (2H, m).

Example 18: 6-Benzyl-N-(5-fluoropyrimidin-2-yl)-4,5,6,7-tetrahydropyrazolo[3,4-b]thiazolo[4,5-d]azepin-2-amine (Final Compound 1-45)

8-Benzyl-2-(4-methoxybenzyl)-5,6,7,8-tetrahydropyrazolo[3,4-b]azepin-4(2H)-one According to Scheme 13, Step 1: A mixture of (Z)-8-benzyl-2-(4-methoxybenzyl)-7,8-dihydropyrazolo[3,4-b]azepin-4(2H)-one (11.9 g, 33.1 mmol) and Pd(OH)$_2$ (5.04 g, 4.30 mmol) in AcOH/EtOH (1:1, 414 mL) was stirred at rt for 2 h under 1 atm of H$_2$. The mixture was filtered over celite, was washed with EtOH and two products were recovered: 2-(4-methoxybenzyl)-5,6,7,8-tetrahydropyrazolo[3,4-b]azepin-4(2H)-one and 8-benzyl-2-(4-methoxybenzyl)-5,6,7,8-tetrahydropyrazolo[3,4-b]azepin-4(21-1)-one. The benzyl compound was purified by flash chromatography over silica gel using cyclohexane/EtOAc (100:0 to 80:20) as eluent to yield the title compound (1.08 mmol, 0.39 g, 3%).

UPLC-MS: RT=1.03 min; MS m/z ES$^+$=362.

6-Benzyl-N-(5-fluoropyrimidin-2-yl)-4,5,6,7-tetrahydropyrazolo[3,4-b]thiazolo[4,5-d]azepin-2-amine (5 µmol, 2 mg, 6%) was obtained following the same experimental part as described in the Scheme 4, Step 1 Scheme 1, Step 12, Method B.

UPLC-MS: RT=1.04 min; MS m/z ES$^+$=394;
$^1$H-NMR (300 MHz, DMSO-d$_6$): 8.69 (2H, s), 7.72 (1H, s), 7.38-7.32 (5H, m), 4.57 (2H, s), 3.26-3.22 (2H, m), 2.96-2.93 (2H, m).

Example 19: N-(5-Fluoropyrimidin-2-yl)-6-(3-methoxybenzyl)-4,5,6,7-tetrahydropyrazolo[3,4-b]thiazolo[4,5-d]azepin-2-amine (Final Compound 1-60)

8-(3-Methoxy-benzyl)-2-(2-trimethylsilanyl-ethoxymethyl)-5,6,7,8-tetrahydro-2H-1,2,8-triaza-azulen-4-one According to Scheme 14, Step 1: A solution of 2-((2-(trimethylsilyl)ethoxy)methyl)-5,6,7,8-tetrahydropyrazolo[3,4-b]azepin-4(2H)-one (200 mg, 0.71 mmol), 1-bromomethyl-3-methoxy-benzene (284 mg, 1.42 mmol) and K$_2$CO$_3$ (196 mg, 1.42 mmol) in NMP (3 mL) was stirred at 120° C. for 2 h. After cooling to rt, water (15 mL) was added and the mixture was extracted with EtOAc (15 mL×3). The combined organic layers were dried over Na$_2$SO$_4$, filtered and concentrated in vacuum. The residue was purified by Prep. HPLC (PE:EtOAc, 1:1) to give the desired product (200 mg, 70%).

MS (ESI): m/z 402 (M+H)$^+$

5-Bromo-8-(3-methoxy-benzyl)-5,6,7,8-tetrahydro-2H-1,2,8-triaza-azulen-4-one According to Scheme 14, Step 2: A mixture of 8-(3-methoxy-benzyl)-2-(2-trimethylsilanyl-ethoxymethyl)-5,6,7,8-tetrahydro-2H-1,2,8-triaza-azulen-4-one (200 mg, 0.50 mmol) and trimethyl phenylammomium tribromide (188 mg, 0.50 mmol) in CHCl$_3$ (5 mL) was refluxed for 1 h. After the reaction was finished, the mixture was washed with water (10 mL). Dried over Na$_2$SO$_4$, filtered and concentrated under reduced pressure to give the title compound (150 mg, 86%), which was used for the next step without further purification.

MS (ESI) m/z 350, 352 (M+H)$^+$

N-(5-Fluoro-pyrimidin-2-yl)-[6-(3-methoxy-benzyl)-4,5,6,7-tetrahydropyrazolo[3,4-b][1,3]thiazolo[4,5-d]azepin-2-amine According to Scheme 14, Step 3: A mixture of 5-bromo-8-(3-methoxy-benzyl)-5,6,7,8-tetrahydro-2H-1,2,8-triaza-azulen-4-one (150 mg, 0.43 mmol) and (5-fluoro-pyrimidin-2-yl)-thiourea (111 mg, 0.64 mmol) in t-BuOH (5 mL) and acetone (1 mL) was refluxed for 18 h. After cooling to rt, the mixture was filtered and concentrated under reduced pressure to give the crude product (15 mg, 8%).

¹H NMR (400 MHz, DMSO-d₆): δ 8.66 (s, 2H), 7.71 (s, 1H), 7.20 (d, J=8.0 Hz, 1H), 6.89-6.91 (m, 2H), 6.78 (d, J=8.0 Hz, 1H), 4.52 (s, 2H), 3.70 (s, 3H), 3.22 (s, 2H), 2.93 (s, 2H).

MS (ESI) m/z 424 (M+H)⁺

Example 20: N-(5-Fluoro-pyrimidin-2-yl)-6-(piperidin-4-ylmethyl)-4,5,6,7-tetrahydropyrazolo[3,4-b][1,3]thiazolo[4,5-d]azepin-2-amine (Final Compound 1-78)

2-(4-Methoxybenzyl)-8-(pyridin-4-ylmethyl)-5,6,7,8-tetrahydropyrazolo[3,4-b]azepin-4(2H)-one According to Scheme 15, Step 1: A suspension of 2-(4-methoxybenzyl)-5,6,7,8-tetrahydropyrazolo[3,4-b]azepin-4(2H)-one (1.6 g, 6.0 mmol), 4-(chloromethyl)pyridine (2.15 g, 17.0 mmol), K₂CO₃ (2.40 g, 14.8 mmol), LiBr (1.48 g, 17 mmol) in NMP (40 mL) was stirred at 120° C. for 4 h. After cooling to rt, the mixture was extracted with EtOAc (4×100 mL) and the combined organic layers were washed with brine, dried over MgSO₄, filtered and concentrated in vacuum. The crude product was purified by column chromatography (PE:EtOAc, 0-40%) to give the desired product (400 mg, 47%).

MS (ESI): m/z 363 (M+H)⁺.

tert-Butyl-4-((2-(4-methoxybenzyl)-4-oxo-4,5,6,7-tetrahydropyrazolo[3,4-b]azepin-8(2H)-yl)methyl)piperidine-1-carboxylate According to Scheme 15, Step 2: A solution of 2-(4-methoxybenzyl)-8-(pyridin-4-ylmethyl)-5,6,7,8-tetrahydropyrazolo[3,4-b]azepin-4(2H)-one (400 mg, 1.10 mmol), AcOH (2 mL), Boc₂O (288 mg, 1.32 mmol) and Pd(OH)₂ (0.5 g) in MeOH (20 mL) was stirred under H₂ atmosphere at 50° C. for 10 h. After cooling to rt, the mixture was filtered and concentrated. The residue was purified by Prep. TLC to give the title product (415 mg, 80%).

MS (ESI): m/z 469 (M+H)⁺.

tert-Butyl-4-((5-bromo-2-(4-methoxybenzyl)-4-oxo-4,5,6,7-tetrahydropyrazolo[3,4-b]azepin-8(2H)-yl)methyl)piperidine-1-carboxylate According to Scheme 1, Step 10: A solution of tert-butyl 4-((2-(4-methoxybenzyl)-4-oxo-4,5,6,7-tetrahydropyrazolo[3,4-b]azepin-8(2H)-yl)methyl)piperidine-1-carboxylate (415 mg, 0.90 mmol), PhNMe₃Br₃ (375 mg, 1.00 mmol) in CHCl₃ (10 mL) was stirred at 90° C. for 20 min. After cooling to rt, the mixture was extracted with DCM (3×20 mL). The combined organic layers were washed with brine, dried over MgSO₄, filtered and concentrated to give the crude product (453 mg, 92%).

MS (ESI): m/z 547, 549 (M+H)⁺.

tert-Butyl4((2-(5-fluoropyrimidin-2-ylamino)-8-(4-methoxybenzyl)-4,5-dihydro pyrazolo[3,4-b]thiazolo[4,5-d]azepin-6(8H)-yl)methyl)piperidine-1-carboxylate According to Scheme 1, Step 11: A solution of tert-butyl-4-((5-bromo-2-(4-methoxybenzyl)-4-oxo-4,5,6,7-dihydropyrazolo[3,4-b]azepin-8(2H)-yl)methyl) piperidine-1-carboxylate (453 mg, 0.83 mmol), (5-fluoro-pyrimidin-2-yl)-thiourea (171 mg, 0.99 mmol), in t-BuOH (5 mL) was stirred at 100° C. for 10 h. After cooling to rt, the mixture was filtered and concentrated in vacuum. The residue was purified by Prep. TLC (PE:EtOAc, 1:1) to give the title product (110 mg, 21%).

MS (ESI): m/z 621 (M+H)⁺.

N-(5-Fluoro-pyrimidin-2-yl)-6-(piperidin-4-ylmethyl)-4,5,6,7-tetrahydropyrazolo[3,4-b][1,3]thiazolo[4,5-d]azepin-2-amine According to Scheme 1, Step 12: A solution of tert-butyl 4-((2-(5-fluoropyrimidin-2-ylamino)-8-(4-methoxybenzyl)-4,5-dihydropyrazolo[3,4-b]thiazolo[4,5-d]azepin-6(8H)-yl)methyl)piperidine-1-carboxylate (110 mg, 0.18 mmol) in TFA (10 mL) was stirred at 120° C. for 25 min under microwave conditions. After cooling to rt, the mixture was concentrated in vacuum and the residue was then purified by Prep. HPLC to give the title product (5 mg, 7%).

MS (ESI): m/z 401 (M+H)⁺;
¹H-NMR (400 MHz, DMSO-d₆): δ 11.64 (s, 1H), 8.67 (s, 2H), 8.42 (d, 1H, J=8.4 Hz), 8.12 (d, 1H, J=11.6 Hz), 7.67 (s, 1H), 3.35 (s, 2H), 3.25 (d, 4H, J=6.4 Hz), 2.99 (s, 2H), 2.27-2.86 (m, 2H), 1.96-1.99 (m, 1H), 1.79 (d, 2H, J=12.8 Hz), 1.23-1.32 (m, 2H).

Example 21: N-(6-(Fluoromethyl)pyridin-2-yl)-6-(2-methoxyethyl)-4,5,6,7-tetrahydropyrazolo[3,4-b]thiazolo[4,5-d]azepin-2-amine (Final Compound 1-83)

2-(4-Methoxybenzyl)-8-(2-methoxyethyl)-5-thiocyanato-5,6,7,8-tetrahydropyrazolo[3,4-b]azepin-4(2H)-one According to Scheme 16, Step 1: To a solution of 5-bromo-2-(4-methoxybenzyl)-8-(2-methoxyethyl)-5,6,7,8-tetrahydropyrazolo[3,4-b]azepin-4(2H)-one (3.00 g, 7.35 mmol) in acetone (50 mL) was added KSCN (1.07 g, 11.0 mmol) at rt and the reaction mixture was stirred overnight. Water (50 mL) was added and the mixture was extracted with EtOAc (50 mL×3). The combined organic layers were washed with water and brine, and dried over Na₂SO₄, filtered and concentrated in vacuum to give the crude product (2.6 g, 93%).

MS (ESI) m/z 387 (M+H)⁺

2-Bromo-8-(4-methoxybenzyl)-6-(2-methoxyethyl)-4,5,6,8-tetrahydropyrazolo[3,4-b]thiazolo[4,5-d]azepine According to Scheme 16, Step 2: To a solution of 2-(4-methoxybenzyl)-8-(2-methoxyethyl)-5-thiocyanato-5,6,7,8-tetrahydropyrazolo[3,4-b]azepin-4(2H)-one (1.00 g, 2.59 mmol) in DCM (20 mL) was added AcOH(HBr) (20 mL) at rt. The mixture was stirred for 2 h at rt. Water (50 mL) was added and the mixture was extracted with EtOAc (40 mL×3). The combined organic layers were washed with water and brine, and dried over Na₂SO₄, filtered and concentrated under reduced pressure to give the crude product, which was purified by Prep. TLC (PE:EtOAc, 1:1) to give the title compound (105 mg, 9%).

MS (ESP m/z 449, 451 (M+H)⁺

N-(6-(Fluoromethyl)pyridin-2-yl)-8-(4-methoxybenzyl)-6-(2-methoxyethyl)-4,5,6,8-tetrahydropyrazolo[3,4-b]thiazolo[4,5-d]azepin-2-amine According to Scheme 16, Step 3: A mixture of 2-bromo-8-(4-methoxybenzyl)-6-(2-methoxyethyl)-4,5,6,8-tetrahydropyrazolo[3,4-b]thiazolo[4,5-d]azepine (50 mg, 0.11 mmol) 6-(fluoromethyl)pyridin-2-amine (16.6 mg, 132 μmol), Pd$_2$(dba)$_3$ (5 mg, 55 mop, Xantphos (6.4 mg, 11 μmol) and Cs$_2$CO$_3$ (179 mg, 0.22 mmol) in dioxane (3 mL) was stirred under N$_2$ atmosphere at 100° C. for 2 h. After cooling to rt, the mixture was filtered and concentrated in vacuum and purified by TLC (PE:EtOAc, 1:1) to give the title product 12 mg, 18%).

MS (ESI): m/z 495 (M+H)$^+$

N-(6-(Fluoromethyl)pyridin-2-yl)-6-(2-methoxyethyl)-4,5,6,7-tetrahydropyrazolo[3,4-b]thiazolo[4,5-d]azepin-2-amine According to Scheme 16, Step 4: A solution of N-(6-(fluoromethyl)pyridin-2-yl)-8-(4-methoxybenzyl)-6-(2-methoxyethyl)-4,5,6,8-tetrahydropyrazolo[3,4-b]thiazolo[4,5-d]azepin-2-amine (12 mg, 24 μmol) in TFA (3 mL) was stirred at 100° C. under microwave conditions for 1 h. After cooling to rt, the mixture was filtered, concentrated and purified by Prep. HPLC to give the final product (5 mg, 21%).

MS (ESI): m/z 375 (M+H)$^+$;

$^1$H-NMR (400 MHz, DMSO-d$_6$): δ 11.26 (s, 1H), 7.70-7.76 (m, 2H), 7.02 (d, 1H, J=8.4 Hz), 6.97 (d, 1H, J=7.6 Hz), 5.40 (d, 2H, J=44 Hz), 3.53 (s, 4H), 3.41-3.43 (m, 2H), 3.24 (s, 3H), 2.97-2.99 (m, 2H).

The compounds in the following Table have been synthesized according to the same methods as previous Examples 1 to 21, as denoted in the column denoted as "Exp. nr". The compounds denoted with the asterisk have been exemplified in the Examples.

TABLE 1

Compounds prepared according to the Examples.

| Co. nr. | Exp nr | M | A | Y |
|---|---|---|---|---|
| 1-1* | 1* | 4-methylpyrimidin-2-yl | NH | CH$_2$CH$_2$N(CH$_3$)– |
| 1-2 | 3* | 5-fluoropyrimidin-2-yl | NH | CH$_2$CH$_2$N(CH$_3$)– |
| 1-3 | 1 | 4-methylpyrimidin-2-yl | NH | CH$_2$CH$_2$N(CH$_2$CH$_3$)– |
| 1-4 | 4* | 5-fluoropyrimidin-2-yl | NH | CH$_2$CH$_2$N(cyclopropyl)– |
| 1-5 | 2* | 4-methylpyrimidin-2-yl | NH | CH$_2$CH$_2$N(iPr)– |
| 1-6 | 4 | 5-fluoropyrimidin-2-yl | NH | CH$_2$CH$_2$N(iPr)– |
| 1-7 | 2 | 4-methylpyrimidin-2-yl | NH | CH$_2$CH$_2$N(CH$_2$CH$_2$OMe)– |

TABLE 1-continued

Compounds prepared according to the Examples.

| Co. nr. | Exp nr. | M | A | Y |
|---|---|---|---|---|
| 1-8 | 2 | 5-methyl-1,2,4-thiadiazol-3-yl | NH | -CH2CH2-N(Me)- |
| 1-9 | 4 | 5-fluoro-4-methylpyrimidin-2-yl | NH | -CH2CH2-N(Me)- |
| 1-10 | 9* | 4-methylpyrimidin-2-yl | NH | -CH2CH2-N(CH2-tetrahydrofuran-2-yl)- |
| 1-11 | 2 | 4-methylpyrimidin-2-yl | NH | -CH2CH2-N(CH(Me)CH2OMe)- |
| 1-12 | 9 | 5-fluoropyrimidin-2-yl | NH | -CH2CH2-N(CH2CH2OMe)- |
| 1-13 | 5* | 6-methylpyridin-2-yl | NH | -CH2CH2-N(CH2CH2OMe)- |
| 1-14 | 2 | 6-fluoropyridin-2-yl | NH | -CH2CH2-N(CH2CH2OMe)- |
| 1-15 | 2 | 5-fluoropyridin-2-yl | NH | -CH2CH2-N(CH2CH2OMe)- |
| 1-16 | 7* | 4-methylpyrimidin-2-yl | NH | -CH2CH2-N(CH2-(1-methyl-1H-pyrazol-3-yl))- |

TABLE 1-continued

Compounds prepared according to the Examples.

| Co. nr. | Exp nr. | M | A | Y |
|---|---|---|---|---|
| 1-17 | 10* | 4-methyl-pyrimidin-2-yl | NH | -CH2CH2-N(CH2C(=O)N(Me)2)-CH2- |
| 1-18 | 2 | 4-MeO-pyrimidin-2-yl | NH | -CH2CH2-N(CH2CH2OMe)-CH2- |
| 1-19 | 2 | 5-methyl-1,2,4-thiadiazol-3-yl | NH | -CH2CH2-N(CH2CH2OMe)-CH2- |
| 1-20 | 17* | 5-F-pyrimidin-2-yl | NH | -CH2CH2-N(CH2CH2OH)-CH2- |
| 1-21 | 2 | 6-amino-pyridin-2-yl | NH | -CH2CH2-N(CH2CH2OMe)-CH2- |
| 1-22 | 13* | 5-F-pyrimidin-2-yl | NH | -CH2CH2-N(CH2-(5-methylisoxazol-3-yl))-CH2- |
| 1-23 | 10 | 5-F-pyrimidin-2-yl | NH | -CH2CH2-N(CH2-(3,5-dimethylisoxazol-4-yl))-CH2- |
| 1-24 | 10 | 5-F-pyrimidin-2-yl | NH | -CH2CH2-N(CH2-(2-isopropyloxazol-4-yl))-CH2- |
| 1-25 | 13 | 5-F-pyrimidin-2-yl | NH | -CH2CH2-NH-CH2- |
| 1-26 | 6* | 5-F-pyrimidin-2-yl | NH | -CH2CH2-N(CH2-(pyridin-2-yl))-CH2- |

TABLE 1-continued

Compounds prepared according to the Examples.

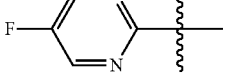

| Co. nr. | Exp nr. | M | A | Y |
|---|---|---|---|---|
| 1-27 | 13 | 5-F-pyrimidin-2-yl | NH | -CH2CH2-N(-)-CH2-(pyridin-4-yl) |
| 1-28 | 14* | 5-F-pyrimidin-2-yl | NH | -CH2CH2-N(-)-CH2CH2-SO2Me |
| 1-29 | 8* | 5-F-pyrimidin-2-yl | NH | -CH2CH2-N(-)-CH2CH2-CF3 |
| 1-30 | 7 | 5-F-pyrimidin-2-yl | NH | -CH2CH2-N(-)-CH2-CF3 |
| 1-31 | 8 | 5-F-pyrimidin-2-yl | NH | -CH2CH2-N(-)-(tetrahydrofuran-3-yl) |
| 1-32 | 15* | 5-F-pyrimidin-2-yl | NH | -CH2CH2-N(-)-CH2CH2-NHMe |
| 1-33 | 11* | 5-F-pyrimidin-2-yl | NH | -CH2CH2-N(-)-CH2CH2CH2-OMe |
| 1-34 | 9 | 5-F-pyrimidin-2-yl | NH | -CH2CH2-N(-)-Et |
| 1-35 | 11 | 5-F-pyrimidin-2-yl | NH | -CH2CH2-N(-)-CH2-(3-methylisoxazol-5-yl) |
| 1-36 | 16* | 5-F-pyrimidin-2-yl | NH | -CH2CH2-N(-)-CH2-cyclopentyl |

TABLE 1-continued

Compounds prepared according to the Examples.

| Co. nr. | Exp nr. | M | A | Y |
|---|---|---|---|---|
| 1-37 | 8 | 4-methylpyrimidin-2-yl | NH | -CH2CH2-N(-)-CH2-cyclopropyl |
| 1-38 | 12* | 5-fluoropyrimidin-2-yl | NH | -CH2CH2-N(-)-cyclohexyl |
| 1-39 | 2 | 6-methylpyridin-2-yl | NH | -CH2CH2-N(-)-CH2-cyclopropyl |
| 1-40 | 2 | 6-fluoropyridin-2-yl | NH | -CH2CH2-N(-)-CH2-cyclopropyl |
| 1-41 | 11 | 5-fluoropyrimidin-2-yl | NH | -CH2CH2-N(-)-CH2-(5-chloropyridin-2-yl) |
| 1-42 | 11 | 5-fluoropyrimidin-2-yl | NH | -CH2CH2-N(-)-CH2-(5-isopropylisoxazol-3-yl) |
| 1-43 | 10 | 5-fluoropyrimidin-2-yl | NH | -CH2CH2-N(-)-CH2CH2-O-iPr |
| 1-44 | 12 | 5-fluoropyrimidin-2-yl | NH | -CH2CH2-N(-)-CH2-cyclobutyl |
| 1-45 | 18* | 5-fluoropyrimidin-2-yl | NH | -CH2CH2-N(-)-CH2-phenyl |
| 1-46 | 19 | 4-methylpyrimidin-2-yl | NH | -CH2CH2-N(-)-CH2-(3-methylisoxazol-5-yl) |
| 1-48 | 9 | 5-fluoropyrimidin-2-yl | NH | -CH2CH2-N(-)-CH2-(tetrahydrofuran-2-yl) |

TABLE 1-continued

Compounds prepared according to the Examples.

| Co. nr. | Exp nr. | M | A | Y |
|---|---|---|---|---|
| 1-49 | 9 | 5-F-pyrimidin-2-yl | NH | -CH₂CH₂-N(-)-CH₂-(pyrimidin-2-yl) |
| 1-50 | 4 | 5-HO-pyrimidin-2-yl | NH | -CH₂CH₂-N(-)-CH₂CH₂-OMe |
| 1-51 | 9 | 5-F-pyrimidin-2-yl | NH | -CH₂CH₂-N(-)-CH₂-(tetrahydrofuran-2-yl) |
| 1-52 | 9 | 5-F-pyrimidin-2-yl | NH | -CH₂CH₂-N(-)-CH₂-(2-methyl-2H-1,2,3-triazol-4-yl) |
| 1-53 | 2 | 6-HOCH₂-pyridin-2-yl | NH | -CH₂CH₂-N(-)-CH₂CH₂-OMe |
| 1-54 | 2 | 2-methylpyrimidin-4-yl | NH | -CH₂CH₂-N(-)-CH₂CH₂-OMe |
| 1-55 | 2 | pyrimidin-4-yl | NH | -CH₂CH₂-N(-)-CH₂CH₂-OMe |
| 1-56 | 9 | 5-F-pyrimidin-2-yl | NH | -CH₂CH₂-N(-)-CH₂-(1H-pyrazol-5-yl) |
| 1-57 | 9 | 5-F-pyrimidin-2-yl | NH | -CH₂CH₂-N(-)-CH₂-(4-bromo-1H-pyrazol-5-yl) |
| 1-58 | 9 | 5-F-pyrimidin-2-yl | NH | -CH₂CH₂-N(-)-CH₂-(4-chlorophenyl) |

TABLE 1-continued

Compounds prepared according to the Examples.

| Co. nr. | Exp nr. | M | A | Y |
|---|---|---|---|---|
| 1-59 | 9 | 5-F-pyrimidin-2-yl | NH | -CH2CH2-N(-)-CH2-(2-methylphenyl) |
| 1-60 | 19* | 5-F-pyrimidin-2-yl | NH | -CH2CH2-N(-)-CH2-(3-methoxyphenyl) |
| 1-61 | 9 | 5-F-pyrimidin-2-yl | NH | -CH2CH2-N(-)-CH2-(5-fluoropyridin-2-yl) |
| 1-62 | 9 | 5-F-pyrimidin-2-yl | NH | -CH2CH2-N(-)-CH2-(5-CF3-pyridin-2-yl) |
| 1-63 | 9 | 5-F-pyrimidin-2-yl | NH | -CH2CH2-N(-)-CH2-(4-methylpyridin-2-yl) |
| 1-64 | 9 | 5-F-pyrimidin-2-yl | NH | -CH2CH2-N(-)-CH2-(3-chloropyridin-2-yl) |
| 1-65 | 9 | 5-F-pyrimidin-2-yl | NH | -CH2CH2-N(-)-CH2CH2-phenyl |
| 1-66 | 5 | 3-F-6-methylpyridin-2-yl | NH | -CH2CH2-N(-)-CH2CH2-OMe |
| 1-67 | 9 | 5-F-pyrimidin-2-yl | NH | -CH2CH2-N(-)-CH2-(3-chlorophenyl) |

TABLE 1-continued

Compounds prepared according to the Examples.

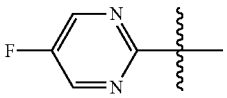 [SMILES: *c1ncc(F)cn1]

| Co. nr. | Exp nr. | M | A | Y |
|---|---|---|---|---|
| 1-68 | 9 | 5-F-pyrimidin-2-yl | NH | -CH2CH2-N(-)-CH2-(4-CN-phenyl) |
| 1-69 | 9 | 5-F-pyrimidin-2-yl | NH | -CH2CH2-N(-)-CH2-(4-CF3-phenyl) |
| 1-70 | 9 | 5-F-pyrimidin-2-yl | NH | -CH2CH2-N(-)-CH2-(6-Me-pyridin-2-yl) |
| 1-71 | 9 | 5-F-pyrimidin-2-yl | NH | -CH2CH2-N(-)-CH2CH2-(pyridin-2-yl) |
| 1-72 | 9 | 5-F-pyrimidin-2-yl | NH | -CH2CH2-N(-)-CH2-(1-Me-1,2,4-triazol-5-yl) |
| 1-73 | 9 | 5-F-pyrimidin-2-yl | NH | -CH2CH2-N(-)-CH2-(1-Me-1,2,4-triazol-3-yl) |
| 1-74 | 9 | 5-F-pyrimidin-2-yl | NH | -CH2CH2-N(-)-CH2-(2-Cl-phenyl) |
| 1-75 | 9 | 5-F-pyrimidin-2-yl | NH | -CH2CH2-N(-)-CH2-(4-F-phenyl) |
| 1-76 | 9 | 5-F-pyrimidin-2-yl | NH | -CH2CH2-N(-)-CH2-(5-CN-pyridin-2-yl) |
| 1-77 | 9 | 5-F-pyrimidin-2-yl | NH | -CH2CH2-N(-)-CH2-(5-OMe-pyridin-2-yl) |

TABLE 1-continued

Compounds prepared according to the Examples.

| Co. nr. | Exp nr. | M | A | Y |
|---|---|---|---|---|
| 1-78 | 20* | 5-F-pyrimidin-2-yl | NH | -CH₂CH₂-N(-)-CH₂-(piperidin-4-yl, NH) |
| 1-79 | 9 | 5-F-pyrimidin-2-yl | NH | -CH₂CH₂-N(-)-CH₂-(5-Cl-thiazol-2-yl) |
| 1-80 | 9 | 5-F-pyrimidin-2-yl | NH | -CH₂CH₂-N(-)-CH₂-(1-methyl-imidazol-4-yl) |
| 1-81 | 9 | 5-F-pyrimidin-2-yl | NH | -CH₂CH₂-N(-)-CH(CH₃)-(5-Cl-pyridin-2-yl) |
| 1-82 | 9 | 5-F-pyrimidin-2-yl | NH | -CH₂CH₂-N(-)-cyclobutyl |
| 1-83 | 21* | 6-F-methyl-pyridin-2-yl | NH | -CH₂CH₂-N(-)-CH₂CH₂-OMe |
| 1-84 | 9 | 5-F-pyrimidin-2-yl | NH | -CH(CH₃)-CH₂-N(-)-CH₂CH₂-OMe |

UPLC-MS Method:

UPLC-MS were recorded on Waters ACQUITY UPLC with the following conditions: Reversed phase HPLC was carried out on BEH-$C_{18}$ cartridge (1.7 μm, 2.1×50 mm) from Waters, with a flow rate of 0.8 mL/min. The gradient conditions used are: 90% A (water+0.1% of formic acid), 10% B (acetonitrile+0.1% of formic acid) to 100% B at 1.3 minutes, kept till 1.6 minutes and equilibrated to initial conditions at 1.7 minutes until 2.0 minutes. Injection volume 5 μL. ES MS detector was used, acquiring both in positive and negative ionization modes.

All mass spectra were taken under electrospray ionisation (ESI) methods.

TABLE 2

Physico-chemical data for some compounds (nd = not determined).

| Co.Nr | M. p. (° C.) | MW (theor) | [MH⁺] | RT (min) |
|---|---|---|---|---|
| 1-1 | 292 | 313.38 | 314 | 0.72 |
| 1-2 | nd | 317.34 | 318 | 0.72 |
| 1-3 | nd | 327.41 | 328 | 0.77 |
| 1-4 | nd | 357.41 | 358 | 0.92 |
| 1-5 | 247 | 341.43 | 342 | 0.85 |
| 1-6 | nd | 345.40 | 346 | 0.86 |
| 1-7 | nd | 357.43 | 358 | 0.75 |
| 1-8 | 291 | 319.41 | 320 | 0.72 |
| 1-9 | nd | 331.31 | 332 | 0.81 |
| 1-10 | nd | 383.47 | 384 | 1.69 |

TABLE 2-continued

Physico-chemical data for some compounds (nd = not determined).

| Co.Nr | M. p. (° C.) | MW (theor) | [MH+] | RT (min) |
|---|---|---|---|---|
| 1-11 | 233 | 371.46 | 372 | 1.69 |
| 1-12 | nd | 361.40 | 362 | 0.79 |
| 1-13 | nd | 356.45 | 357 | 0.68 |
| 1-14 | 203 | 360.41 | 361 | 0.86 |
| 1-15 | 218 | 360.41 | 361 | 0.84 |
| 1-16 | nd | 393.47 | 394 | 0.74 |
| 1-17 | nd | 384.46 | 385 | 0.67 |
| 1-18 | nd | 373.43 | 374 | 0.67 |
| 1-19 | nd | 363.46 | 364 | 0.76 |
| 1-20 | nd | 347.37 | 348 | 0.64 |
| 1-21 | nd | 357.43 | 358 | 0.54 |
| 1-22 | nd | 398.42 | 399 | 0.86 |
| 1-23 | 275 | 412.44 | 413 | 0.86 |
| 1-24 | 271 | 426.47 | 426 | 0.95 |
| 1-25 | 312 | 303.32 | 304 | 0.63 |
| 1-26 | nd | 394.43 | 395 | 0.62 |
| 1-27 | nd | 394.43 | 395 | 0.62 |
| 1-28 | nd | 409.46 | 410 | 0.72 |
| 1-29 | nd | 399.37 | 400 | 0.98 |
| 1-30 | nd | 385.07 | 386 | nd |
| 1-31 | nd | 373.41 | 374 | 0.77 |
| 1-32 | nd | 360.41 | 361 | 0.57 |
| 1-33 | nd | 375.42 | 376 | 0.82 |
| 1-34 | 306 | 331.37 | 332 | 0.79 |
| 1-35 | 280 | 398.42 | 399 | 0.85 |
| 1-36 | nd | 385.46 | 386 | 1.08 |
| 1-37 | nd | 353.44 | 354 | 0.87 |
| 1-38 | nd | 399.49 | 400 | 1.12 |
| 1-39 | 285 | 352.46 | 353 | 0.80 |
| 1-40 | 297 | 356.42 | 357 | 0.97 |
| 1-41 | nd | 428.87 | 429 | 0.94 |
| 1-42 | nd | 426.47 | 427 | 1.02 |
| 1-43 | nd | 389.45 | 391 | 0.95 |
| 1-44 | nd | 371.44 | 372 | 0.99 |
| 1-45 | nd | 393.44 | 394 | 1.04 |
| 1-46 | nd | 394.45 | 395 | 0.84 |
| 1-48 | nd | 387.43 | 388 | nd |
| 1-49 | nd | 395.42 | 396 | nd |
| 1-50 | nd | 359.12 | 360 | nd |
| 1-51 | nd | 387.13 | 388 | nd |
| 1-52 | nd | 398.12 | 399 | nd |
| 1-53 | nd | 372.14 | 373 | nd |
| 1-54 | nd | 357.14 | 358 | nd |
| 1-55 | nd | 343.12 | 344 | nd |
| 1-56 | nd | 383.11 | 384 | nd |
| 1-57 | nd | 461.02 | 462, 464 | nd |
| 1-58 | nd | 427.08 | 428, 430 | nd |
| 1-59 | nd | 407.13 | 408 | nd |
| 1-60 | nd | 423.13 | 424 | nd |
| 1-61 | nd | 412.10 | 413 | nd |
| 1-62 | nd | 462.10 | 463 | nd |
| 1-63 | nd | 408.13 | 409 | nd |
| 1-64 | nd | 428.07 | 429, 431 | nd |
| 1-65 | nd | 407.13 | 408 | nd |
| 1-66 | nd | 374.13 | 375 | nd |
| 1-67 | nd | 427.08 | 428, 430 | nd |
| 1-68 | nd | 418.11 | 419 | nd |
| 1-69 | nd | 461.10 | 462 | nd |
| 1-70 | nd | 408.13 | 409 | nd |
| 1-71 | nd | 408.13 | 409 | nd |
| 1-72 | nd | 398.12 | 399 | nd |
| 1-73 | nd | 398.12 | 399 | nd |
| 1-74 | nd | 427.08 | 428, 430 | nd |
| 1-75 | nd | 411.11 | 412 | nd |
| 1-76 | nd | 419.11 | 420 | nd |
| 1-77 | nd | 424.12 | 425 | nd |
| 1-78 | nd | 400.16 | 401 | 2.28 |
| 1-79 | nd | 434.03 | 435, 437 | 2.89 |
| 1-80 | nd | 397.12 | 398 | nd |
| 1-81 | nd | 442.09 | 443, 445 | 2.55 |
| 1-82 | nd | 357.12 | 358 | 2.48 |
| 1-83 | nd | 374.13 | 375 | nd |
| 1-84 | nd | 375.13 | 376 | 2.55 |

TABLE 3

| Co.Nr | NMR-data |
|---|---|
| 1-1 | $^1$H-NMR (300M Hz, DMSO-$d_6$) δ: 12.0 (s, 1H), 11.3 (s, 1H), 8.4 (d, 1H), 7.6 (s, 1H), 6.95 (d, 1H), 3.3 (m, 2H), 3.05(m, 2H), 2.95 (s, 3H), 2.45 (s, 3H) |
| 1-2 | $^1$H-NMR (300M Hz, DMSO-$d_6$) δ: 11.8 (s, 1H), 8.7 (s, 2H), 7.7 (s, 1H), 3.3 (m, 2H), 3.0 (m, 2H), 2.9 (s, 3H) |
| 1-3 | $^1$H-NMR (300M Hz, DMSO-$d_6$) δ: 11.81 (1H, s), 11.36 (1H, s), 8.42 (1H, d, 4.8 Hz), 7.66 (1H, s), 6.88 (1H, d, 4.8 Hz), 3.35-3.41 (2H, m), 3.27-3.30 (2H, m), 2.99-3.02 (2H, m), 2.41-2.43 (3H, m) |
| 1-4 | $^1$H-NMR (300M Hz, DMSO-$d_6$) δ: 12.0 (s, 1H), 11.3 (s, 1H) 8.7 (s, 2H), 7.6 (s, 1H), 3.4 (m, 2H), 3.1 (m, 2H), 2.95 (m, 2H), 2.45 (s, 3H). |
| 1-5 | $^1$H-NMR (300M Hz, DMSO-$d_6$) δ: 8.43 (1H, d, 5 Hz), 7.67 (1H, s), 6.88 (1H, d, 5 Hz), 3.34 (1H, m), 3.20-3.17 (2H, m), 2.99-2.95 (2H, m), 2.42 (3H, s), 1.14 (6H, d, 6.7 Hz). |
| 1-6 | $^1$H-NMR (300M Hz, DMSO-$d_6$) δ: 11.6-11.9 (2H, m), 8.69 (2H, s), 7.68 (1H, s), 4.12-4.21 (1H, m), 3.18-3.21 (2H, m), 2.95-2.99 (2H, m), 1.14 (6H, d, 7 Hz) |
| 1-7 | $^1$H-NMR (300M Hz, DMSO-$d_6$) δ: 8.38 (1H, d, 5.3 Hz), 7.83 (1H, s), 6.83 (1H, d, 5.3 Hz), 3.61-3.65 (2H, m), 3.56-3.59 (2H, m), 3.48-3.51 (2H, m), 3.37 (3H, s), 3.03-3.07 (2H, m), 2.48 (3H, s) |
| 1-8 | $^1$H-NMR (300M Hz, DMSO-$d_6$) δ: 12 (1H, s), 7.81 (1H, m), 3.25-3.3 (2H, m), 3.02-3.06 (2H, m), 2.95 (3H, s), 2.75 (3H, s) |
| 1-9 | $^1$H-NMR (300M Hz, DMSO-$d_6$) δ: 12 (1H, s), 11.5 (1H, s), 8.55 (1H, s), 7.7 (1H, s), 3.25-3.3 (2H, m), 3.02-3.06 (2H, m), 2.95 (3H, s), 2.45 (3H, s) |
| 1-10 | $^1$H-NMR (400M Hz, DMSO-$d_6$) δ: 11.76 (s, 1H), 11.31 (s, 1H), 8.38 (d, J = 4.8 Hz, 1H), 7.26 (s, 1H), 6.83 (d, J = 4.8 Hz, 1H), 4.09 (s, 1H), 3.73 (t, J = 6.8 Hz, 1H), 3.58 (t, J = 6.8 Hz, 1H), 3.47-3.50 (m, 4H), 2.93-2.95 (m, 2H), 2.35 (s, 3H), 1.80-1.86 (m, 1H), 1.73-1.78 (m, 2H), 1.48-1.50 (m, 1H). |
| 1-11 | $^1$H-NMR (300M Hz, CDCl$_3$) δ: 8.39 (1H, d, 4.8 Hz), 7.93 (1H, s), 6.7 (1H, d, 5.1 Hz), 4.94-4.98 (1H, m), 3.61 (2H, d, 6.3 Hz), 3.43-3.48 (2H, m), 3.48 (3H, s), 3.05-3.09 (2H, m), 2.5 (3H, s), 1.31 (3H, d, 6.8 Hz) |
| 1-12 | $^1$H-NMR (400M Hz, DMSO-$d_6$) δ: 11.80 (s, 1H), 11.60 (s, 1H), 8.66 (s, 2H), 7.64 (s, 1H), 3.52 (t, 4H, J = 4.4 Hz), 3.36 (t, 2H, J = 4.4 Hz), 3.23 (s, 3H), 2.96 (s, 2H). |
| 1-13 | $^1$H-NMR (300M Hz, CDCl$_3$) δ: 8.59 (1H, s), 8.04 (1H, s), 7.51 (1H, m), 6.81-6.74 (2H, m), 3.98 (3H, s), 3.68-3.61 (4H, m), 3.53-3.49 (2H, m), 3.07-3.04 (2H, m), 2.54 (3H, s). |
| 1-14 | $^1$H-NMR (300M Hz, DMSO-$d_6$) δ: 11.88 (1H, s), 11.4 (1H, s), 7.81-7.85 (1H, m), 6.99 (1H, dd, 8.1 Hz, 2.1 Hz), 6.59 (1H, dd, 8.1 Hz, 2.1 Hz), 3.52-3.57 (4H, m), 3.36-3.42 (2H, m), 3.27 (3H, s), 2.99-3.02 (2H, m) |
| 1-15 | $^1$H-NMR (300M Hz, DMSO-$d_6$) δ: 11.85 (1H, s), 11.19 (1H, s), 8.24 (1H, d, 3 Hz), 7.63-7.70 (2H, m), 7.11 (1H, dd, 9.3 Hz, 3.6 Hz), 3.51-3.59 (4H, m), 3.37-3.41 (2H, m), 3.27 (3H, s), 2.96-3.01 (2H, m) |
| 1-16 | $^1$H-NMR (300M Hz, CD$_3$OD) δ: 8.4 (1H, d, 4.8 Hz), 7.85 (1H, s), 7.5 (1H, d, 2.3 Hz), 6.8 (1H, d, 4.8 Hz), 6.2 (1H, d, 2.3 Hz), 4.5 (2H, s), 3.85 (3H, s), 3.35 (2H, m), 2.95 (2H, m), 2.45 (3H, s) |

TABLE 3-continued

| Co.Nr | NMR-data |
|---|---|
| 1-17 | ¹H-NMR (300M Hz, CD₃OD) δ: 8.4 (1H, d, 5.1 Hz), 7.8 (1H, s), 6.8 (1H, d, 5.1 Hz), 4.3 (2H, s), 3.5 (2H, m), 3.1 (2H, m), 3.1 (3H, s), 2.9 (3H, s), 2.5 (3H, s) |
| 1-18 | ¹H-NMR (300M Hz, DMSO-d₆) δ: 11.85 (1H, s), 11.41(1H, s), 8.28 (1H, d, 5.4 Hz), 7.67 (1H, s), 6.41 (1H, d, 5.4 Hz), 4 (3H, s), 3.51-3.57 (4H, m), 3.36-3.39 (2H, m), 3.26 (3H, s), 2.98-3.01 (2H, m) |
| 1-19 | ¹H-NMR (300M Hz, DMSO-d₆) δ: 7.67 (1H, s), 3.51-3.57 (4H, m), 3.36-3.41 (2H, m), 3.26 (3H, s), 2.95-3.00 (2H, m), 2.75 (3H, s) |
| 1-20 | ¹H-NMR (400M Hz, DMSO-d₆) δ: 11.9 (1H, s), 11.6 (1H, s), 8.7 (1H, s), 7.7 (1H, s), 4.6 (1H, s), 3.6 (2H, m), 3.4 (4H, m), 3.0 (2H, m) |
| 1-21 | ¹H-NMR (300M Hz, DMSO-d₆) δ: 10.64 (1H, s), 7.62 (1H, s), 7.24 (1H, t, 7.8 Hz), 6.14 (1H, d, 7.5 Hz), 5.93 (1H, d, 7.8 Hz), 5.82 (2H, s), 3.51-3.57 (4H, m), 3.37-3.40 (2H, m), 3.26 (3H, s), 2.93-2.97 (2H, m) |
| 1-22 | ¹H-NMR (300M Hz, DMSO-d₆) δ: 12.0 (1H, s), 11.8 (1H, s), 8.7 (2H, s), 7.7 (1H, s), 6.1 (1H, s), 4.7 (2H, s), 3.2 (2H, m), 3.0 (2H, m), 2.3 (3H, s) |
| 1-23 | ¹H-NMR (300M Hz, DMSO-d₆) δ: 8.7 (s, 2H), 7.7 (s, 1H), 4.27 (s, 2H), 3.2 (m, 2H), 2.9 (m, 2H), 2.38 (s, 3H), 2.15 (s, 3H) |
| 1-24 | ¹H-NMR (300M Hz, DMSO-d₆) δ: 8.7 (s, 2H), 7.78 (s, 1H), 7.7 (s, 1H), 4.4 (s, 2H), 3.3 (s, 2H), 3.05-2.95 (m, 3H), 1.25 (d, J = 6.6 Hz, 6H) |
| 1-25 | ¹H-NMR (300M Hz, DMSO-d₆) δ: 11.58-11.74 (m, 2H), 8.69 (s, 2H), 7.58 (s, 1H), 5.94 (s, 1H), 3.23-3.30 (m, 2H), 2.94-3.00 (m, 2H) |
| 1-26 | ¹H-NMR (300M Hz, CD₃OD) δ: 8.5 (2H, s), 8.5 (1H, m), 7.9 (1H, m), 7.8 (1H, m), 7.5 (1H, m), 7.4 (1H, m), 4.7 (2H, s), 3.4 (2H, m), 3.0 (2H, m) |
| 1-27 | ¹H-NMR (300M Hz, DMSO-d₆) δ: 8.69 (2H, s), 8.49 (2H, d, 6.4 Hz), 7.71 (1H, s), 7.33 (2H, d, 6.4 Hz), 4.61 (2H, s), 3.01-3.05 (2H, m), 2.71-2.73 (2H, m) |
| 1-28 | ¹H-NMR (300M Hz, DMSO-d₆) δ: 11.60-11.87 (2H, m), 8.68 (2H, s), 7.69 (1H, m), 3.65 (2H, m), 3.43 (4H, m), 3.02 (2H, m) |
| 1-29 | ¹H-NMR (300M Hz, DMSO-d₆) δ: 11.7(s, 1H), 8.7 (s, 2H), 7.7 (s, 1H), 3.5 (m, 4H), 3.4(m, 2H), 3.0 (m, 2H) |
| 1-30 | ¹H-NMR (400M Hz, DMSO-d₆) δ: 11.67 (br, 1H), 8.69 (s, 2H), 7.72 (s, 1H), 4.23-4.31 (m, 2H), 3.48 (t, 2H, J = 4.4 Hz), 3.04 (t, 2H, J = 4.4 Hz) |
| 1-31 | ¹H-NMR (300M Hz, DMSO-d₆) δ: 11.7 (1H, s), 8.7 (2H, s), 7.7 (1H, s), 3.5-3.55 (5H, m), 3.2-3.25 (2H, m), 3.02-3.06 (2H, m), 1.6-1.7 (2H, m) |
| 1-32 | ¹H-NMR (300M Hz, DMSO-d₆) δ: 8.69 (2H, s), 7.66 (1H, s), 3.32-3.37 (4H, m), 2.98-3.02 (2H, m), 2.68-2.73 (2H, m), 2.30 (3H, s) |
| 1-33 | ¹H-NMR (300M Hz, CDCl₃) δ: 8.68 (2H, s), 7.88 (1H, s), 3.68-3.66 (2H, m), 3.53-3.40 (4H, m), 3.36 (3H, s), 3.11-3.08 (2H, m), 2.00-1.95 (2H, m) |
| 1-34 | ¹H-NMR (300M Hz, DMSO-d₆) δ: 11.8 (1H, s), 11.6 (1H, s), 8.6 (2H, s), 7.6 (1H, s), 3.4 (2H, q, 6.9 Hz), 3.3 (2H, m), 3.0 (2H, m), 1.1 (1H, t, 6.9 Hz)<br>¹H-NMR (400M Hz, DMSO-d₆) δ: 11.89 (s, 1H), 11.72 (s, 1H), 8.77 (s, 2H), 7.73 (s, 1H), 3.41-3.42 (m, 2H), 3.37-3.38 (m, 2H), 3.08-3.09 (m, 2H), 1.20-1.22 (m, 3H) |
| 1-35 | ¹H-NMR (300M Hz, DMSO-d₆) δ: 12 (1H, s), 11.7 (1H, s), 8.75 (2H, s), 7.7 (1H, s), 6.2 (1H, s), 4.65 (2H, s), 3.45-3.5 (2H, m), 3.02-3.06 (2H, m), 2.2 (3H, s) |
| 1-36 | ¹H-NMR (300M Hz, DMSO-d₆) δ: 11.8 (1H, s), 11.6 (1H, s), 8.7 (2H, s), 7.6 (1H, s), 3.3 (2H, m), 3.3 (2H, m), 3.0 (2H, m), 1.4-1.8 (7H, m), 1.2 (2H, m) |
| 1-37 | ¹H-NMR (300M Hz, DMSO-d₆) δ: 11.8 (1H, s), 11.4 (1H, s), 8.4 (1H, d), 7.7 (1H, s), 6.9 (1H, d), 3.41-3.45 (2H, m), 3.2 (2H, d), 3.02-3.06 (2H, m), 2.4 (3H, s), 1.15-1.2 (1H, m), 0.45 (2H, d), 0.25 (2H, d) |
| 1-38 | ¹H-NMR (300M Hz, DMSO-d₆) δ: 11.81-11.66 (2H, m), 8.69 (2H, s), 7.65 (1H, s), 3.18 (2H, m), 2.99 (2H, d), 1.73-1.60 (6H, m), 1.22-1.14 (2H, m), 0.92-0.89 (2H, m) |
| 1-39 | ¹H-NMR (300M Hz, DMSO-d₆) δ: 11 (1H, s), 7.7 (1H, s), 7.6 (1H, dd), 6.8 (1H, d), 6.7 (1H, d), 3.41-3.45 (2H, m), 3.2 (2H, d), 3.02-3.06 (2H, m), 2.4 (3H, s), 1.15-1.2 (1H, m), 0.45 (2H, d), 0.25 (2H, d) |
| 1-40 | ¹H-NMR (300M Hz, DMSO-d₆) δ: 11.9 (1H, s), 11.4 (1H, s), 7.8-7.85 (1H, m), 7.7 (1H, s), 7 (1H, d), 6.6 (1H, d), 3.41-3.45 (2H, m), 3.2 (2H, d), 3.02-3.06 (2H, m), 1.15-1.2 (1H, m), 0.45 (2H, d), 0.25 (2H, d), 0.25 (2H, d) |
| 1-41 | ¹H-NMR (300M Hz, DMSO-d₆) δ: 11.7(s, 1H), 8.7 (s, 2H), 8.5 (s, 1H), 7.8 (m, 1H) 7.7 (s, 1H), 7.4 (d, 1H), 4.6 (s,2H), 3.4 (m,2H), 3.0 (m, 2H) |
| 1-42 | ¹H-NMR (300M Hz, DMSO-d₆) δ: 11.96 (1H, s), 11.68 (1H, s), 8.7 (2H, s), 7.72 (1H, s), 6.14 (1H, s), 4.55 (2H, s), 4.12 (4H, dd), 1.22 (7H, d) |
| 1-43 | ¹H-NMR (300M Hz, DMSO-d₆) δ: 11.83 (1H, s), 11.64 (1H, s), 8.69 (2H, s), 7.67 ( 1H, s), 3.56-3.61 (2H, m), 3.46-3.52 (2H, m), 3.38-3.42 (2H, m), 2.96-3.01 (2H, m), 1.08 (6H, d, 6.1 Hz) |
| 1-44 | ¹H-NMR (300M Hz, DMSO-d₆) δ: 11.79 (1H, s), 11.65 (1H, s), 8.69 (2H, s), 7.63 (1H, s), 3.34-3.31 (4H, m), 2.99-3.95 (2H, m), 2.73-2.72 (1H, m), 2.00-1.71 (6H, m) |
| 1-45 | ¹H-NMR (300M Hz, DMSO-d₆) δ: 8.69 (2H, s), 7.72 (1H, s), 7.38-7.32 (5H, m), 4.57 (2H, s), 3.26-3.22 (2H, m), 2.96-2.93 (2H, m) |
| 1-46 | ¹H-NMR (300M Hz, DMSO-d₆) δ: 11.93 (1H, s), 11.36 (1H, s), 8.43 (1H, s), 7.7 (1H, s), 6.88 (1H, s), 4.66 (2H, s), 3.41-3.38 (2H, m), 3.06-3.03 (2H, m), 2.42 (3H, s), 2.18 (3H, s) |
| 1-48 | ¹H-NMR (400M Hz, DMSO-d₆) δ: 8.65 (s, 2H), 7.63 (s, 1H), 4.09 (s, 1H), 3.72 (t, J = 6.4 Hz, 1H), 3.59 (t, J = 6.4 Hz, 1H), 3.47-3.51 (m, 4H), 2.93-2.95 (m, 2H), 1.80-1.87 (m, 1H), 1.73-1.80 (m, 2H), 1.46-1.48 (m, 1H) |
| 1-49 | ¹H-NMR (400M Hz, DMSO-d₆) δ: 8.70 (d, J = 4.8 Hz, 2H), 8.67 (s, 2H), 7.68 (s, 1H), 7.31 (t, J = 4.8 Hz, 1H), 4.77 (s, 2H), 3.62 (s, 2H), 3.03 (t, J = 4.0 Hz, 2H) |
| 1-50 | ¹H-NMR (400M Hz, DMSO-d₆) δ: 8.16 (s, 2H), 7.71 (s, 1H), 3.49-3.52 (m, 4H), 3.37 (t, J = 4.4 Hz, 2H), 3.22 (s, 3H), 2.94 (t, J = 4.4 Hz, 2H) |
| 1-51 | ¹H-NMR (400M Hz, DMSO-d₆) δ: 8.65 (s, 2H), 7.63 (s, 1H), 4.09 (s, 1H), 3.72 (t, J = 6.4 Hz, 1H), 3.59 (t, J = 6.4 Hz, 1H), 3.47-3.51 (m, 4H), 2.93-2.95 (m, 2H), 1.80-1.87 (m, 1H), 1.73-1.80 (m, 2H), 1.46-1.48 (m, 1H) |
| 1-52 | ¹H-NMR (400M Hz, DMSO-d₆) δ: 8.66 (s, 2H), 7.69 (s, 1H), 7.57 (s, 1H), 4.54 (s, 2H), 4.06 (s, 3H), 3.26 (t, J = 4.0 Hz, 2H), 2.96 (d, J = 4.4 Hz, 2H) |
| 1-53 | ¹H-NMR (400M Hz, DMSO-d₆) δ: 7.73 (s, 2H), 6.98 (d, J = 7.2 Hz, 1H), 6.90 (d, J = 8.0 Hz, 1H), 4.55 (s, 2H), 3.49-3.52 (m, 4H), 3.38 (d, J = 4.8 Hz, 2H), 3.20 (s, 3H), 2.96 (d, J = 4.8 Hz, 2H) |
| 1-54 | ¹H-NMR (300M Hz, CD₃OD) δ: 8.22 (d, 1H, J = 7.2 Hz), 7.96 (s, 1H), 6.96-7.05 (m, 1H), 3.50-3.56 (m, 6H), 3.27 (s, 3H), 3.05-3.07 (m, 2H), 2.67 (s, 3H) |
| 1-55 | ¹H-NMR (300M Hz, CD₃OD) δ: 8.97 (s, 1H), 8.37 (d, 1H, J = 6.8 Hz), 8.06 (s, 1H), 7.25 (s, 1H), 3.58-3.63 (m, 6H), 3.35 (s, 3H), 3.12 (t, 2H, J = 4.8 Hz) |
| 1-56 | ¹H-NMR (400M Hz, DMSO-d₆) δ: 8.66 (s, 2H), 7.71 (s, 1H), 7.55 (s, 1H), 6.16 (s, 1H), 4.86 (s, 2H), 3.21 (s, 2H), 2.91 (s, 2H) |
| 1-57 | ¹H-NMR (400M Hz, DMSO-d₆) δ: 8.66 (s, 2H), 7.75 (s, 1H), 7.70 (s, 1H), 4.46 (s, 2H), 3.22 (s, 2H), 2.88 (s, 2H) |
| 1-58 | ¹H-NMR (400M Hz, DMSO-d₆) δ: 8.66 (s, 2H), 7.69 (s, 1H), 7.35 (s, 4H), 4.52 (s, 2H), 3.22-3.23 (m, 2H), 2.94-2.95 (m, 2H) |
| 1-59 | ¹H-NMR (400M Hz, DMSO-d₆) δ: 8.66 (s, 2H), 7.69 (s, 1H), 7.14-7.16 (m, 1H), 7.08-7.12 (m, 3H), 4.52 (s, 2H), 3.22-3.23 (m, 2H), 2.94-2.95 (m, 2H), 2.45 (s, 3H) |

TABLE 3-continued

| Co.Nr | NMR-data |
|---|---|
| 1-60 | ¹H-NMR (400M Hz, DMSO-$d_6$) δ: 8.66 (s, 2H), 7.71 (s, 1H), 7.20 (d, J = 8.0 Hz, 1H), 6.89-6.91 (m, 2H), 6.78 (d, J = 8.0 Hz, 1H), 4.52 (s, 2H), 3.70 (s, 3H), 3.22 (s, 2H), 2.93 (s, 2H) |
| 1-61 | ¹H-NMR (400M Hz, DMSO-$d_6$) δ: 11.65 (s, 1H), 8.68 (s, 2H), 8.48 (d, 1H, J = 2.8 Hz), 7.61-7.69 (m, 2H), 7.39-7.43 (m, 1H), 4.64 (s, 2H), 3.46 (t, 2H, J = 4.4 Hz), 3.01 (t, 2H, J = 4.4 Hz) |
| 1-62 | ¹H-NMR (400M Hz, DMSO-$d_6$) δ: 8.88 (s, 1H), 8.70 (s, 2H), 8.11-8.12 (d, 1H, J = 6.8 Hz), 7.77 (s, 1H), 7.56 (d, 1H, J = 8.0 Hz), 4.77 (s, 2H), 3.56 (s, 2H),3.08 (s, 2H) |
| 1-63 | ¹H-NMR (400M Hz, CD$_3$OD) δ: 8.69 (s, 2H), 8.62 (d, 2H, J = 6.0 Hz), 7.81 (s, 1H), 7.72 (s, 1H), 4.83 (s, 2H), 3.54 (t, 2H, J = 4.0 Hz), 3.16 (t, 2H, J = 4.8 Hz), 2.53 (s, 3H) |
| 1-64 | ¹H-NMR (400M Hz, DMSO-$d_6$) δ: 8.69 (s, 2H), 8.42 (d, 1H, J = 4.0 Hz), 7.89 (d, 1H, J = 8.0 Hz), 7.68 (s, 1H), 7.30-7.33 (m, 1H), 4.80 (s, 2H), 2.98-3.10 (m, 4H) |
| 1-65 | ¹H-NMR (400M Hz, DMSO-$d_6$) δ: 8.66 (s, 2H), 7.78 (s, 1H), 7.25-7.26 (m, 4H), 7.17 (d, J = 8.0 Hz, 1H), 4.52 (s, 2H), 3.70 (s, 2H), 3.22 (s, 2H), 2.93 (s, 2H) |
| 1-66 | ¹H-NMR (400M Hz, DMSO-$d_6$) δ: 7.78 (s, 1H), 7.45-7.50 (m, 1H), 6.75-6.77 (m, 1H), 3.51-3.54 (m, 4H), 3.40-3.41 (m, 2H), 3.24 (s, 3H), 2.97-2.99 (m, 2H), 2.41 (s, 3H) |
| 1-67 | ¹H-NMR (400M Hz, DMSO-$d_6$) δ: 8.68 (s, 2H), 7.71 (s, 1H), 7.41 (s, 1H), 7.27-7.34 (m, 3H), 4.56 (s, 2H), 3.28 (s, 2H), 2.96-2.98 (m, 2H) |
| 1-68 | ¹H-NMR (400M Hz, CD$_3$OD) δ: 8.55 (s, 2H), 8.04 (s, 1H), 7.71 (d, 2H, J = 8.0 Hz), 7.52 (d, 2H, J = 8.0 Hz), 4.71 (s, 2H), 3.46 (t, 2H, J = 6.0 Hz), 3.05 (2H, J = 2.8 Hz) |
| 1-69 | ¹H-NMR (400M Hz, DMSO-$d_6$) δ: 8.67 (s, 2H), 7.70 (s, 1H), 7.64 (d, J = 8.0 Hz, 2H), 7.54 (d, J = 8.0 Hz, 2H), 4.52 (s, 2H), 3.22-3.23 (m, 2H), 2.94-2.95 (m, 2H) |
| 1-70 | ¹H-NMR (400M Hz, DMSO-$d_6$) δ: 11.83-11.91 (m, 1H), 8.87 (s, 2H), 8.38-8.42 (m, 1H), 7.90 (s, 1H), 7.81-7.85 (m, 2H), 5.00 (s, 2H), 3.29 (s, 2H), 2.82-2.86 (m, 5H) |
| 1-71 | ¹H-NMR (400M Hz, DMSO-$d_6$) δ: 8.74 (d, 1H, J = 4.8 Hz), 8.66 (s, 2H), 8.32 (t, 1H, J = 7.2 Hz), 7.84 (d, 1H, J = 7.6 Hz), 7.75 (d, 1H, J = 6.4 Hz), 7.67 (s, 1H), 3.27-3.35 (m, 6H), 2.91-2.92 (m, 2H) |
| 1-72 | ¹H-NMR (400M Hz, DMSO-$d_6$) δ: 8.64 (s, 2H), 7.77 (s, 1H), 7.66 (s, 1H), 4.63 (s, 2H), 3.40 (s, 2H), 3.84 (s, 3H), 2.95 (s, 2H) |
| 1-73 | ¹H-NMR (400M Hz, DMSO-$d_6$) δ: 8.66 (s, 2H), 8.44 (s, 1H), 7.71 (s, 1H), 4.54 (s, 2H), 3.79 (s, 2H), 3.41 (s, 3H), 2.95 (s, 2H) |
| 1-74 | ¹H-NMR (400M Hz, DMSO-$d_6$) δ: 8.67 (s, 2H), 7.73 (s, 1H), 7.36-7.42 (m, 2H), 7.24-7.26 (m, 2H), 4.63 (s, 2H), 3.38 (s, 2H), 3.00 (s, 2H) |
| 1-75 | ¹H-NMR (400M Hz, DMSO-$d_6$) δ: 11.64 (s, 1H), 8.66 (s, 2H), 7.69 (s, 1H), 7.36-7.40 (m, 2H), 7.11 (t, 2H, J = 8.8 Hz), 4.51 (s, 2H), 3.22 (t, 2H, J = 4.0 Hz), 2.93 (2H, J = 4.0 Hz) |
| 1-76 | ¹H-NMR (400M Hz, DMSO-$d_6$) δ: 11.65 (s, 1H), 8.92 (s, 1H), 8.66 (s, 2H), 8.17 (d, J = 8.0 Hz, 1H), 7.67 (s, 1H), 7.49 (d, J = 8.4 Hz, 1H), 4.72 (s, 2H), 3.35-3.36 (m, 2H), 3.04-3.05 (m, 2H) |
| 1-77 | ¹H-NMR (400M Hz, DMSO-$d_6$) δ: 8.67 (s, 2H), 8.37-8.38 (m, 1H), 7.78-7.81 (m, 1H), 7.72 (s, 1H), 7.66-7.68 (m, 1H), 4.71 (s, 2H), 3.68 (s, 3H), 3.41-3.43 (m, 2H), 3.04-3.06 (m, 2H) |
| 1-78 | ¹H-NMR (400M Hz, DMSO-$d_6$) δ: 11.64 (s, 1H), 8.67 (s, 2H), 8.42 (d, 1H, J = 8.4 Hz), 8.12 (d, 1H, J = 11.6 Hz), 7.67 (s, 1H), 3.35 (s, 2H), 3.25 (d, 4H, J = 6.4 Hz), 2.99 (s, 2H), 2.27-2.86 (m, 2H), 1.96-1.99 (m, 1H), 1.79 (d, 2H, J = 12.8 Hz), 1.23-1.32 (m, 2H) |
| 1-79 | ¹H-NMR (400M Hz, DMSO-$d_6$) δ: 12.04 (s, 1H), 11.66 (s, 1H), 8.67 (s, 2H), 7.72 (s, 1H), 7.70 (s, 1H), 4.77 (s, 2H), 3.05 (s, 4H) |
| 1-80 | ¹H-NMR (400M Hz, CD$_3$OD) δ: 11.65 (s, 1H), 8.91 (s, 1H), 8.67 (s, 2H), 7.71 (s, 1H),. 7.56 (s, 1H), 4.55 (s, 2H), 3.79 (s, 3H), 3.30 (d, 2H, J = 5.2 Hz), 3.02 (d, 2H, J = 4.0 Hz) |
| 1-81 | ¹H-NMR (400M Hz, DMSO-d6) δ: 8.66 (s, 2H), 8.56-8.57 (m, 1H), 7.83-7.86 (m, 1H), 7.76 (s, 1H), 7.48 (d, J = 8.4 Hz, 1H), 5.32-5.37 (m, 1H), 3.28-3.33 (m, 2H), 3.07-3.12 (m, 2H), 1.52 (d, J = 6.4 Hz, 3H) |
| 1-82 | ¹H-NMR (400M Hz, DMSO-$d_6$) δ: 11.43 (s, 1H), 8.47 (s, 2H), 7.45 (s, 1H), 2.99-3.00 (m, 2H), 2.79-2.82 (m, 2H), 1.49-1.54 (m, 1H), 1.91-1.97 (m, 2H), 0.20-0.24 (m, 2H), 0.03-0.06 (m, 2H) |
| 1-83 | ¹H-NMR (400M Hz, DMSO-$d_6$) δ: 11.26 (s, 1H), 7.70-7.76 (m, 2H), 7.02 (d, 1H, J = 8.4 Hz) 6.97 (d, 1H, J = 7.6 Hz), 5.40 (d, 2H, J = 44 Hz), 3.53 (s, 4H), 3.41-3.43 (m, 2H), 3.24 (s, 3H), 2.97-2.99 (m, 2H). |
| 1-84 | ¹H-NMR (400M Hz, CD$_3$OD) δ: 8.52 (s, 2H), 7.90 (s, 1H), 3.60-3.66 (m, 4H), 3.44 (d, 2H, J = 3.6 Hz), 3.35 (s, 3H), 3.30-3.32 (m, 1H), 1.34 (d, 3H, J = 7.2 Hz) |

Pharmacology

The compounds provided in the present invention are positive allosteric modulators of mGluR$_4$. As such, these compounds do not appear to bind to the orthosteric glutamate recognition site, and do not activate the mGluR$_4$ by themselves. Instead, the response of mGluR$_4$ to a concentration of glutamate or mGluR$_4$ agonist is increased when compounds of Formula (I) to (III) are present. Compounds of Formula (I) to (III) are expected to have their effect at mGluR$_4$ by virtue of their ability to enhance the function of the receptor.

mGluR$_4$ Assay on HEK-Expressing Human mGluR$_4$

The compounds of the present invention are positive allosteric modulators of mGluR$_4$ receptor. Their activity was examined on recombinant human mGluR$_{4a}$ receptors by detecting changes in intracellular $Ca^{2+}$ concentration, using the fluorescent $Ca^{2+}$-sensitive dye Fluo4-(AM) and a Fluorometric Imaging Plate Reader (FLIPR, Molecular Devices, Sunnyvale, Calif.).

Transfection and Cell Culture

The cDNA encoding the human metabotropic glutamate receptor (hmGluR$_4$), (accession number NM_000841.1, NCBI Nucleotide database browser), was subcloned into an expression vector containing also the hygromycin resistance gene. In parallel, the cDNA encoding a G protein allowing redirection of the activation signal to intracellular calcium flux was subcloned into a different expression vector containing also the puromycin resistance gene. Transfection of both these vectors into HEK293 cells with PolyFect reagent (Qiagen) according to supplier's protocol, and hygromycin and puromycin treatment allowed selection of antibiotic resistant cells which had integrated stably one or more copies of the plasmids. Positive cellular clones expressing hmGluR$_4$ were identified in a functional assay measuring changes in calcium fluxes in response to glutamate or selective known mGluR$_4$ orthosteric agonists and antagonists. HEK-293 cells expressing hmGluR$_4$ were maintained in media containing DMEM, dialyzed Fetal Calf Serum (10%), Glutamax™ (2 mM), Penicillin (100 units/mL), Streptomycin (100 μg/mL), Geneticin (100 μg/mL) and Hygromycin-B (40 μg/mL) and puromycin (1 μg/mL) at 37° C./5% $CO_2$.

Fluorescent Cell Based-$Ca^{2+}$ Mobilization Assay

Human mGluR$_4$ HEK-293 cells were plated out 24 hours prior to FLIPR[384] assay in black-walled, clear-bottomed, poly-L-ornithine-coated 384-well plates at a density of 25,000 cells/well in a glutamine/glutamate free DMEM medium containing foetal bovine serum (10%), penicillin (100 units/mL) and streptomycin (100 μg/mL) at 37° C./5% $CO_2$.

On the day of the assay, the medium was aspirated and the cells were loaded with a 3 μM solution of Fluo4-AM (LuBioScience, Lucerne, Switzerland) in 0.03% pluronic acid. After 1 hour at 37° C./5% $CO_2$, the non incorporated dye was removed by washing cell plate with the assay buffer and the cells were left in the dark at room temperature for six hours before testing. All assays were performed in a pH 7.4 buffered-solution containing 20 mM HEPES, 143 mM NaCl, 6 mM KCl, 1 mM $MgSO_4$, 1 mM $CaCl_2$, 0.125 mM sulfapyrazone and 0.1% glucose.

After 10 s of basal fluorescence recording, various concentrations of the compounds of the invention were added to the cells. Changes in fluorescence levels were first monitored for 180 s in order to detect any agonist activity of the compounds. Then the cells were stimulated by an $EC_{25}$ glutamate concentration for an additional 110 s in order to measure enhancing activities of the compounds of the invention. $EC_{25}$ glutamate concentration is the concentration giving 25% of the maximal glutamate response.

The concentration-response curves of representative compounds of the present invention were generated using the Prism GraphPad software (Graph Pad Inc, San Diego, USA). The curves were fitted to a four-parameter logistic equation:

$$Y = Bottom + (Top - Bottom)/(1 + 10^{((Log\ EC_{50} - X)*Hill\ Slope)})$$

allowing the determination of $EC_{50}$ values.

The Table 4 below represents the mean $EC_{50}$ obtained from at least three independent experiments of selected molecules performed in duplicate.

TABLE 4

Activity data for selected compounds

| Compound no. | $Ca^{2+}$ Flux* | Compound no. | $Ca^{2+}$ Flux* |
|---|---|---|---|
| 1-1 | +++ | 1-40 | ++ |
| 1-2 | ++ | 1-41 | +++ |
| 1-3 | +++ | 1-42 | +++ |
| 1-4 | +++ | 1-43 | +++ |
| 1-5 | +++ | 1-44 | +++ |
| 1-6 | +++ | 1-45 | +++ |
| 1-7 | +++ | 1-46 | +++ |
| 1-8 | +++ | 1-48 | +++ |
| 1-9 | ++ | 1-49 | +++ |
| 1-10 | +++ | 1-50 | +++ |
| 1-11 | +++ | 1-51 | +++ |
| 1-12 | +++ | 1-52 | +++ |
| 1-13 | +++ | 1-53 | + |
| 1-14 | +++ | 1-54 | + |
| 1-15 | ++ | 1-55 | + |
| 1-16 | +++ | 1-56 | ++ |
| 1-17 | ++ | 1-57 | + |
| 1-18 | +++ | 1-58 | ++ |
| 1-19 | +++ | 1-59 | + |
| 1-20 | ++ | 1-60 | ++ |
| 1-21 | +++ | 1-61 | +++ |
| 1-22 | +++ | 1-62 | +++ |
| 1-23 | +++ | 1-63 | +++ |
| 1-24 | +++ | 1-64 | ++ |
| 1-25 | +++ | 1-65 | ++ |
| 1-26 | +++ | 1-66 | ++ |
| 1-27 | +++ | 1-67 | ++ |
| 1-28 | +++ | 1-68 | +++ |
| 1-29 | ++ | 1-69 | ++ |
| 1-30 | ++ | 1-70 | ++ |
| 1-31 | +++ | 1-71 | + |
| 1-32 | + | 1-77 | +++ |
| 1-33 | +++ | 1-78 | + |
| 1-34 | +++ | 1-79 | ++ |
| 1-35 | +++ | 1-80 | ++ |

TABLE 4-continued

Activity data for selected compounds

| Compound no. | $Ca^{2+}$ Flux* | Compound no. | $Ca^{2+}$ Flux* |
|---|---|---|---|
| 1-36 | +++ | 1-81 | +++ |
| 1-37 | +++ | 1-82 | + |
| 1-38 | +++ | 1-83 | ++ |
| 1-39 | ++ | 1-84 | ++ |

*Table legend:
(+): 1 μM < $EC_{50}$ < 10 μM
(++): 100 nM < $EC_{50}$ < 1 μM
(+++): $EC_{50}$ < 100 nM The results shown in Table 4 demonstrate that the compounds described in the present invention are positive allosteric modulators of human $mGluR_4$ receptors. These compounds do not have activity by themselves but they rather increase the functional activity and/or maximal efficacy of glutamate or $mGluR_4$ agonist.

Haloperidol-Induced Catalepsy Model in the Rat

The haloperidol-induced catalepsy is a model of Parkinson's disease. It is used to assess potential anti-parkinsonian action of compound. In this model, haloperidol, a dopamine receptor antagonist, is administered to induce catalepsy, characterized by hypokinesia and rigidity. This state is described as an acute parkinsonian state. Anti-parkinsonian drugs show efficacy in this model by decreasing the catalepsy induced by haloperidol.

Experimental Design and Administration Procedure:

One day before the test, Male Sprague-Dawley rats (Charles River, les Oncins, France) were placed in individual cages. The day of the experiment, rats were injected with a dopamine D2 receptor antagonist, haloperidol (1.5 mg/kg, i.p.) 30 minutes prior to oral administration of test compound (1, 3, 10 and 30 mg/kg) or vehicle. L-DOPA-benserazide (150 mg/kg) used as a positive control, was also orally administered 30 min post-haloperidol injection.

Experimental Procedure—Catalepsy Test:

Catalepsy was assessed 60 minutes after test compound or vehicle or MTEP treatments L-DOPA-benserazide using a grid test (e.g. 90 min post-haloperidol administration). Briefly, the rats were placed on a vertical wire grid with the head pointing toward the ceiling and all paws gripping the grid. Latency to movement of both forepaws to relocate the body was measured (in seconds) with a maximum latency "cut-off" time of 120-seconds. Brain and plasma were collected at the end of the experiment for compound exposure assessment.

Unilateral 6-OHDA Lesion Treatments

The effect of test compounds were assessed alone or in combination with L-DOPA in male Sprague-Dawley rats lesioned through medial forebrain bundle (Taconic).

Animals were orally administered with test compounds and then tested 55-65 min post dosing in the forelimb stepping test for akinesia and 65-70 minutes post-dosing in the cylinder test. L-DOPA (2, 6 or 20 mg/kg), used as positive control and in co-therapy were ip injected. Then forelimb akinesia and cylinder tests were carried out 30-45-minutes post-dosing. In co-therapy, rats received test compound 30 minutres prior to L-DOPA and they were tested as described above between 55 and 75 minutes post test compound dosing.

Forelimb Stepping Test for Akinesia

Stepping movements made by the isolated ipsi- and contra-lateral forelimbs are assessed. The rat's weight is centered over the isolated limb with its head and forequarters oriented forward by the experimenter. The number of rat-initiated steps that shift weight to a new location are recorded for 30-s.

Cylinder Test

Measures spontaneous forelimb use while rats voluntarily explore a cylinder (d: 20-25 cm; h: 30 cm) and scored for the number of either ipsi-lateral, contra-lateral (affected limb), or both paw contacts during exploratory movements Preference scores are calculated for ipsi-, contra-, or both forelimb contacts during a 10-minutes interval for a minimum of 20 events. For example, a zero score (lack of asymmetry) results from equal number of events for independent ipsi-versus contra-contacts, or simultaneous contacts of both paws.

Blood samples were taken immediately after testing.

Thus, the positive allosteric modulators provided in the present invention are expected to increase the effectiveness of glutamate or mGluR$_4$ agonists at mGluR$_4$ receptor. Therefore, these positive allosteric modulators are expected to be useful for treatment of various neurological and psychiatric disorders associated with glutamate dysfunction described to be treated herein and others that can be treated by such positive allosteric modulators.

The compounds of the invention can be administered either alone, or in combination with other pharmaceutical agents effective in the treatment of conditions mentioned above.

Formulation Examples

Typical examples of recipes for the formulation of the invention are as follows:

1. Tablets

| Tablets | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced by the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 mL.

3. Injectable

A parenteral composition is prepared by stirring 1.5% by weight of active ingredient of the invention in 10% by volume propylene glycol and water.

4. Ointment

| Ointment | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I),

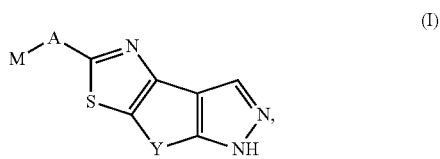

(I)

a pharmaceutically acceptable acid or base addition salt, a stereochemically isomeric form or an N-oxide form thereof, wherein M is a an optionally substituted heteroaryl;

A is NH or O;

Y is —CR$^3$R$^4$—NR$^5$—;

R$^1$, R$^2$, R$^3$ or R$^4$ are each independently selected from the group of hydrogen, halogen, —CN, —CF$_3$ or an optionally substituted radical selected from the group of —(C$_1$-C$_6$)alkyl, —(C$_1$-C$_6$)haloalkyl, —(C$_3$-C$_7$)cycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —O—(C$_0$-C$_6$)alkyl, —N—((C$_0$-C$_6$)alkyl)$_2$, —(C$_1$-C$_6$)alkyl-O—(C$_0$-C$_6$)alkyl, or —(C$_1$-C$_6$)alkyl-N—((C$_0$-C$_6$)alkyl)$_2$; or optionally, any two radicals of R (R$^1$, R$^2$, R$^3$ or R$^4$) are taken together to form an optionally substituted 3 to 10 membered carbocyclic or heterocyclic ring; and R$^5$ is selected from the group of hydrogen or an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_1$-C$_6$)haloalkyl, —(C$_1$-C$_6$)alkylene-(C$_3$-C$_7$)halocycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —(C$_2$-C$_6$)alkyl-O—(C$_0$-C$_6$)alkyl, or —(C$_2$-C$_6$)alkyl-N—((C$_0$-C$_6$)alkyl)$_2$.

2. A compound according to claim 1 of Formula (II),

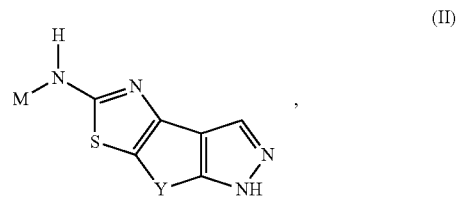

(II)

a pharmaceutically acceptable acid or base addition salt, a stereochemically isomeric form, or an N-oxide form thereof.

3. A compound according to claim 2 of Formula (III),

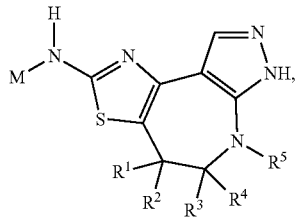

wherein,
$R^1$, $R^2$, $R^3$ or $R^4$ are each independently selected from the group of hydrogen, halogen, —CN, —CF$_3$ or an optionally substituted radical selected from the group of —(C$_1$-C$_6$)alkyl, —(C$_1$-C$_6$)haloalkyl, —(C$_3$-C$_7$)cycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —O—(C$_0$-C$_6$)alkyl, —N—((C$_0$-C$_6$)alkyl)$_2$, —(C$_1$-C$_6$)alkyl-O—(C$_0$-C$_6$)alkyl, or —(C$_1$-C$_6$)alkyl-N—((C$_0$-C$_6$)alkyl)$_2$; or optionally, any two radicals of R ($R^1$, $R^2$, $R^3$ or $R^4$) are taken together to form an optionally substituted 3 to 10 membered carbocyclic or heterocyclic ring; and
$R^5$ is selected from the group of hydrogen or an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_1$-C$_6$)haloalkyl, —(C$_1$-C$_6$)alkylene-(C$_3$-C$_7$)halocycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —(C$_1$-C$_6$)alkylene-(C$_3$-C$_7$)cycloalkyl, —(C$_2$-C$_6$)alkyl-O—(C$_0$-C$_6$)alkyl, or —(C$_2$-C$_6$)alkyl-N—((C$_0$-C$_6$)alkyl)$_2$.

4. A compound according to claim 2 of Formula (III),

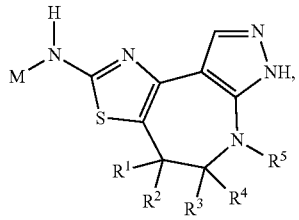

wherein,
$R^1$, $R^2$, $R^3$ or $R^4$ are each independently selected from the group of hydrogen, halogen, —CN, —CF$_3$ or an optionally substituted radical selected from the group of —(C$_1$-C$_6$)alkyl, —(C$_1$-C$_6$)haloalkyl, —(C$_3$-C$_7$)cycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —O—(C$_0$-C$_6$)alkyl, —N—((C$_0$-C$_6$)alkyl)$_2$, —(C$_1$-C$_6$)alkyl-O—(C$_0$-C$_6$)alkyl, or —(C$_1$-C$_6$)alkyl-N—((C$_0$-C$_6$)alkyl)$_2$; or optionally, any two radicals of R ($R^1$, $R^2$, $R^3$ or $R^4$) are taken together to form an optionally substituted 3 to 10 membered carbocyclic or heterocyclic ring; and
$R^5$ is selected from the group of hydrogen or an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)alkylene-(C$_1$-C$_6$)haloalkyl, —(C$_1$-C$_6$)alkylene-(C$_3$-C$_7$)halocycloalkyl, aryl, heteroaryl, heterocycle, —(C$_1$-C$_6$)alkylene-aryl, —(C$_1$-C$_6$)alkylene-heteroaryl, —(C$_1$-C$_6$)alkylene-heterocycle, —(C$_2$-C$_6$)alkyl-O—(C$_0$-C$_6$)alkyl, or —(C$_2$-C$_6$)alkyl-N—((C$_0$-C$_6$)alkyl)$_2$.

5. A compound according to claim 3 or claim 4 of Formula (III) wherein,
M is an optionally substituted pyridinyl, pyrimidinyl, thiadiazolyl, triazinyl, thiazolyl or oxadiazolyl;
$R^1$, $R^2$, $R^3$ or $R^4$ are each independently selected from the group of hydrogen and an optionally substituted —(C$_1$-C$_6$)alkyl; and
$R^5$ is selected from the group of hydrogen or an optionally substituted radical selected from the group of methyl, ethyl, isopropyl, cyclobutyl, methyl-ethylene-O-methyl, tetrahydrofuranyl, methylene-amide, methylene-trifluoromethyl, methylene-cyclopropyl, methylene-cyclobutyl, methylene-cyclopentyl, methylene-cyclohexyl, methylene-phenyl, methylene-tetrahydrofuranyl, methylene-pyrazolyl, methylene-isoxazolyl, methylene-oxazolyl, methylene-triazolyl, methylene-thiazolyl, methylene-pyrrolyl, methylene-imidazolyl, methylene-pyridinyl, methylene-pyrimidinyl, methylene-piperidinyl, ethylene-OH, ethylene-O-methyl, ethylene-O-isopropyl, ethylene-methylamine, ethylene-sulfonyl-methyl, ethylene-trifluoromethyl, ethylene-phenyl, ethylene-pyridinyl, ethylene-cyclopropyl or propylene-O-methyl.

6. A compound according to claim 3 or claim 4 of Formula (III) wherein,
M is selected from the group of pyridinyl, pyrimidinyl, thiadiazolyl or triazinyl or optionally each are substituted by hydrogen, methyl, fluoro, chloro, methoxy, amino, hydroxyl, methylenehydroxy or fluoromethylene;
$R^1$, $R^2$, $R^3$ or $R^4$ are each independently selected from the group of hydrogen or an optionally substituted —(C$_1$-C$_6$)alkyl; and
$R^5$ is selected from the group of hydrogen or an optionally substituted radical selected from the group of methyl, ethyl, isopropyl, cyclobutyl, methyl-ethylene-O-methyl, tetrahydrofuranyl, methylene-amide, methylene-trifluoromethyl, methylene-cyclopropyl, methylene-cyclobutyl, methylene-cyclopentyl, methylene-cyclohexyl, methylene-phenyl, methylene-tetrahydrofuranyl, methylene-pyrazolyl, methylene-isoxazolyl, methylene-oxazolyl, methylene-triazolyl, methylene-thiazolyl, methylene-pyrrolyl, methylene-imidazolyl, methylene-pyridinyl, methylene-pyrimidinyl, methylene-piperidinyl, ethylene-OH, ethylene-O-methyl, ethylene-O-isopropyl, ethylene-methylamine, ethylene-sulfonyl-methyl, ethylene-trifluoromethyl, ethylene-phenyl, ethylene-pyridinyl, ethylene-cyclopropyl or propylene-O-methyl.

7. A compound as in any one of the claims 1-4, which can exist as optical isomers, wherein said compound is either the racemic mixture or one or both of the individual optical isomers.

8. A compound according to claim 1, wherein said compound is selected from:
6-Methyl-N-(4-methylpyrimidin-2-yl)-4,5,6,8-tetrahydropyrazolo[3,4-b]thiazolo[4,5-d] azepin-2-amine,
N-(5-Fluoropyrimidin-2-yl)-6-methyl-4,5,6,8-tetrahydropyrazolo[3,4-b]thiazolo[4,5-d] azepin-2-amine,
6-Ethyl-N-(4-methylpyrimidin-2-yl)-4,5,6,8-tetrahydropyrazolo[3,4-b]thiazolo[4,5-d] azepin-2-amine, 6-(Cyclopropylmethyl)-N-(5-fluoropyrimidin-2-yl)-4,5, 6,8-tetrahydropyrazolo[3,4-b] thiazolo[4,5-d]azepin-2-amine, 6-Isopropyl-N-(4-methylpyrimidin-2-yl)-4,5,6,8-tetrahydropyrazolo[3,4-b]thiazolo[4,5-d]azepin-2-amine, N-(5-Fluoropyrimidin-2-yl)-6-isopropyl-4,5,6,8-tetrahydropyrazolo[3,4-b]thiazolo[4,5-d]azepin-2-amine, or 6-(2-Methoxyethyl)-N-(4-methylpyrimidin-2-yl)-4,5,6,8-tetrahydropyrazolo[3,4-b] thiazolo[4,5-d]azepin-2-amine, a pharmaceutically acceptable acid or base addition salt, a stereochemically isomeric form, or an N-oxide form thereof.

9. A compound according to claim 1, wherein said compound is selected from:

6-Methyl-N-(5-methyl-1,2,4-thiadiazol-3-yl)-4,5,6,8-tetrahydropyrazolo[3,4-b]thiazolo[4,5-d]azepin-2-amine, N-(5-Fluoro-4-methylpyrimidin-2-yl)-6-methyl-4,5,6,8-tetrahydropyrazolo[3,4-b] thiazolo[4,5-d]azepin-2-amine, N-(4-Methylpyrimidin-2-yl)-6-((tetrahydrofuran-2-yl)methyl)-4,5,6,8-tetrahydro pyrazolo[3,4-b]thiazolo[4,5-d]azepin-2-amine, 6-(1-Methoxypropan-2-yl)-N-(4-methylpyrimidin-2-yl)-4,5,6,8-tetrahydropyrazolo[3,4-b]thiazolo[4,5-d]azepin-2-amine, N-(5-Fluoropyrimidin-2-yl)-6-(2-methoxyethyl)-4,5,6,8-tetrahydropyrazolo[3,4-b] thiazolo[4,5-d]azepin-2-amine, 6-(2-Methoxyethyl)-N-(6-methylpyridin-2-yl)-4,5,6,8-tetrahydropyrazolo[3,4-b] thiazolo[4,5-d]azepin-2-amine, N-(6-Fluoropyridin-2-yl)-6-(2-methoxyethyl)-4,5,6,8-tetrahydropyrazolo[3,4-b] thiazolo[4,5-d]azepin-2-amine, N-(5-Fluoropyridin-2-yl)-6-(2-methoxyethyl)-4,5,6,8-tetrahydropyrazolo[3,4-b] thiazolo[4,5-d]azepin-2-amine, 6-((1-Methyl-1H-pyrazol-3-yl)methyl)-N-(4-methylpyrimidin-2-yl)-4,5,6,8-tetrahydro pyrazolo[3,4-b]thiazolo[4,5-d]azepin-2-amine, N,N-Dimethyl-2-(2-(4-methylpyrimidin-2-ylamino)-4,5-dihydropyrazolo[3,4-b] thiazolo[4,5-d]azepin-6(8H)-yl)acetamide, 6-(2-Methoxyethyl)-N-(4-methoxypyrimidin-2-yl)-4,5,6,8-tetrahydropyrazolo[3,4-b] thiazolo[4,5-d]azepin-2-amine, 6-(2-Methoxyethyl)-N-(5-methyl-1,2,4-thiadiazol-3-yl)-4,5,6,8-tetrahydropyrazolo[3,4-b]thiazolo[4,5-d]azepin-2-amine, 2-(2-(5-Fluoropyrimidin-2-ylamino)-4,5-dihydropyrazolo[3,4-b]thiazolo[4,5-d]azepin-6(8H)-yl)ethanol, $N^2$-(6-(2-Methoxyethyl)-4,5,6,8-tetrahydropyrazolo[3,4-b]thiazolo[4,5-d]azepin-2-yl) pyridine-2,6-diamine, N-(5-Fluoropyrimidin-2-yl)-6-((5-methylisoxazol-3-yl)methyl)-4,5,6,8-tetrahydro pyrazolo[3,4-b]thiazolo[4,5-d]azepin-2-amine, 6-((3,5-Dimethylisoxazol-4-yl)methyl)-N-(5-fluoropyrimidin-2-yl)-4,5,6,8-tetrahydro pyrazolo[3,4-b]thiazolo[4,5-d]azepin-2-amine, N-(5-Fluoropyrimidin-2-yl)-6-((2-isopropyloxazol-4-yl)methyl)-4,5,6,8-tetrahydro pyrazolo[3,4-b]thiazolo[4,5-d]azepin-2-amine, N-(5-Fluoropyrimidin-2-yl)-4,5,6,8-tetrahydropyrazolo[3,4-b]thiazolo[4,5-d]azepin-2-amine, N-(5-Fluoropyrimidin-2-yl)-6-(pyridin-2-ylmethyl)-4,5,6,8-tetrahydropyrazolo[3,4-b] thiazolo[4,5-d]azepin-2-amine, N-(5-Fluoropyrimidin-2-yl)-6-(pyridin-4-ylmethyl)-4,5,6,8-tetrahydropyrazolo[3,4-b] thiazolo[4,5-d]azepin-2-amine, N-(5-Fluoropyrimidin-2-yl)-6-(2-(methylsulfonyl)ethyl)-4,5,6,8-tetrahydropyrazolo[3,4-b]thiazolo[4,5-d]azepin-2-amine, N-(5-Fluoropyrimidin-2-yl)-6-(3,3,3-trifluoropropyl)-4,5,6,8-tetrahydropyrazolo[3,4-b] thiazolo[4,5-d]azepin-2-amine, N-(5-Fluoropyrimidin-2-yl)-6-(2,2,2-trifluoroethyl)-4,5,6,7-tetrahydropyrazolo[3,4-b] thiazolo[4,5-d]azepin-2-amine, N-(5-Fluoropyrimidin-2-yl)-6-(tetrahydrofuran-3-yl)-4,5,6,8-tetrahydropyrazolo[3,4-b] thiazolo[4,5-d]azepin-2-amine, N-(5-Fluoropyrimidin-2-yl)-6-(2-(methylamino)ethyl)-4,5,6,8-tetrahydropyrazolo[3,4-b]thiazolo[4,5-d]azepin-2-amine, N-(5-Fluoropyrimidin-2-yl)-6-(3-methoxypropyl)-4,5,6,8-tetrahydropyrazolo[3,4-b] thiazolo[4,5-d]azepin-2-amine, 6-Ethyl-N-(5-fluoropyrimidin-2-yl)-4,5,6,8-tetrahydropyrazolo[3,4-b]thiazolo[4,5-d] azepin-2-amine, N-(5-Fluoropyrimidin-2-yl)-6-((3-methylisoxazol-5-yl)methyl)-4,5,6,8-tetrahydro pyrazolo[3,4-b]thiazolo[4,5-d]azepin-2-amine, 6-(Cyclopentylmethyl)-N-(5-fluoropyrimidin-2-yl)-4,5,6,8-tetrahydropyrazolo[3,4-b] thiazolo[4,5-d]azepin-2-amine, 6-(Cyclopropylmethyl)-N-(4-methylpyrimidin-2-yl)-4,5,6,8-tetrahydropyrazolo[3,4-b] thiazolo[4,5-d]azepin-2-amine, 6-(Cyclohexylmethyl)-N-(5-fluoropyrimidin-2-yl)-4,5,6,8-tetrahydropyrazolo[3,4-b] thiazolo[4,5-d]azepin-2-amine, 6-(Cyclopropylmethyl)-N-(6-methylpyridin-2-yl)-4,5,6,8-tetrahydropyrazolo[3,4-b] thiazolo[4,5-d]azepin-2-amine, 6-(Cyclopropylmethyl)-N-(6-fluoropyridin-2-yl)-4,5,6,8-tetrahydropyrazolo[3,4-b] thiazolo[4,5-d]azepin-2-amine, 6-((5-Chloropyridin-2-yl)methyl)-N-(5-fluoropyrimidin-2-yl)-4,5,6,8-tetrahydro pyrazolo[3,4-b]thiazolo[4,5-d]azepin-2-amine, N-(5-Fluoropyrimidin-2-yl)-6-((5-isopropylisoxazol-3-yl)methyl)-4,5,6,8-tetrahydro pyrazolo[3,4-b]thiazolo[4,5-d]azepin-2-amine, N-(5-Fluoropyrimidin-2-yl)-6-(2-isopropoxyethyl)-4,5,6,8-tetrahydropyrazolo[3,4-b] thiazolo[4,5-d]azepin-2-amine, 6-(Cyclobutylmethyl)-N-(5-fluoropyrimidin-2-yl)-4,5,6,8-tetrahydropyrazolo[3,4-b] thiazolo[4,5-d]azepin-2-amine, 6-Benzyl-N-(5-fluoropyrimidin-2-yl)-4,5,6,7-tetrahydropyrazolo[3,4-b]thiazolo[4,5-d] azepin-2-amine, 6-((3-Methylisoxazol-5-yl)methyl)-N-(4-methylpyrimidin-2-yl)-4,5,6,8-tetrahydro pyrazolo[3,4-b]thiazolo[4,5-d]azepin-2-amine, N-(5-Fluoropyrimidin-2-yl)-6-((tetrahydrofuran-2-yl)methyl)-4,5,6,7-tetrahydro pyrazolo[3,4-b]thiazolo[4,5-d]azepin-2-amine, N-(5-Fluoropyrimidin-2-yl)-6-(pyrimidin-2-ylmethyl)-4,5,6,7-tetrahydropyrazolo[3,4-b]thiazolo[4,5-d]azepin-2-amine, 2-(6-(2-Methoxyethyl)-4,5,6,7-tetrahydropyrazolo[3,4-b] thiazolo[4,5-d]azepin-2-ylamino)pyrimidin-5-ol, N-(5-Fluoropyrimidin-2-yl)-6-(((R)-tetrahydrofuran-2-yl)methyl)-4,5,6,7-tetrahydro pyrazolo[3,4-b]thiazolo[4,5-d]azepin-2-amine,
N-(5-Fluoropyrimidin-2-yl)-6-((2-methyl-2H-1,2,3-triazol-4-yl)methyl)-4,5,6,7-tetrahydropyrazolo[3,4-b]thiazolo[4,5-d]azepin-2-amine,
(6-(6-(2-Methoxyethyl)-4,5,6,8-tetrahydropyrazolo[3,4-b]thiazolo[4,5-d]azepin-2-ylamino)pyridin-2-yl)methanol,
6-(2-Methoxyethyl)-N-(2-methylpyrimidin-4-yl)-4,5,6,8-tetrahydropyrazolo[3,4-b] thiazolo[4,5-d]azepin-2-amine,
6-(2-Methoxyethyl)-N-(pyrimidin-4-yl)-4,5,6,8-tetrahydropyrazolo[3,4-b]thiazolo[4,5-d]azepin-2-amine,
6-((1H-Pyrazol-5-yl)methyl)-N-(5-fluoropyrimidin-2-yl)-4,5,6,8-tetrahydropyrazolo[3,4-b]thiazolo[4,5-d]azepin-2-amine,
6-((4-Bromo-1H-pyrazol-5-yl)methyl)-N-(5-fluoropyrimidin-2-yl)-4,5,6,8-tetrahydro pyrazolo[3,4-b]thiazolo[4,5-d]azepin-2-amine,
6-(4-Chlorobenzyl)-N-(5-fluoropyrimidin-2-yl)-4,5,6,7-tetrahydropyrazolo[3,4-b] thiazolo[4,5-d]azepin-2-amine,
N-(5-Fluoropyrimidin-2-yl)-6-(2-methylbenzyl)-4,5,6,7-tetrahydropyrazolo[3,4-b] thiazolo[4,5-d]azepin-2-amine,
N-(5-Fluoropyrimidin-2-yl)-6-(3-methoxybenzyl)-4,5,6,7-tetrahydropyrazolo[3,4-b] thiazolo[4,5-d]azepin-2-amine,
6-((5-Fluoropyridin-2-yl)methyl)-N-(5-fluoropyrimidin-2-yl)-4,5,6,7-tetrahydro pyrazolo[3,4-b]thiazolo[4,5-d]azepin-2-amine,
N-(5-Fluoropyrimidin-2-yl)-6-((5-(trifluoromethyl)pyridin-2-yl)methyl)-4,5,6,7-tetrahydropyrazolo[3,4-b]thiazolo[4,5-d]azepin-2-amine,
N-(5-Fluoropyrimidin-2-yl)-6-((4-methylpyridin-2-yl)methyl)-4,5,6,7-tetrahydro pyrazolo[3,4-b]thiazolo[4,5-d]azepin-2-amine,
6-((3-Chloropyridin-2-yl)methyl)-N-(5-fluoropyrimidin-2-yl)-4, 5,6,7-tetrahydro pyrazolo[3,4-b]thiazolo[4,5-d]azepin-2-amine,
N-(5-Fluoropyrimidin-2-yl)-6-phenethyl-4, 5,6,7-tetrahydropyrazolo[3,4-b]thiazolo[4,5-d]azepin-2-amine,
N-(3-Fluoro-6-methylpyridin-2-yl)-6-(2-methoxyethyl)-4,5,6,7-tetrahydropyrazolo[3,4-b]thiazolo[4,5-d]azepin-2-amine,
6-(3-Chlorobenzyl)-N-(5-fluoropyrimidin-2-yl)-4, 5,6,7-tetrahydropyrazolo[3,4-b]thiazolo[4,5-d]azepin-2-amine,
4-((2-(5-Fluoropyrimidin-2-ylamino)-4, 5-dihydropyrazolo[3,4-b]thiazolo[4,5-d] azepin-6(7H)-yl)methyl)benzonitrile,
N-(5-Fluoropyrimidin-2-yl)-6-(4-(trifluoromethyl)benzyl)-4, 5,6,7-tetrahydropyrazolo[3,4-b]thiazolo[4,5-d]azepin-2-amine,
N-(5-Fluoropyrimidin-2-yl)-6-((6-methylpyridin-2-yl)methyl)-4,5,6,7-tetrahydro pyrazolo[3,4-b]thiazolo[4,5-d]azepin-2-amine, or
N-(5-Fluoropyrimidin-2-yl)-6-(2-(pyridin-2-yl)ethyl)-4,5,6,7-tetrahydropyrazolo[3,4-b]thiazolo[4,5-d]azepin-2-amine,
a pharmaceutically acceptable acid or base addition salt, a stereochemically isomeric form, or an N-oxide form thereof.

10. A compound according to claim 1, wherein said compound is selected from:

N-(5-Fluoropyrimidin-2-yl)-6-((1-methyl-1H-1,2,4-triazol-5-yl)methyl)-4, 5,6,7-tetrahydropyrazolo[3,4-b]thiazolo[4, 5-d]azepin-2-amine,
N-(5-Fluoropyrimidin-2-yl)-6-((1-methyl-1H-1,2,4-triazol-3-yl)methyl)-4, 5,6,7-tetrahydropyrazolo[3,4-b]thiazolo[4, 5-d]azepin-2-amine,
6-(2-Chlorobenzyl)-N-(5-fluoropyrimidin-2-yl)-4, 5,6,7-tetrahydropyrazolo[3,4-b]thiazolo[4,5-d]azepin-2-amine,
6-(4-Fluorobenzyl)-N-(5-fluoropyrimidin-2-yl)-4, 5,6,7-tetrahydropyrazolo[3,4-b]thiazolo[4,5-d]azepin-2-amine,
6-((2-(5-Fluoropyrimidin-2-ylamino)-4, 5-dihydropyrazolo[3,4-b]thiazolo[4,5-d] azepin-6(7H)-yl)methyl)nicotinonitrile,
N-(5-Fluoropyrimidin-2-yl)-6-((5-methoxypyridin-2-yl)methyl)-4, 5,6,7-tetrahydro pyrazolo[3,4-b]thiazolo[4, 5-d]azepin-2-amine,
N-(5-Fluoropyrimidin-2-yl)-6-(piperidin-4-ylmethyl)-4, 5,6,7-tetrahydropyrazolo[3,4-b]thiazolo[4,5-d]azepin-2-amine,
6-((5-Chlorothiazol-2-yl)methyl)-N-(5-fluoropyrimidin-2-yl)-4, 5,6,7-tetrahydro pyrazolo[3,4-b]thiazolo[4,5-d]azepin-2-amine,
N-(5-Fluoropyrimidin-2-yl)-6-((1-methyl-1H-imidazol-4-yl)methyl)-4, 5,6,7-tetrahydro pyrazolo[3,4-b]thiazolo[4,5-d]azepin-2-amine,
6-(1-(5-Chloropyridin-2-yl)ethyl)-N-(5-fluoropyrimidin-2-yl)-4,5,6,7-tetrahydro pyrazolo[3,4-b]thiazolo[4,5-d]azepin-2-amine,
6-Cyclobutyl-N-(5-fluoropyrimidin-2-yl)-4,5,6,7-tetrahydropyrazolo[3,4-b]thiazolo[4,5-d]azepin-2-amine,
N-(6-(Fluoromethyl)pyridin-2-yl)-6-(2-methoxyethyl)-4, 5,6,7-tetrahydropyrazolo[3,4-b]thiazolo[4,5-d]azepin-2-amine, or
N-(5-Fluoropyrimidin-2-yl)-6-(2-methoxyethyl)-4-methyl-4,5,6,7-tetrahydropyrazolo[3,4-b]thiazolo[4,5-d]azepin-2-amine,
a pharmaceutically acceptable acid or base addition salt, a stereochemically isomeric form, or an N-oxide form thereof.

11. A pharmaceutical composition comprising a therapeutically effective amount of a compound according to claim 1 and a pharmaceutically acceptable carrier and/or excipient.

12. A method of treating Parkinson's disease or Multiple Sclerosis, in a mammal, facilitated by the positive allosteric modulation of mGluR$_4$, comprising administering to said mammal in need of such treatment a pharmaceutical composition comprising a therapeutically effective amount of a compound according to any one of claim 1-4 or 8-10 inclusive.

13. A method of treating a condition in a mammal the treatment of which is affected or facilitated by the neuromodulatory effect of mGluR$_4$ positive allosteric modulators, comprising administering to a mammal in need of such treatment a pharmaceutical composition comprising a therapeutically effective amount of a compound according to any one of claim 1-4 or 8-10 inclusive.

14. A method of treating neurological or psychiatric disorders associated with glutamate dysfunction in a mammal of which is facilitated by the neuromodulatory effect of mGluR$_4$ positive allosteric modulators, comprising administering to a mammalian patient in need of such treatment a pharmaceutical composition comprising a therapeutically effective amount of a compound according to any one of claim 1-4 or 8-10 inclusive.

15. A method of treating Parkinson's disease comprising administering to a mammalian patient in need of such treatment a pharmaceutical composition comprising a therapeutically effective amount of compound according to any one of claim 1 to 4 or 8-10 in combination with an agent selected from the group consisting of: levodopa, levodopa with a selective extracerebral decarboxylase inhibitor, carbidopa, entacapone, a COMT inhibitor, or a dopamine agonist.

16. A method of treating type 2 diabetes, comprising administering to a mammalian patient in need of such treatment a pharmaceutical composition comprising a therapeutically effective amount of a compound according to any one of claim 1-4 or 8-10 inclusive.

17. A method of treating diseases or disorders of the gastrointestinal tract, gastro-esophageal reflux disease (GERD), lower esophageal sphincter diseases or disorders, diseases of gastrointestinal motility, colitis, Crohn's disease or irritable bowel syndrome (IBS), in a mammal, comprising administering to said mammal in need of such treatment, a pharmaceutical composition comprising a therapeutically effective amount of a compound according to any one of claims 1-4 inclusive.

18. A taste agent, flavour agent, flavour enhancing agent or a food additive comprising a compound of claim 1.

19. A method of modulating $mGluR_4$ activity in a mammal comprising administering to said mammal a therapeutically effective amount of a compound according to claim 1.

20. A method of modulating $mGluR_4$ activity in a mammal comprising administering to said mammal a therapeutically effective amount of a pharmaceutical composition according to claim 11.

* * * * *

UNITED STATES PATENT AND TRADEMARK OFFICE
CERTIFICATE OF CORRECTION

PATENT NO. : 9,765,091 B2
APPLICATION NO. : 13/809581
DATED : September 19, 2017
INVENTOR(S) : Christelle Bolea et al.

Page 1 of 1

It is certified that error appears in the above-identified patent and that said Letters Patent is hereby corrected as shown below:

Column no. 82, Line 29:
-CR3R4-NR5- should read --CR1R2-CR3R4-NR5--.

Signed and Sealed this
Twenty-seventh Day of March, 2018

Andrei Iancu
*Director of the United States Patent and Trademark Office*